United States Patent
Barnes-Seeman et al.

(10) Patent No.: US 10,676,499 B2
(45) Date of Patent: Jun. 9, 2020

(54) 3' END CAPS, 5' END CAPS AND COMBINATIONS THEREOF FOR THERAPEUTIC RNA

(71) Applicant: NOVARTIS AG, Basel (CH)

(72) Inventors: David Barnes-Seeman, Cambridge, MA (US); Scott Louis Cohen, Peabody, MA (US); John Louis Diener, Cambridge, MA (US); Christian Gampe, Cambridge, MA (US); James Roache, Cambridge, MA (US); Amy White, Somerville, MA (US); Sarah Williams, Milton, MA (US); Jun Yuan, Boston, MA (US); Frederic Zecri, Brookline, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/536,516

(22) PCT Filed: Dec. 16, 2015

(86) PCT No.: PCT/IB2015/059697
§ 371 (c)(1),
(2) Date: Jun. 15, 2017

(87) PCT Pub. No.: WO2016/098028
PCT Pub. Date: Jun. 23, 2016

(65) Prior Publication Data
US 2018/0002368 A1    Jan. 4, 2018

Related U.S. Application Data

(60) Provisional application No. 62/092,627, filed on Dec. 16, 2014.

(51) Int. Cl.
| | | |
|---|---|---|
| *C07H 21/02* | (2006.01) |
| *C07F 9/6561* | (2006.01) |
| *C07H 19/167* | (2006.01) |
| *C07H 19/207* | (2006.01) |
| *C07K 14/575* | (2006.01) |

(52) U.S. Cl.
CPC .......... *C07H 21/02* (2013.01); *C07F 9/65616* (2013.01); *C07H 19/167* (2013.01); *C07H 19/207* (2013.01); *C07K 14/5759* (2013.01)

(58) Field of Classification Search
None
See application file for complete search history.

(56) References Cited

U.S. PATENT DOCUMENTS

| | | | |
|---|---|---|---|
| 2003/0194759 A1* | 10/2003 | Darzynkiewiz | ......... C12P 19/34 435/68.1 |
| 2007/0135370 A1* | 6/2007 | MacLachlan | ...... C12N 15/1131 514/44 A |
| 2012/0195936 A1 | 9/2012 | Rudolph et al. | |

FOREIGN PATENT DOCUMENTS

| | | |
|---|---|---|
| WO | 2009149253 A2 | 12/2009 |
| WO | 2011012316 A2 | 2/2011 |
| WO | 2011015347 A1 | 2/2011 |
| WO | 2013101690 A1 | 7/2013 |

OTHER PUBLICATIONS

Lehninger in Biochemistry, Second Edition, Worth Publishers Inc., New York, NY, 1975, pp. 315, 733 and 734 (Year: 1975).*
Thillier et al (RNA (2012), 18:856-868) (Year: 2012).*
Sakatsume, et al., "Synthesis of Oligoribonucleotides bearing Morpholino-Nucleosides wth Carbamate Internucleoside Linkages at the 3'-Terminus", Chemistry Letters, p. 201-204. 1993.
Notification of Transmittal of the International Search Report and the Written Opinion of the International Searching Authority, or the Declaration, dated May 23, 2016 in International Patent Appl. No. PCT/IB2015/059697, International Filing Date: Dec. 16, 2015, 19 pages.

* cited by examiner

*Primary Examiner* — Richard A Schnizer
(74) *Attorney, Agent, or Firm* — Jana Dailey

(57) ABSTRACT

The disclosure relates to nucleic acids that contain modifications at the 5'-end, 3'-end or 5'-end and 3'-ends, and compounds that can be used to make the modified nucleic acids are disclosed. The modified nucleic acids have improved expression, lower immunogenicity and improved stability compared to unmodified nucleic acids.

2 Claims, 3 Drawing Sheets

3' END CAPS, 5' END CAPS AND COMBINATIONS THEREOF FOR THERAPEUTIC RNA

This application is a U.S. National Phase filing of International Application No. PCT/IB2015/059697 filed 16 Dec. 2015, which claims priority to U.S. Application No. 62/092,627 filed 16 Dec. 2014, the contents of which are incorporated herein by reference in their entirety.

BACKGROUND

Isolated nucleic acids, particularly those that encode proteins, are attractive candidates for a variety of clinical applications. In particular RNAs that encode proteins, such as mRNAs, provide a number of potential advantages for clinical applications. For example, RNA can be transfected into cell in vivo, in vitro or ex vivo to induce expression of desired therapeutic or diagnostic proteins for treating or diagnosing disease. However, the potential of RNA therapeutics is limited by stability and half-life of the RNA as well as by the level of expression of the encoded protein.

Naturally occurring mRNAs contain a 5' cap structure which helps stabilize the RNA and is fundamental to eukaryotic gene expression (Shuman, S. et al Mol. Microbiol. 1995, 17, 405-410). These mRNAs also contain a 3' poly A tail. Both modification stabilize and improve translation of the encoded protein. The 5'-cap structure found at the 5' end of eukaryotic messenger RNAs (mRNAs) and many viral RNAs consists of a $N^7$-methylguanosine nucleoside linked to the 5'-terminal nucleoside of the pre-mRNA via a 5'-5' triphosphate linkage (Shatkin, A. J. Cell 1976, 2, 645-53; Shuman, S. Prog. Nucleic Acid Res. Mol. Biol. 2001, 66, 1-40; Decroly, E. et al PLoS Pathog. 2011, 7, e1002059). This cap structure fulfills many roles that ultimately lead to mRNA translation. RNA capping is also important for other processes, such as RNA splicing and export from the nucleus and to avoid recognition of mRNA by the cellular innate immunity machinery (Daffis, S. et al Nature 2010, 468, 452-6; Zist, R. et al Nat. Immunol. 2011, 12, 137-43). A number of synthetic cap analogs have been described. See, e.g., WO2009/149253, WO2011/015347.

Synthetic mRNAs are typically prepared by enzymatic synthesis using RNA polymerase and a DNA template followed by enzymatic addition of the 5'-cap and the 3'-end (Peyrane, F. et al Nucleic Acids Res. 2007, 35, e26). However, the process is expensive and difficult to control and therefore undesirable for commercial scale production.

Thus, a need exists for RNAs that are modified at the 5'-end, the 3'-end or the 5'-end and 3'-end that can be efficiently produced and that have improved expression of products (e.g., protein) encoded by the RNA, lower immunogenicity and/or improve stability.

SUMMARY OF THE INVENTION

This disclosure relates to nucleic acid molecules (e.g., RNA and DNA molecules) that contain modifications at the 5'-end, the 3'-end, or both the 5'-end and the 3-end. The nucleic acid molecule is preferably an RNA molecule that encodes a product, such as a polypeptide or nucleic acid, and more preferably is an mRNA including mRNAs encoding Cas9 proteins for CRISPR genome editing technologies and/or the 3'-end of an sgRNA (or crRNA and tracrRNA) for CRISPR genome editing technologies.

In one aspect, this disclosure relates to a compounds of Formula I and salts (preferably a pharmaceutically acceptable salt) thereof:

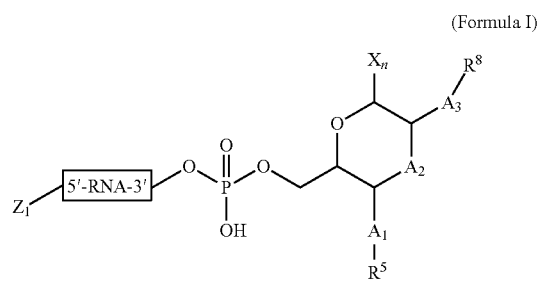

(Formula I)

wherein $Z_1$ is

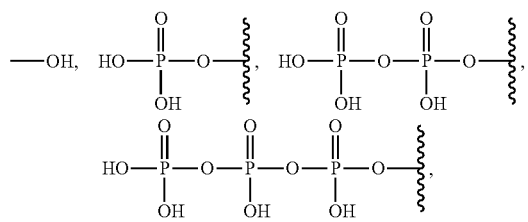

a cap 0, a cap 1,

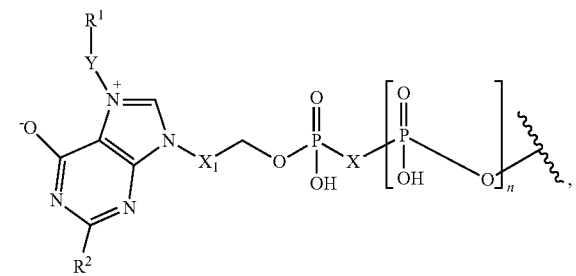

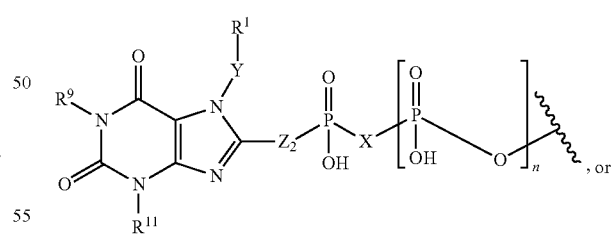

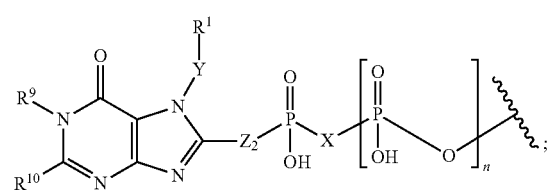

with the proviso that when $Z_1$ is

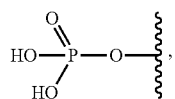

cap 0 or cap 1, -$A_1$-$R^5$ and -$A_3$-$R^8$ are not both —OH, or $A_2$ is not null;

$Z_2$ is null or a linking moiety, selected from the group consisting of —O—, —S—, optionally substituted lower alkyl, optionally substituted aminoalkyl, optionally substituted aryl, optionally substituted heteroaryl, optionally substituted cycloalkyl, optionally substituted cycloalkenyl, optionally substituted heterocyclyl,

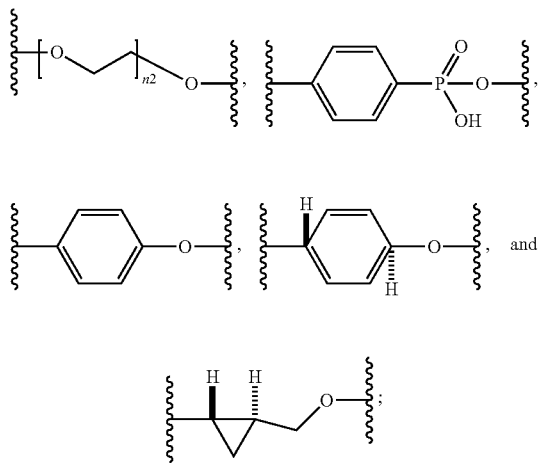

$A_1$ and $A_3$ are independently selected from the group consisting of null, NH, S, and O;

$A_2$ is null or selected from the group consisting of >$CR^6R^7$, >$NR^6$, >$NNR^6R^7$, >$NOR^6$, >S, and >O;

Y is null or a linking moiety selected from the group consisting of optionally substituted lower alkyl, optionally substituted alkenyl, optionally substituted alkynyl, —(CH$_2$)$_n$OR$^{15}$, —(CH$_2$)$_n$COOR$^{15}$, and —(CH$_2$)$_n$C(O)NR$^2$;

$R^1$ is selected from the group consisting of H, optionally substituted cycloalkyl, optionally substituted cycloalkenyl, optionally substituted aryl, optionally substituted heteroaryl, and optionally substituted heterocyclyl;

$R^2$ is selected from the group consisting of H, —OH, optionally substituted alkyl, —C(O)NR$^{12}$R$^{13}$ and —NR$^{12}$R$^{13}$;

$R^5$, $R^6$, and $R^8$ are independently selected from the group consisting of H, optionally substituted alkyl, polyamine, PEGs, —(CH$_2$)$_{n1}$NR$^{12}$R$^{13}$, —(CH$_2$)$_{n1}$NR$^{14}$C(O)R$^{15}$, —(CH$_2$)$_{n1}$OR$^{15}$, —(CH$_2$)$_{n1}$C(O)OR$^{15}$, —(CH$_2$)$_{n1}$C(O)R$^5$, —(CH$_2$)$_{n1}$C(O)NR$^{12}$R$^{13}$, —O—(CH$_2$)$_{n3}$—C(O)—(NR$^{12}$)$_2$—C(O)—X$_2$, —O—(CH$_2$)$_{n3}$—C(O)—[NR$^{12}$—C(O)—(CH$_2$)$_{n3}$]$_{1-3}$—X$_2$, or $R^6$ and $R^8$ together form a ring that is optionally substituted and contains 10-80 ring atoms in which 10-40 ring atoms can be hetero atoms, or $R^6$ and $R^7$ together form a 3-8 membered ring that is optionally substituted and in which 1 to 6 ring atoms can be hetero atoms;

$R^7$, $R^{11}$, $R^{12}$, $R^{13}$, $R^{14}$, $R^{15}$ and $R^{16}$ are independently selected from the group consisting of H, optionally substituted lower alkyl, and optionally substituted acyl;

$R^9$ is selected from the group consisting of H and optionally substituted lower alkyl;

$R^{10}$ is selected from the group consisting of H, —NR$^{12}$R$^{13}$, and —OR$^{16}$; n is 1 to 4;

n1 is zero to 10;

n2 is 1 to 12;

n3 is 1 to 8;

X is selected from the group consisting of O, S, NH, and optionally substituted alkanediyl;

$X_1$ is selected form the group consisting of

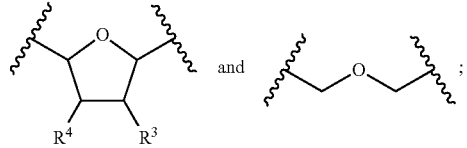

$R^3$ and $R^4$ are independently selected from the group consisting of H and —OR$^{16}$, or $R^3$ and $R^4$ together form O-Q-O;

Q is selected from the group consisting of —CH$_2$— and —C(Me)$_2$-;

$X_2$ is selected from the group consisting of affinity moiety and detection moiety, and $X_n$ is a nucleobase.

In some aspect, the compound of Formula I is modified at both the 5'-end and 3'-end and is a compound of Formulas II, III, IV, or a salt (preferably a pharmaceutically acceptable salt) thereof, Formula II Formula III

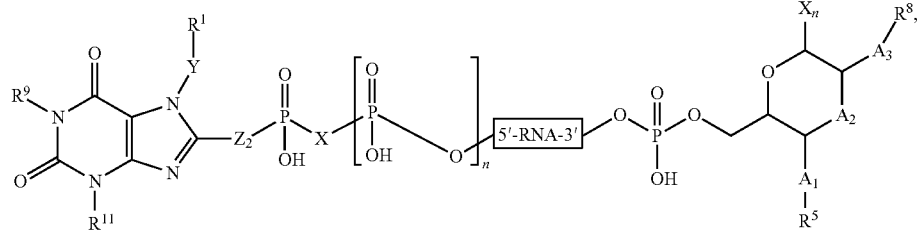

Formula IV

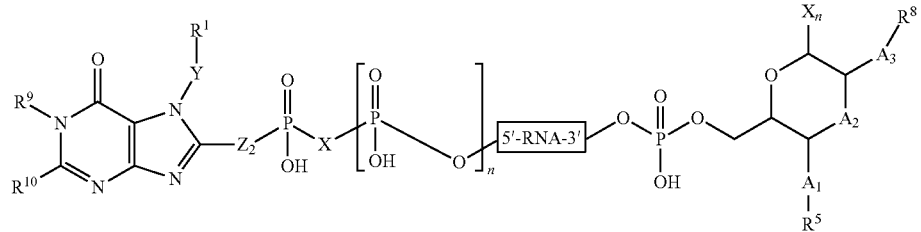

The variables in Formulas II, III and IV are as defined in Formula I, with the proviso that -A$_1$-R$^5$ and -A$_3$-R$^8$ are not both —OH, or A$_2$ is not null. In some embodiments, the compound is of Formula II, III or IV, with the proviso that that -A$_1$-R$^5$ and -A$_3$-R$^8$ are not both —OH, or A$_2$ is not null.

In other aspects, the compounds of Formula I is modified at the 5'-end and unmodified at 3'-end, and is a compound of Formula VI, Formula VII, Formula VIII, or a salt (preferably a pharmaceutically acceptable salt) thereof, The variables in Formulas VI, VII and VIII are as defined in Formula I, with the proviso that -A$_1$-R$^5$ and -A$_3$-R$^8$ are both —OH, and A$_2$ is null.

In certain preferred embodiments the compound is of any of Formulas I-IV and VI-VIII, wherein Y is an alkyl linking moiety, preferably a lower alkyl linking moiety such as (—CH$_2$—); and R$^1$ is a substituted aryl or substituted heteroaryl, for example aryl substituted with phenyl or Formula VI

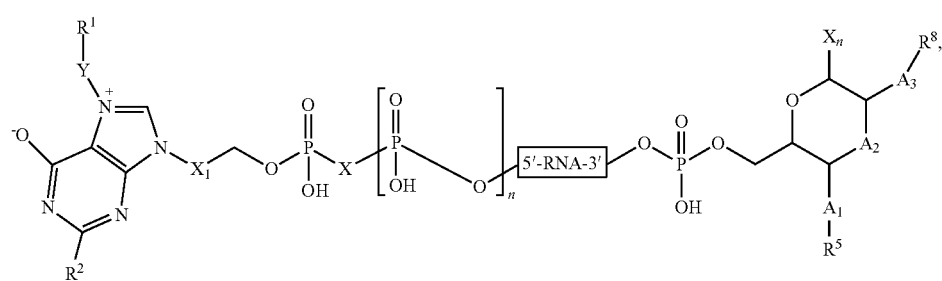

Formula VII

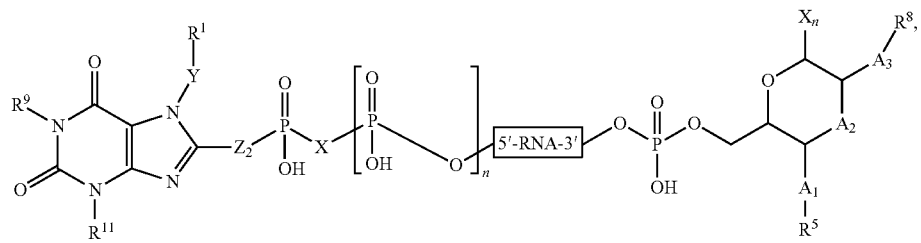

Formula VIII

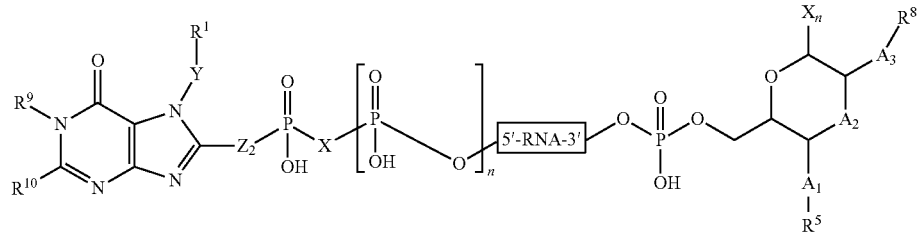

heteroaryl substituted with phenyl. In particularly preferred embodiments, —Y—R$^1$ can be

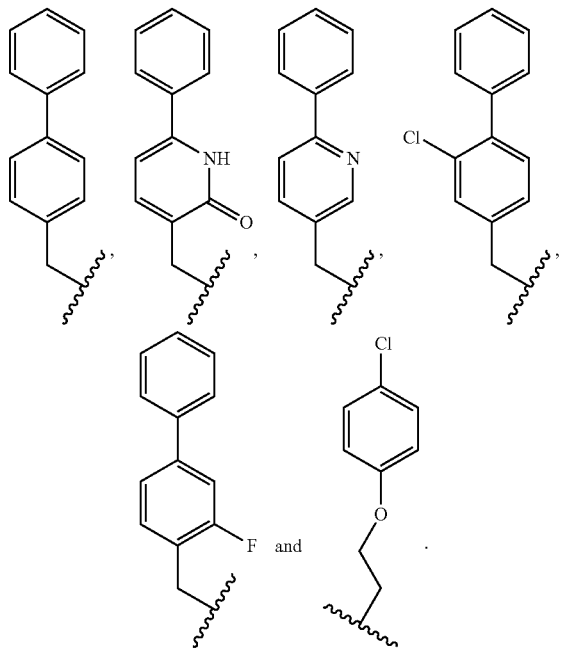

In other aspects, the compounds of Formula I is modified at the 3'-end and unmodified at 5'-end, and is a compound of Formula V or a salt (preferably a pharmaceutically acceptable salt) thereof Formula V

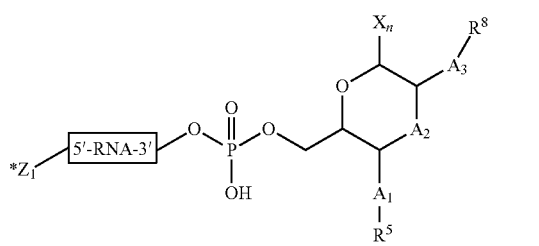

In Formula V, *Z$_1$ is selected from a group consisting of

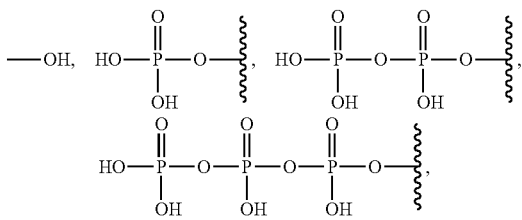

a cap 0 and a cap 1, and the other variables are as described in Formula I, with the proviso that A$_2$ id not null, or -A$_1$-R$^5$ and -A$_3$-R$^8$ are not both —OH.

The compounds of Formulas I-VIII contain a nucleobase, X$_n$, which can be any desired nucleobase, such as adenine, guanine, cytosine, uracil or a modified nucleobase such as pseudouracil. A preferred nucleobase is adenine.

The RNA in compounds of Formulas I-VIII can be any desired RNA molecule, but preferable encodes a product, such as a protein.

In other aspects, the disclosure relates to guanosine or purine derivatives that can be used to prepare 5'-end modified nucleic acids (e.g., RNAs) disclosed herein. In particular aspects, the disclosure relates to a compound of Formula IX, X, XI or salt (pharmaceutically acceptable salt) thereof:

Formula IX

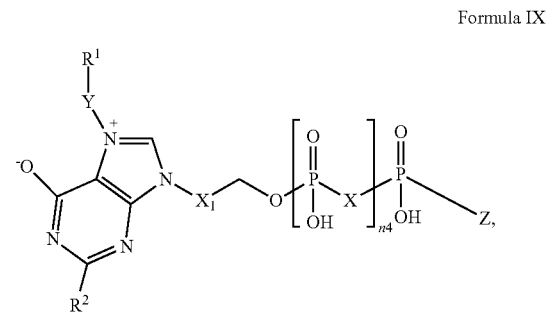

Formula X

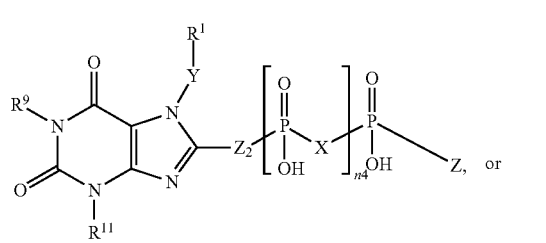

Formula XI

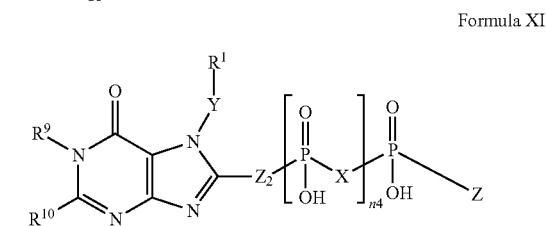

In each of Formulas IX, X and XI,
Z is selected from a group consisting of

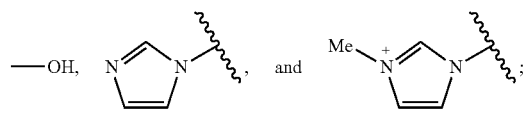

n4 is 0-2; and the other variables are as defined in Formula I. In certain preferred embodiments of this aspect, Y is an alkyl linking moiety, preferably a lower alkyl linking moiety such as (—CH$_2$—); and R$^1$ is a substituted aryl or substituted heteroaryl, for example aryl substituted with phenyl or heteroaryl substituted with phenyl. In particularly preferred embodiments —Y—R$^1$ can be

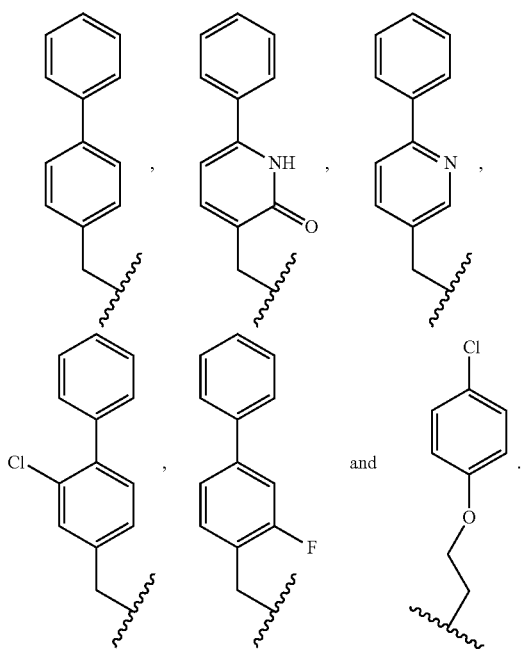

The invention also relates to methods of using and making the compounds disclosed herein.

DETAILED DESCRIPTION OF THE INVENTION

Figure 1:
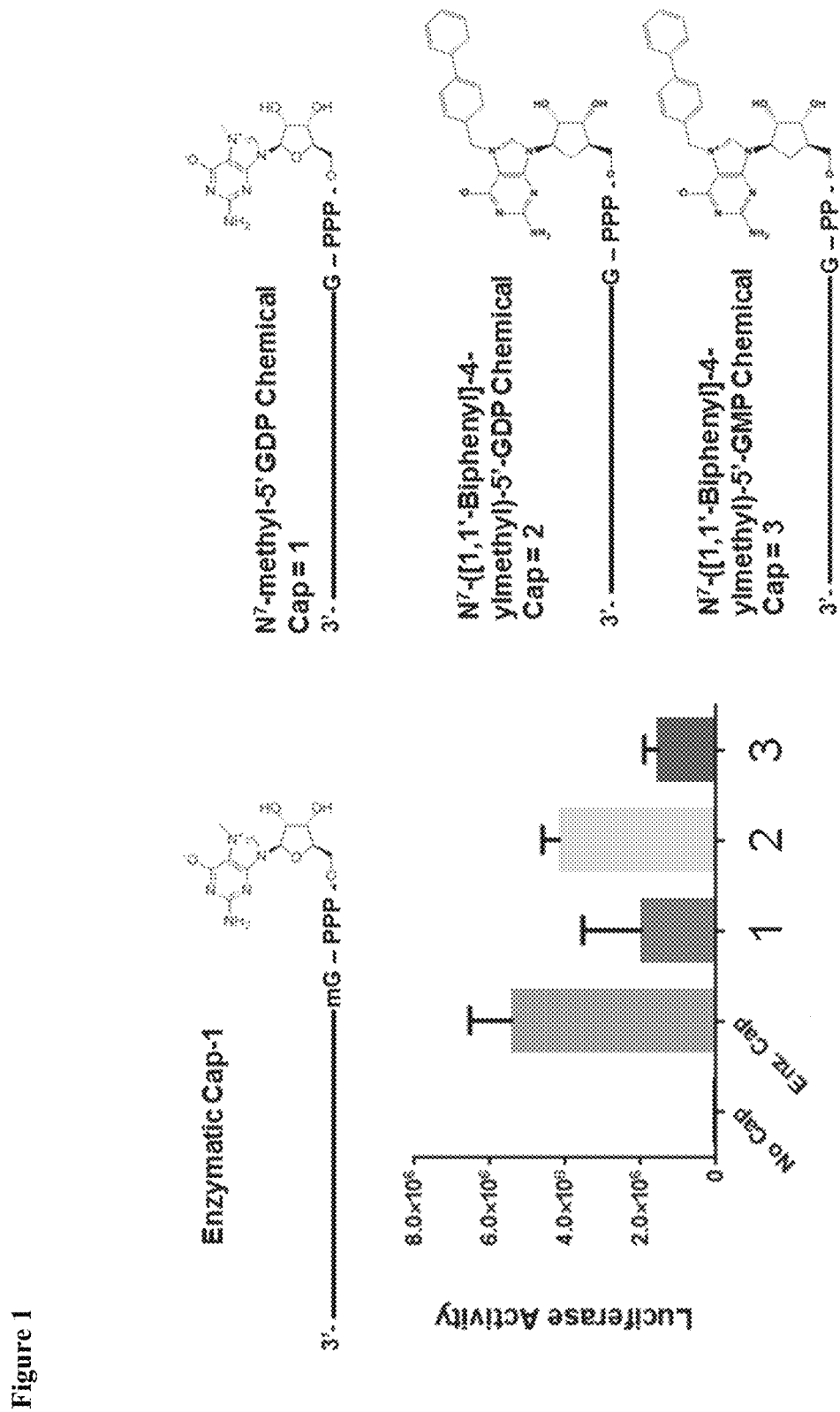
FIG. 1 is a bar graph and corresponding capped mRNAs depicting luciferase activity of enzymatically capped HPLC purified mRNA (Cap-1) compared to HPLC purified chemically capped mRNAs 1, 2, and 3.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meaning as commonly understood by one of ordinary skill in the art.

This disclosure relates to nucleic acid molecules (e.g., RNA and DNA molecules) that contain modifications at the 5'-end, the 3'-end, or both the 5'-end and the 3-end. The nucleic acid molecule is preferably an RNA molecule that encodes a product, such as a polypeptide or nucleic acid, and more preferably is an mRNA. The RNA or mRNA that is modified as disclosed herein can be produced using any desired method, such enzymatic or chemical synthesis. The 5'-end modification comprise cap structures based on guanosine or purine that increase expression of products (e.g., protein) encoded by the RNA, lower immunogenicity and/or improve stability of the RNA. The 3'-end modifications comprise modification of the cis-diol at the 3' and 2' positions of the terminal ribose of the RNA, for example by inserting a ring atom between these positions or replacing one or both hydroxyl groups with other substituents, to increase expression of products (e.g., protein) encoded by the RNA and/or improve stability of the RNA (e.g., by slowing the rate of degradation). If desired, the 3'-end modification can include a variety of functional moieties, such as an affinity moiety or a detection moiety. Compounds that contain such moieties are particularly useful for, for example, imaging, biochemical analysis and bioconjugation.

As described and exemplified herein, RNAs have been prepared that contain the 5'-end cap structures based on guanosine or purine that are disclosed herein. These modified RNAs were shown to bind to eIF4E and to be translated in cells. 3'-end RNAs were also prepared and had increased half-life and expression in comparison to unmodified RNA.

In one aspect, this disclosure relates to RNA molecules that contain a 5'-end cap structure, a 3'-end modification, or a 5'-end cap structure and a 3'-end modification. Such RNA molecules are compounds of Formula I and salts (preferably pharmaceutically acceptable salts) thereof:

(Formula I)

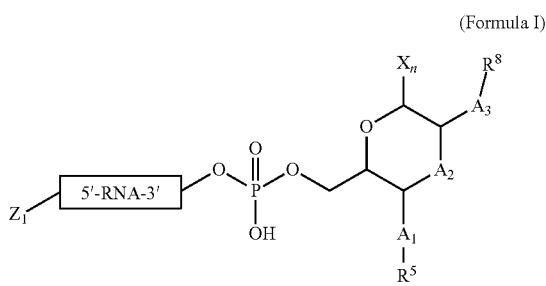

wherein
$Z_1$ is

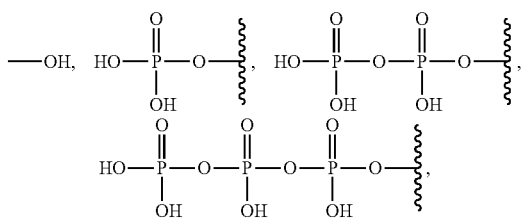

a cap 0, a cap 1,

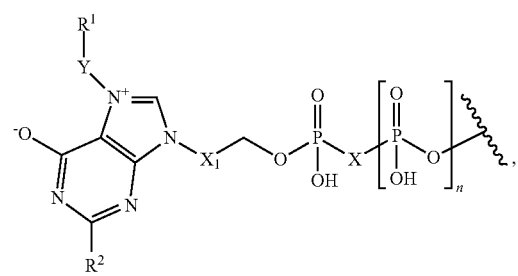

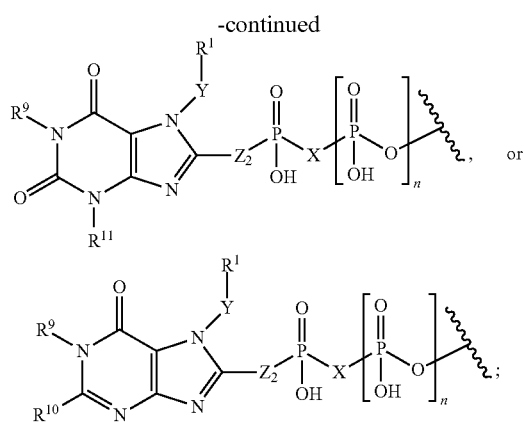

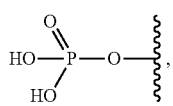

with the proviso that when $Z_1$ is cap 0 or cap 1, -$A_1$-$R^5$ and -$A_3$-$R^8$ are not both —OH, or $A_2$ is not null;

$Z_2$ is null or a linking moiety, selected from the group consisting of —O—, —S—, optionally substituted lower alkyl, optionally substituted aminoalkyl, optionally substituted aryl, optionally substituted heteroaryl, optionally substituted cycloalkyl, optionally substituted cycloalkenyl, optionally substituted heterocyclyl,

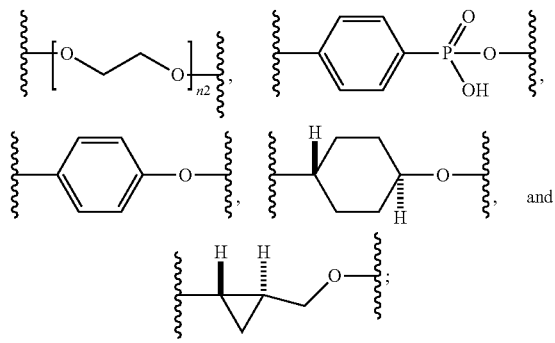

$A_1$ and $A_3$ are independently selected from the group consisting of null, NH, S, and O;

$A_2$ is null or selected from the group consisting of >$CR^6R^7$, >$NR^6$, >$NNR^6R^7$, >$NOR^6$, >S, and >O;

Y is null or a linking moiety selected from the group consisting of optionally substituted lower alkyl, optionally substituted alkenyl, optionally substituted alkynyl, —$(CH_2)_nOR^{15}$, —$(CH_2)_nCOOR^{15}$, and —$(CH_2)_nC(O)NR^{12}$;

$R^1$ is selected from the group consisting of H, optionally substituted cycloalkyl, optionally substituted cycloalkenyl, optionally substituted aryl, optionally substituted heteroaryl, and optionally substituted heterocyclyl;

$R^2$ is selected from the group consisting of H, —OH, optionally substituted alkyl, —$C(O)NR^{12}R^{13}$ and —$NR^{12}R^{13}$;

$R^5$, $R^6$, and $R^8$ are independently selected from the group consisting of H, optionally substituted alkyl, polyamine, PEGs, —$(CH_2)_{n1}NR^{12}R^{13}$, —$(CH_2)_{n1}NR^{14}C(O)R^{15}$, —$(CH_2)_{n1}OR^{15}$, —$(CH_2)_{n1}C(O)OR^{15}$, —$(CH_2)_{n1}C(O)R^{15}$, —$(CH_2)_{n1}C(O)NR^{12}R^{13}$, —O—$(CH_2)_{n3}$—C(O)—$(NR^{12})_2$—C(O)—$X_2$, —O—$(CH_2)_{n3}$—C(O)—[$NR^{12}$C(O)—$(CH_2)_{n3}]_{1-3}$—$X_2$, or $R^6$ and $R^8$ together form a ring that is optionally substituted and contains 10-80 ring atoms in which 10-40 ring atoms can be hetero atoms, or $R^6$ and $R^7$ together form a 3-8 membered ring that is optionally substituted and in which 1 to 6 ring atoms can be hetero atoms;

$R^7$, $R^{11}$, $R^{12}$, $R^{13}$, $R^{14}$, $R^{15}$ and $R^{16}$ are independently selected from the group consisting of H, optionally substituted lower alkyl, and optionally substituted acyl;

$R^9$ is selected from the group consisting of H and optionally substituted lower alkyl;

$R^{10}$ is selected from the group consisting of H, —$NR^{12}R^{13}$, and —$OR^{16}$;

n is 1 to 4;
n1 is zero to 10;
n2 is 1 to 12;
n3 is 1 to 8;

X is selected from the group consisting of O, S, NH, and optionally substituted alkanediyl;

$X_1$ is selected form the group consisting of

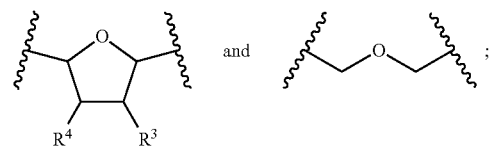

$R^3$ and $R^4$ are independently selected from the group consisting of H and —$OR^{16}$, or $R^3$ and $R^4$ together form O-Q-O;

Q is selected from the group consisting of —$CH_2$— and —$C(Me)_2$-;

$X_2$ is selected from the group consisting of affinity moiety and detection moiety, and $X_n$ is a nucleobase.

In certain preferred embodiments the compound is of Formula I, wherein
$Z_1$ is

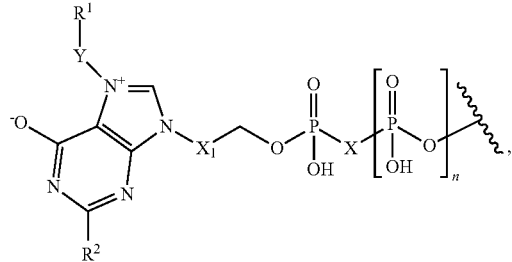

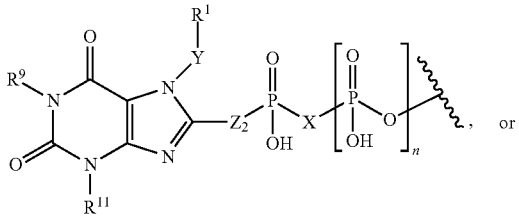

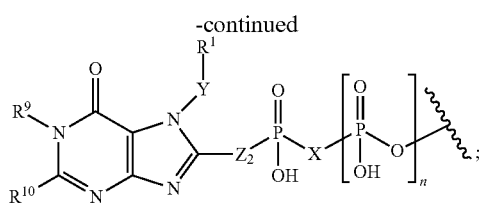

Y is an alkyl linking moiety, preferably a lower alkyl linking moiety such as (—CH$_2$—); and R$^1$ is a substituted aryl or substituted heteroaryl, for example aryl substituted with phenyl or heteroaryl substituted with phenyl. In particularly preferred embodiments —Y—R$^1$ can be

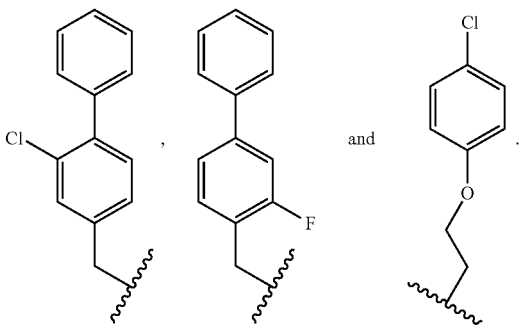

In other preferred embodiments the compound is of Formula I, wherein -A$_1$-R$^5$ and -A$_3$-R$^8$ are not both —OH, or A$_2$ is not null. In another preferred embodiment, -A$_1$-R$^5$ and -A$_3$-R$^8$ are not both —OH, and A$_2$ is not null.

In some aspect, the compound of Formula I is modified at both the 5'-end and 3'-end and is a compound of Formulas II, III or IV, or a salt thereof,

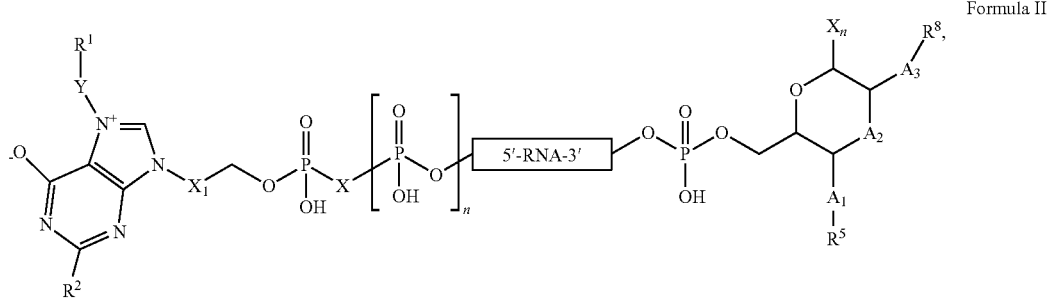

Formula II

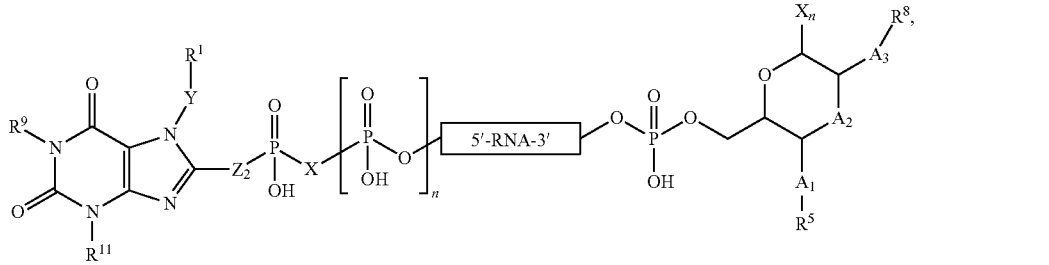

Formula III

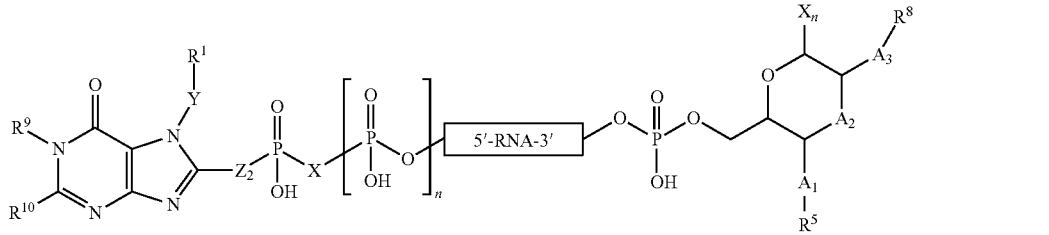

Formula IV

The variables in Formulas II, III and IV are as defined in Formula I, with the proviso that -$A_1$-$R^5$ and -$A_3$-$R^8$ are not both —OH, or $A_2$ is not null. In some embodiments, the compound is of Formula II, III or IV, with the proviso that that -$A_1$-$R^5$ and -$A_3$-$R^8$ are not both —OH, or $A_2$ is not null.

In certain preferred embodiments of this aspect, Y is an alkyl linking moiety, preferably a lower alkyl linking moiety such as (—$CH_2$—); and $R^1$ is a substituted aryl or substituted heteroaryl, for example aryl substituted with phenyl or heteroaryl substituted with phenyl. In particularly preferred embodiments, —Y—$R^1$ can be

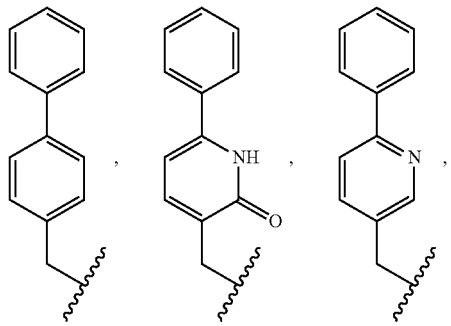

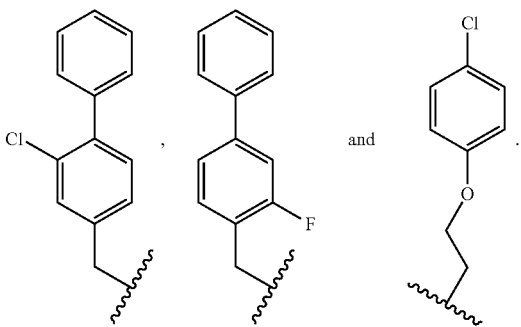

In other aspects, the compounds of Formula I is modified at the 5'-end and unmodified at 3'-end, and is a compound of Formula VI, Formula VII, Formula VIII, or a salt thereof, Formula VI

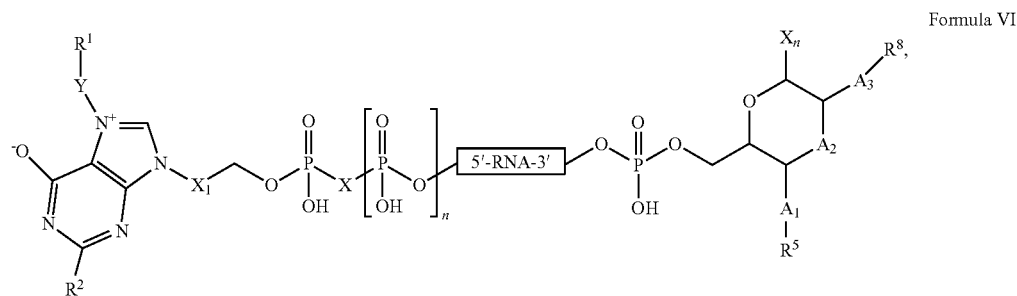

Formula VII

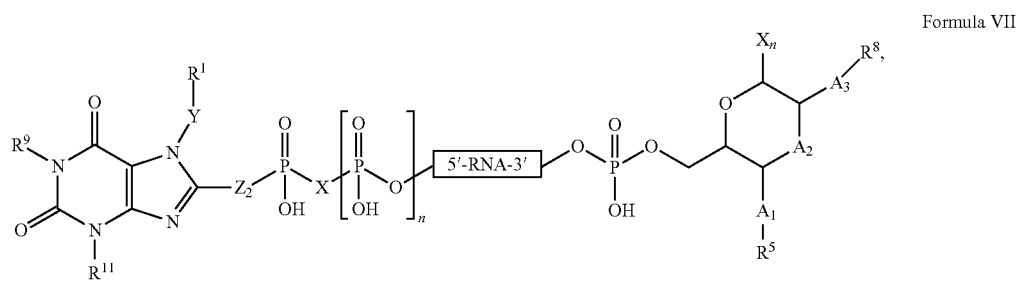

Formula VIII

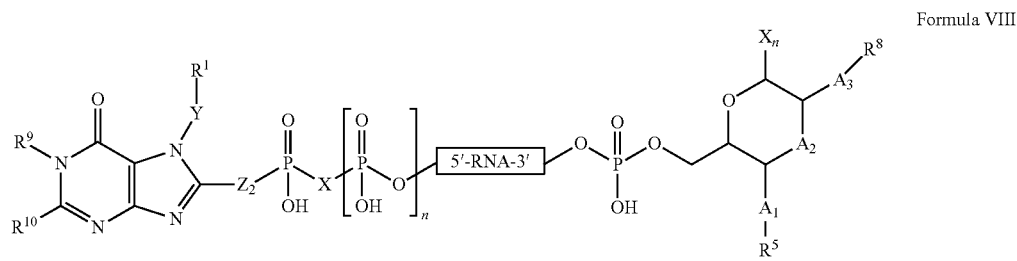

The variables in Formulas VI, VII and VIII are as defined in Formula I, with the proviso that -$A_1$-$R^5$ and -$A_3$-$R^8$ are both —OH, and $A_2$ is null. In certain preferred embodiments of this aspect, Y is an alkyl linking moiety, preferably a lower alkyl linking moiety such as (—$CH_2$—); and $R^1$ is a substituted aryl or substituted heteroaryl, for example aryl substituted with phenyl or heteroaryl substituted with phenyl. In particularly preferred embodiments, —Y—$R^1$ can be

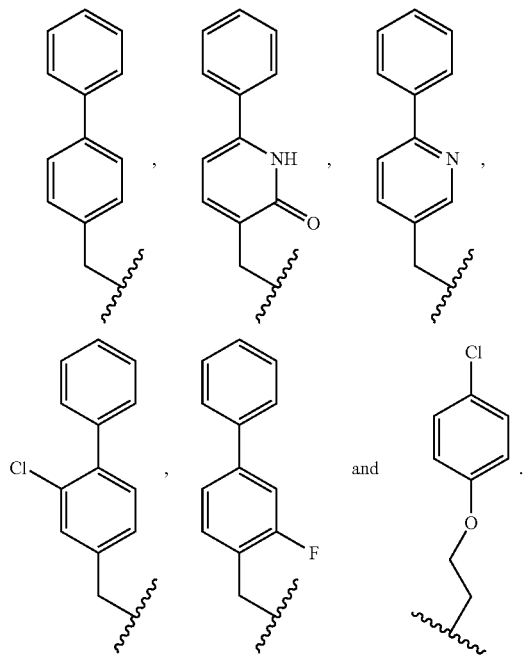

In other aspects, the compounds of Formula I is modified at the 3'-end and unmodified at 5'-end, and is a compound of Formula V or a salt thereof Formula V

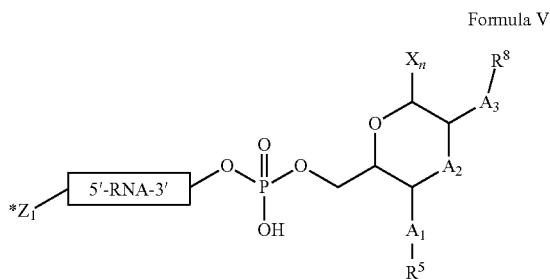

In Formula V, *$Z_1$ is selected from a group consisting of

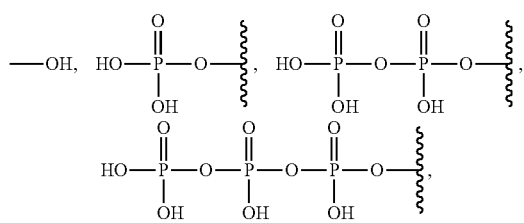

a cap 0 and a cap 1, and the other variables are as described in Formula I, with the proviso that $A_2$ is not null, or -$A_1$-$R^5$ and -$A_3$-$R^8$ are not both —OH.

The compounds of Formulas I-VIII contain a nucleobase, $X_n$, which can be any desired nucleobase, such as adenine, guanine, cytosine, uracil or a modified nucleobase such as pseudouracil. A preferred nucleobase is adenine.

The RNA in compounds of Formulas I-VIII can be any desired RNA molecule, but preferable encodes a product, such as a protein. Suitable proteins include therapeutic proteins, such as antibodies or antigen-binding fragments thereof, receptors, cytokines and growth factors; antigens, such as those from pathogens or tumor cells. The RNA, e.g., mRNA, may contain a ribose-phosphate backbone with the common nucleobases adenine, cytosine, guanine and uracil bonded to the 1" position of the ribose ring. If desired, one or more modified bases may be included in the RNA to the desired degree. For example, between 0.1% and 100% of the nucleobases can be a modified base, such as pseudouracil. If desired, the RNA molecule can contain one or more phosphoramidate, phosphorothioate, methylphosphonate, phosphoroselenoate or other suitable linkages.

In other aspects, the disclosure relates to guanosine or purine derivatives that can be used to prepare 5'-end modified nucleic acids (e.g., RNAs) disclosed herein.

In particular aspects, the disclosure relates to a compound of Formula IX, X, XI or salt (pharmaceutically acceptable salt) thereof:

Formula IX

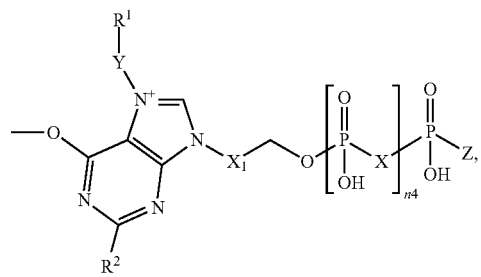

Formula X

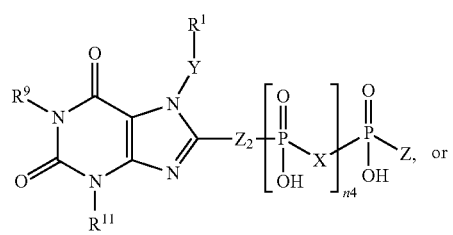

Formula XI

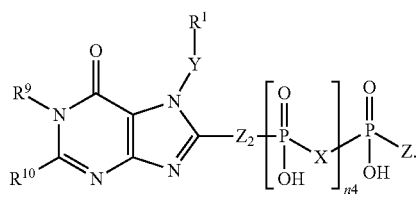

In each of Formulas IX, X and XI,
Z is selected from a group consisting of

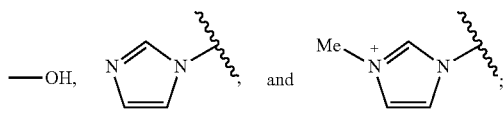

n4 is 0-2; and the other variables are as defined in Formula I. In certain preferred embodiments of this aspect, Y is an alkyl linking moiety, preferably a lower alkyl linking moiety such as (—$CH_2$—); and $R^1$ is a substituted aryl or substituted heteroaryl, for example aryl substituted with phenyl or heteroaryl substituted with phenyl. In particularly preferred embodiments, —Y—$R^1$ can be

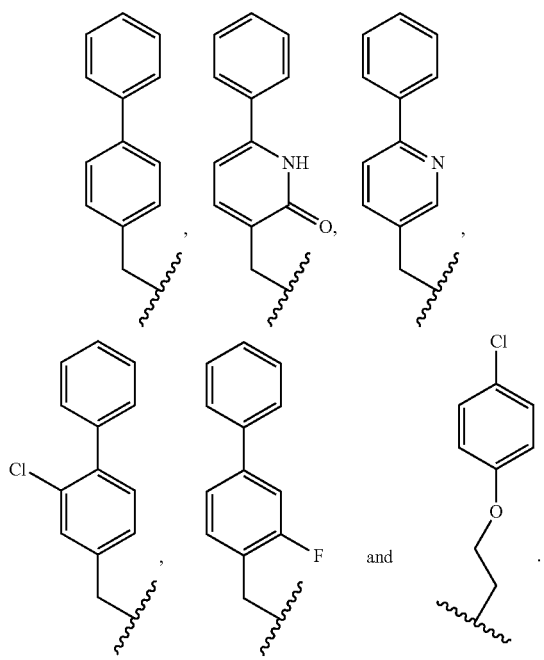

In preferred compounds of Formula IX, $R^2$ is preferably optionally substituted amino; X is preferably O; and/or $X_1$ is preferably

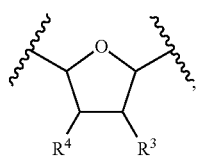

wherein $R^3$ and $R^4$ are as defined in Formula I.

Method of Using End Capped Nucleic Acids

The end capped nucleic acids disclosed herein can be used for a variety of purposes, including to induce the production of a desired protein by a cell for diagnostic or therapeutic purposes. For example, an end capped mRNA that encodes a protein can be transfected into a cell in vivo or in vitro. Suitable methods for transfection of mRNAs are well known in the art and include, for example, methods that use cationic polymers, calcium phosphate or cationic lipids to facilitate transfection, as well as direct injection, biolistic particle delivery, electroporation, laser irradiation, sonoporation and magnetic nanoparticle methods. See, e.g., Kim et al, *Anal Bioanal Chem.* 397:3173-3178 (2010).

The cell to be transfected is preferably an animal cell, such as from a mammal, a fish, a bird and more preferably a human. Suitable animal subjects include, for example, cattle, pigs, horses, deer, sheep, goats, bison, rabbits, cats, dogs, chickens, ducks, turkeys, and the like.

End capped RNA molecules of the invention can also be delivered to cells ex vivo, such as cells explanted from an individual patient (e.g., lymphocytes, bone marrow aspirates, tissue biopsy), followed by re-implantation of the cells into a patient, usually after selection for cells which have been transfected with the end capped RNA molecule. The appropriate amount of cells to deliver to a patient will vary with patient conditions, and desired effect, which can be determined by a skilled artisan. Preferably, the cells used are autologous, i.e., cells obtained from the patient being treated.

The end capped nucleic acids (e.g., mRNAs) can be used in the genome editing technology known as CRISPRs (clustered regularly interspaced short palindromic repeats) which are part of bacterial anti-viral defence systems and which can be used to induce targeted genome editing in eukaryotic cells. When used as a tool for genome editing the type II CRISPR system is typically composed of 2 or 3 components: the Cas9 protein which is an RNA dependent DNA endonuclease and either one or 2 RNAs per DNA strand cleavage site (the natural 2 RNA system includes a CRISPR-RNA (crRNA) and a trans-activating RNA (tracrRNA) while in the single RNA system the 2 crRNA and tracrRNA have been re-engineered into a single functional transcript called a single guide RNA (sgRNA)). A standard system for CRISPR editing can encode the sgRNA or multiple RNAs and the Cas9 protein in a lentiviral vector. However a challenge with viral vectors is that there is a limit to the size of additional genes that can be encoded by them and the large Cas9 proteins whose size ranges from ~1000-2000 amino acids in length can be difficult to encode in viral vectors. An all RNA CRISPR system using an in vitro transcribed Cas9 mRNA co-formulated with an in vitro transcribed sgRNA (or cr RNA+tracrRNA) could be co-formulated for transfection into cells in vivo, in vitro or ex vivo in order to specifically edit the genomes of the transfected cells. The end capped mRNAs disclosed herein are well suited for this application.

End capped nucleic acids can also be used for a variety of biochemical and analytical purposes. For example, the end capped nucleic acids can be used for imaging studies, to study the metabolism of RNA and to study the interaction of RNA with other biomolecules.

Synthetic Schemes

The compounds of the present invention may be prepared by the routes described in the following Schemes or Examples.

Scheme 1:

Chemically capped mRNA of the general structure I, as defined in Formula VI can be obtained by reacting mRNA-5'-monophosphate with imidazole activated cap structures of the general structure II in a suitably buffered aqueous saline solution (buffers: HEPES, TRIS, MES, PBS) at a suitable pH, ranging from 5.5-7.5, in presence or absence of organic solvents, such as DMF and DMSO, in the presence of a suitable Lewis-acidic activator such as $MnCl_2$, $NiCl_2$, $ZnCl_2$.

Scheme 1

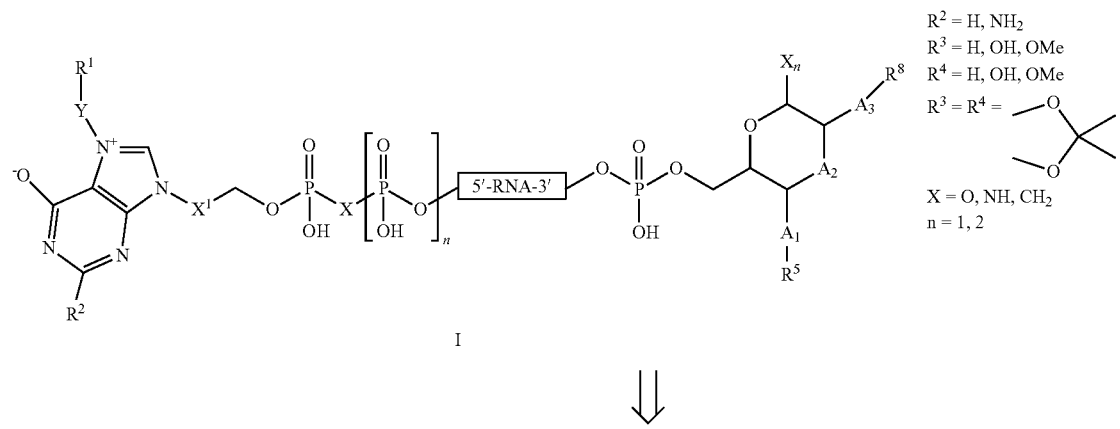

I

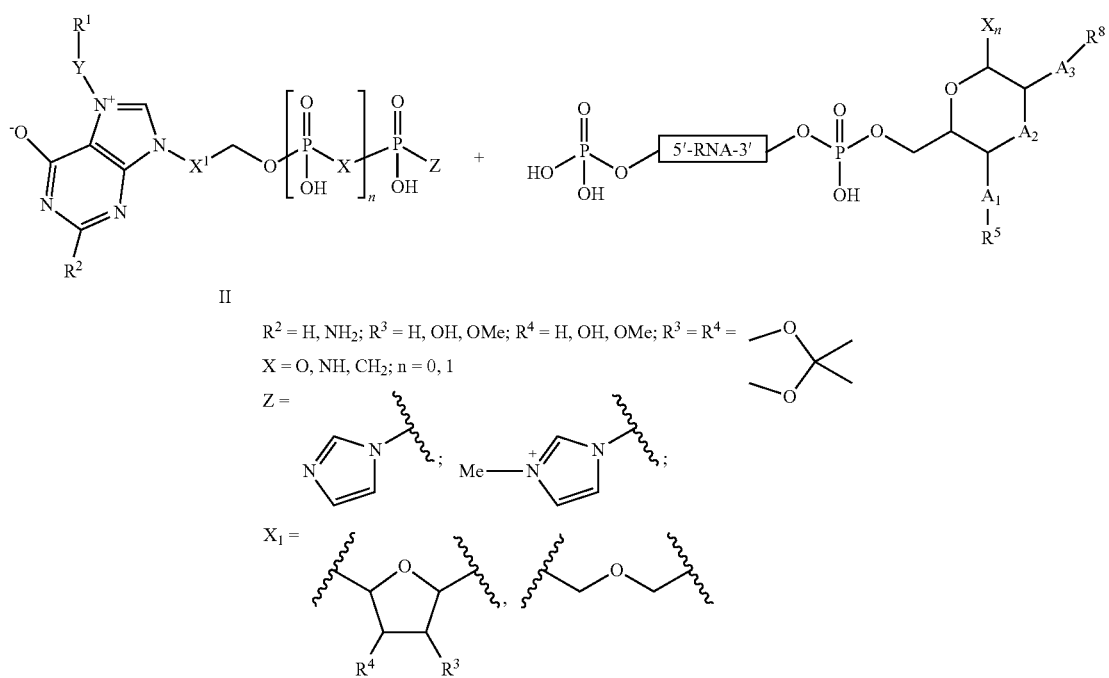

Scheme 2:

Compounds of the general structure II, where Y and R in Formula I, can be prepared from by treatment of phosphates III (tributylammonium salts) with imidazole or N-methylimidazole, a suitable tertiary phosphine, such as triphenylphosphine, a suitable oxidant, such as 2,2'-dipyridyldissulfide, and a suitable base, such as triethylamine in a suitable solvent, such as DMF, DMSO, NMP, trimethylphosphate at a suitable temperature, such as room temperature (a) M. Lewdorowicz, Y. Yoffe, J. Zuberek, J. Jemielity, J. Stepinski, R. Kierzek, R. Stolarski, M. Shapira, E. Darzynkiewicz, *RNA* 2004, 10, 1469; b) R. Worch, J. Stepinski, A. Niedzwiecka, M. Jankowska-Anyszka, C. Mazza, S. Cusack, R. Stolarski, E. Darzynkiewicz, *Nucleosides Nucleotides and Nucleic Acids* 2005, 24, 1131; c) M. Warminski, J. Kowalska, J. Buck, J. Zuberek, M. Lukaszewicz, C. Nicola, A. N. Kuhn, U. Sahin, E. Darzynkiewicz, J. Jemielity, *Bioorg. Med. Chem.*, 2013, 23, 3753).

Scheme 2

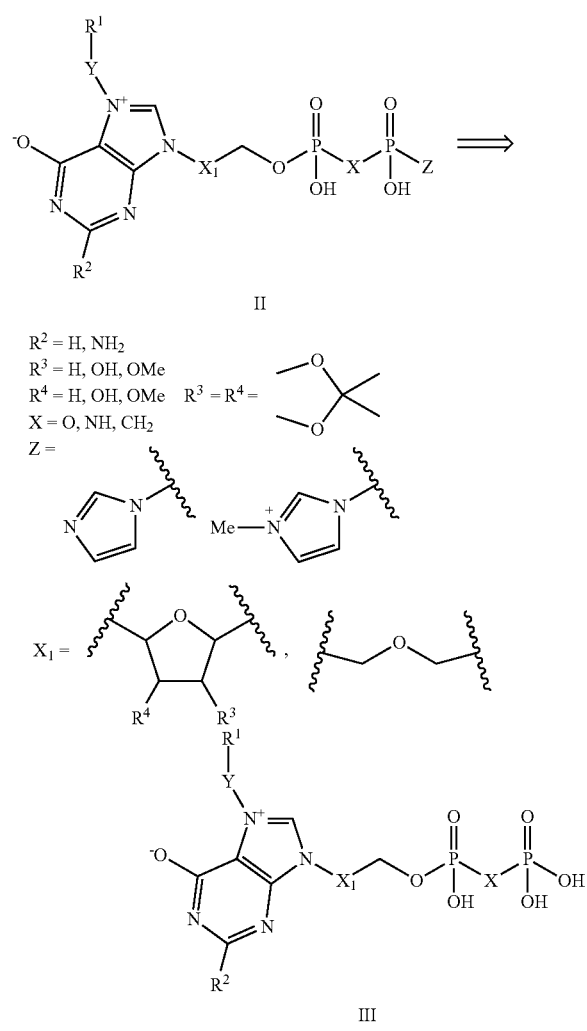

Scheme 3:

Compounds of the general structure III, where Y and R¹ are defined as in Formula I, can be prepared by reaction of activated phosphates IV with triethylammonium phosphate, or a similar phosphate salt, in a suitable solvent such as DMF, DMSO, or water in the presence of a lewis acid such as zinc chloride, magnesium chloride or manganese chloride at a suitable temperature such as room temperature (a) M. Lewdorowicz, Y. Yoffe, J. Zuberek, J. Jemielity, J. Stepinski, R. Kierzek, R. Stolarski, M. Shapira, E. Darzynkiewicz, *RNA* 2004, 10, 1469; b) R. Worch, J. Stepinski, A. Niedzwiecka, M. Jankowska-Anyszka, C. Mazza, S. Cusack, R. Stolarski, E. Darzynkiewicz, *Nucleosides Nucleotides and Nucleic Acids* 2005, 24, 1131; c) M. Warminski, J. Kowalska, J. Buck, J. Zuberek, M. Lukaszewicz, C. Nicola, A. N. Kuhn, U. Sahin, E. Darzynkiewicz, J. Jemielity, *Bioorg. Med. Chem.*, 2013, 23, 3753).

Compounds of the general structure III, where Y and R¹ are defined as in Formula I, can be prepared by alkylation of V using a suitable alkylation reagent, such as an alkyl halide, triflate, or mesylate in a suitable solvent such as DMF, DMSO, or NMP at a suitable reaction temperature ranging from room temperature to 60° C.

When X=O, compounds of the general structure III, where Y and R¹ are defined as in Formula I, can also be prepared by reaction of VI with diphosphoric acid tetrachloride in a suitable solvent such as trimethylphosphate at a suitable temperature ranging from 0° C. to room temperature (J. Emsley, J. Moore, P. B. Udy, *J. Chem. Soc.* (*A*) *Inorg. Phys. Theor.* 1971, 2863).

When X=NH, compounds of the general structure III, where Y and R¹ are defined as in Formula I, can also be prepared by reaction of IV with imido-bis(phosphoryldichloride) in a suitable solvent such as trimethylphosphate at a suitable temperature ranging from 0° C. to room temperature (A. M. Rydzik, M. Kulis, M. Lukaszewicz, J. Kowalska, J. Zuberek, Z. M. Darzynkiewicz, E. Darzynkiewicz, J. Jemielity, *Bioorganic & Med. Chem.* 2012, 20, 1699).

When X=CH₂, compounds of the general structure III, where Y and R¹ are defined as in Formula I, can also be prepared by reaction of IV with methylenebis(phosphonic dichloride) in a suitable solvent such as trimethylphosphate at a suitable temperature such as 0° C. or room temperature (a) M. Honcharenko, M. Zytek, B. Bestas, P. Moreno, J. Jemielity, E. Darzynkiewicz, C. I. E. Smith, R. Stroemberg, *Bioorg. Med. Chem.*, 2013, 21, 7921; b) M. Kalek, J. Jemielity, Z. M. Darzynkiewicz, E. Bojarska, J. Stepinski, R. Stolarski, R. E. Davis, E. Darzynkiewic, *Bioorg. Med. Chem.* 2006, 14, 3223; c) M. Kalek, J. Jemielity, J. Stepinski, R. Stolarski, E. Darzynkiewics, *Tetrahedron Lett.* 2005, 46, 2417).

Scheme 3

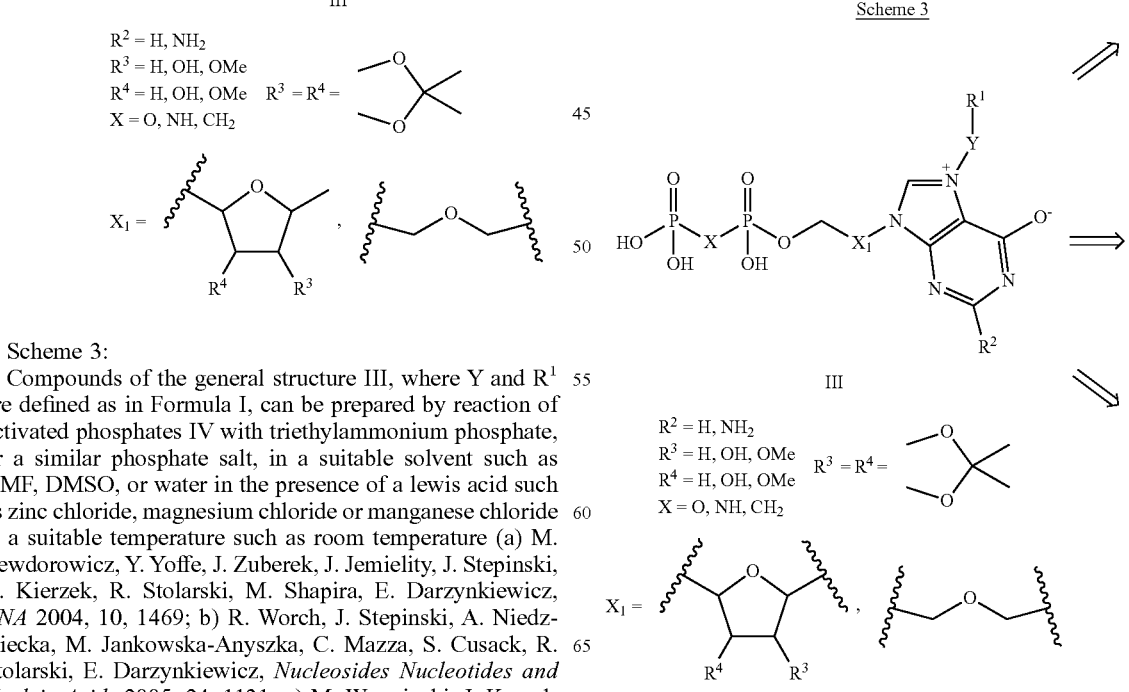

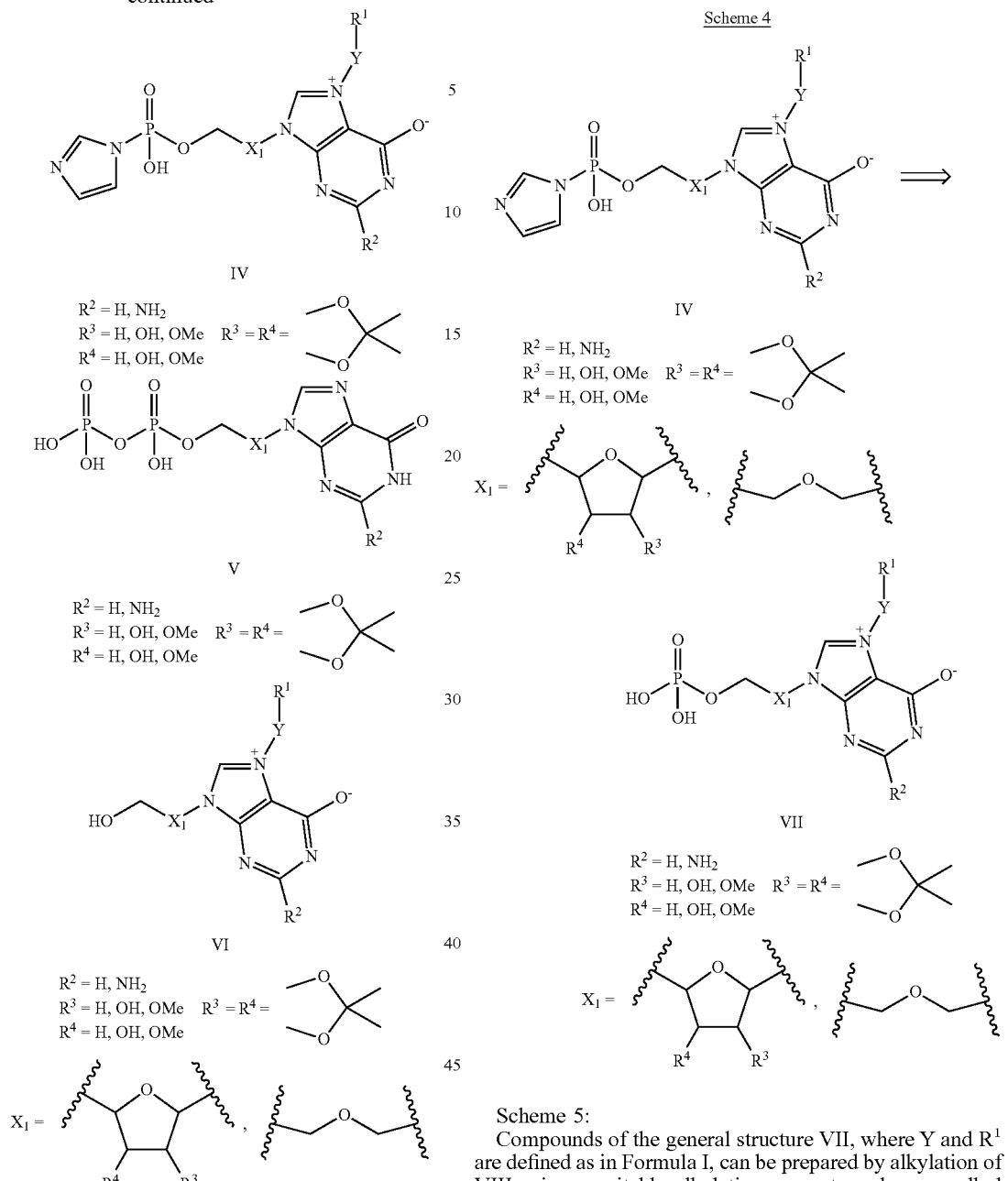

Scheme 4:

Compounds of the general structure IV, where Y and $R^1$ are defined as in Formula I, can be prepared from by treatment of phosphates VII (tributylammonium salts) with imidazole, a suitable tertiary phosphine, such as triphenylphosphine, a suitable oxidant, such as 2,2'-dipyridyldissulfide, and a suitable base, such as triethylamine in a suitable solvent, such as DMF or DMSO at a suitable temperature, such as room temperature (P. C. Joshi, M. F. Aldersley, D. V. Zagorevskii, J. P. Ferris, *Nucleosides, Nucleotides and Nucleic Acids* 2012, 31, 7, 536).

Scheme 5:

Compounds of the general structure VII, where Y and $R^1$ are defined as in Formula I, can be prepared by alkylation of VIII using a suitable alkylation reagent, such as an alkyl halide, triflate, or mesylate in a suitable solvent such as DMF or DMSO at a suitable reaction temperature ranging from room temperature to 50° C.

Compounds of the general structure VIII, where Y and $R^1$ are defined as in Formula I, can be obtained by reaction of X with a suitable phophorylating agent such as phosphoryl chloride in a suitable solvent such as trimethylphosphate at a suitable temperature ranging from 0° C. or room temperature.

Compounds of the general structure VII, where Y and $R^1$ are defined as in Formula I, can also be prepared by reaction of IX with a suitable phophorylating agent such as phosphoryl chloride in a suitable solvent such as trimethylphosphate at a suitable temperature ranging from 0° C. to room temperature.

Compounds of the general structure IX, where Y and $R^1$ are defined as in Formula I, can be prepared by alkylation of X using a suitable alkylation reagent, such as an alkyl halide, triflate, or mesylate in a suitable solvent such as DMF or DMSO at a suitable reaction temperature ranging from room temperature to 50° C.
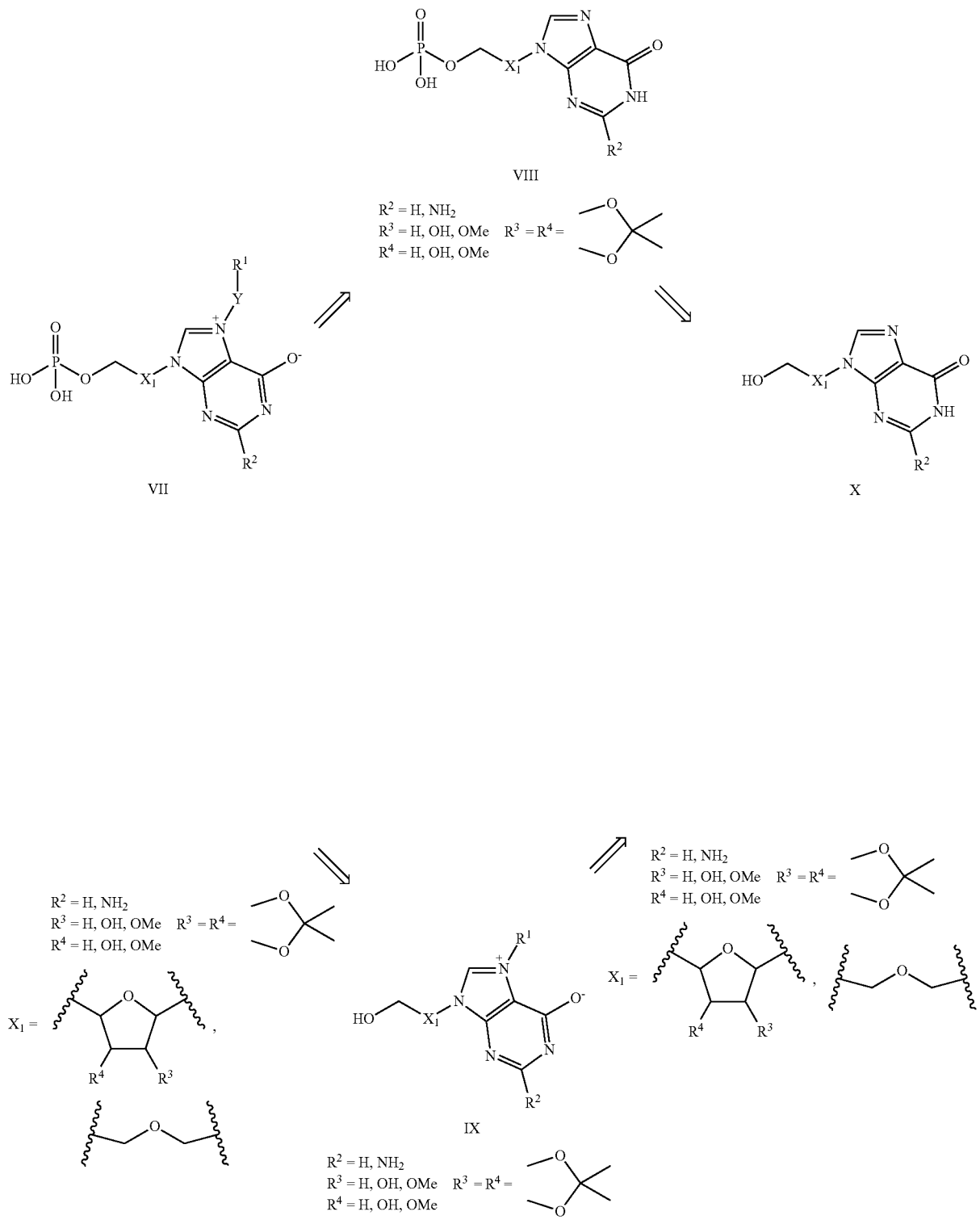

Scheme 6:

Compounds of the general structure VI, where Y and R¹ are defined as in Formula I, can be prepared by alkylation of X using a suitable alkylation reagent, such as an alkyl halide, triflate, or mesylate in a suitable solvent such as DMF or DMSO at a suitable reaction temperature ranging from room temperature to 50° C.

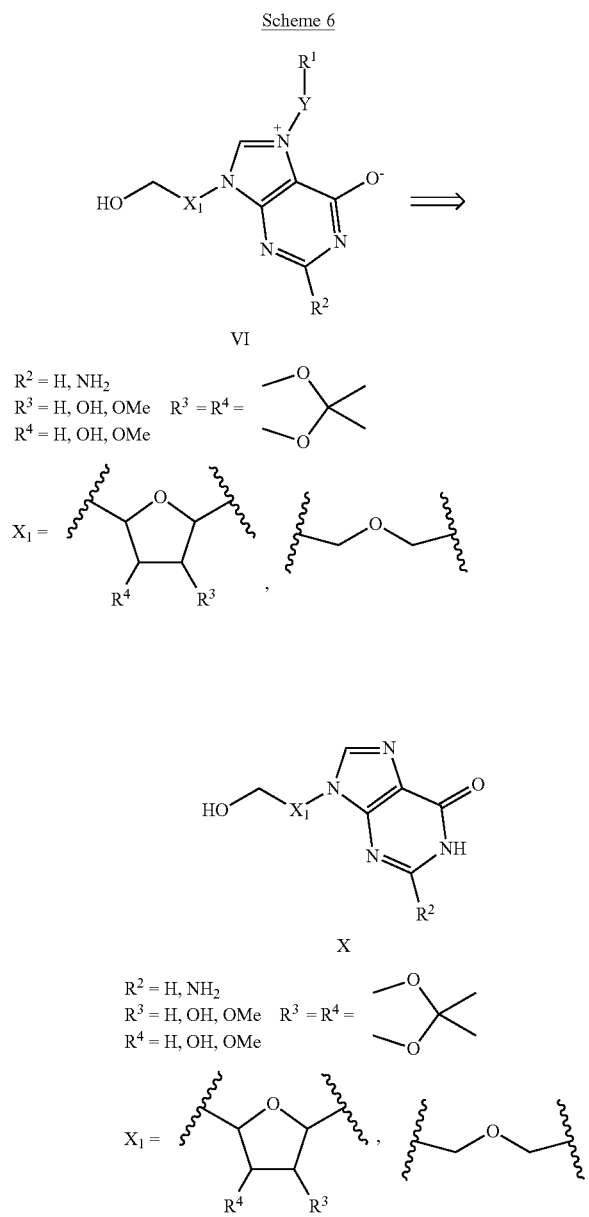

Scheme 7:

When X=Br, Cl, I and A=CH₃, compounds of the general structure XI and XII can be prepared from XIII and XIV, respectively, by radical halogenation using a suitable radical initiator such as azodiisobutyronitrile and a halide donor such as N-bromosuccinimide, N-Bromoacetamide, N-chlorosuccinimide, N-iodosuccinimide, bromide, chloride, or iodide, in a suitable solvent such as carbon tetrachloride at a suitable reaction temperature such at 85° C. (a) K. Ziegler, A. Spath, E. Schaaf, W. Schumann, E. Winkelmann, Ann. 1942, 551, 80; b) A. Nechvatal, Advances in Free-Radical Chemistry (London) 1972, 4, 175).

When X=Br, Cl, I and A=CH₂OH, compounds of the general structure XI and XII can be prepared from XIII and XIV, respectively, by reaction with a suitable phosphine such as triphenylphosphine and a suitable oxidant such as carbon tetrabromide, carbon tetrachloride, N-iodosuccinimide in a suitable solvent such as dichloromethane at a suitable reaction temperature such as room temperature (a) R. Appel, Angew. Chem. Int. Ed. 1979, 14, 801; b) Cadogan, J, ed. (1979). Organophosphorus Reagents in Organic Synthesis. London: Academic Press).

When X=Br, Cl, I and A=CH₂OH, compounds of the general structure XI and XII, can be prepared from XIII and XIV, respectively, by treatment with a suitable acid such as HBr (48% aq.), HCl (12 M aq.), or HI (aq.) (a) M. Uchida, F. Tabusa, M. Komatsu, S. Morita, T. Kanbe, K. Nakagawa, Chem. Pharm. Bull. 1985, 33, 3775; b) V. Boekelheide, G. K. Vick, J. Am. Chem. Soc. 1956, 78, 653; c) K. M. Doxsee, M. Feigel, K. D. Stewart, J. W. Canary, C. B. Knobler, D. J. Cram, J. Am. Chem. Soc. 1987, 109, 3098.).

When X=OMs, OTf and A=CH₂OH, compounds of the general structure XI and XII can be prepared from XIII and XIV, respectively, by reaction with a suitable reagent such as MsCl, (Ms)₂O, (Tf)₂O in the presence of a suitable base such as a tertiary amine, e.g. triethylamine, in a suitable solvent such as dichloromethane.

When A=CH₂OH, compounds of the general structure XIII can be prepared from the corresponding acid (A=COOH) by reaction with a suitable reductant such as borane dimethylsulfide adduct or lithium aluminum hydride in a suitable solvent such as tetrahydrofurane at suitable reaction temperature such as room temperature (a) N. G. Gaylord, Reduction with Complex Metal Hydrides, Wiley, N.Y., 0.1956, 322; b) H. C. Brown, W. Korytnyk, J. Am. Chem. Soc. 1960, 82, 3866).

When A=CH₃, CH₂OH compounds of the general structures XIII and XIV can be prepared by Suzuki crosscoupling reaction using the suitable aryl substrates XV-XVII as starting material (N. Miyaura, A. Suzuki, Chem. Rev. 1995, 95, 2457).

If B=Br, I, OTf, the cross coupling reaction involves reaction of XV or XVI with boron reagents XVII (C=B(OH)₂,Bpin) using a suitable catalyst such as Sphos palladacycle G2 (Chloro(2-dicyclohexylphosphino-2',6'-dimethoxy-1,1'-biphenyl)[2-(2'-amino-1,1'-biphenyl)]palladium(II)) and a suitable base such as K₂CO₃ in a suitable solvent mixture such as DMF/H₂O at a suitable temperature such as room temperature, 50° C., or 80 OC (T. E. Barder, S. D. Walker, J. R. Martinelli, S. L. Buchwald, S. L. J. Am. Chem. Soc. 2005, 127 4685; b) R. A. Altman, S. L. Buchwald, Nature Protocols 2007, 2, 3115-3121). If B=B(OH)₂, Bpin, the cross coupling reaction involves reaction of XV or XVI with reagents XVII (C=Br,I,OTf) using a suitable catalyst such as Sphos palladacycle G2 (Chloro(2-dicyclohexylphosphino-2',6'-dimethoxy-1,1'-biphenyl)[2-(2'-amino-1,1'-biphenyl)]palladium(II)) and a suitable base such as K₂CO₃ in a suitable solvent mixture such as DMF/H₂O at a suitable temperature such as room temperature, 50° C., or 80° C. Compounds XVI-XVII are commercially available.

Scheme 7

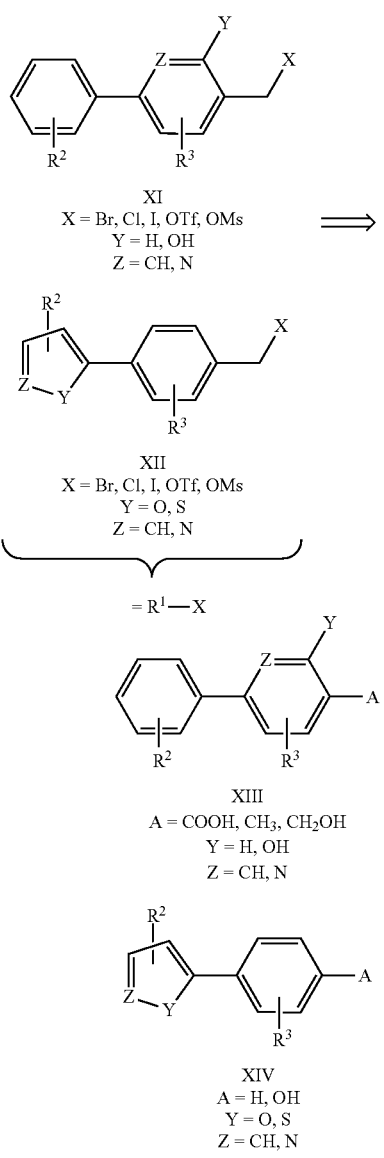

Scheme 8:

Chemically 3'-modified mRNA of the general structure XVIII, as defined in Formula V, can be obtained by reacting RNA with the general structure XX with $NaIO_4$ in a suitably buffered aqueous solution (buffers: NaOAc, TRIS, PBS, MES, HEPES), at a suitable pH, ranging from 5.0-7.5, at a temperature ranging from 0° C. to room temperature, followed by treatment with suitable nucleophiles such as hydrazines, acylhydrazones, hydroxylamines, 1,2-aminothiols, amines.

Chemically 3'-modified mRNA of the general structure XVIII, as defined in Formula V can be obtained by reacting RNA with the general structure XX with $NaIO_4$ in a suitably buffered aqueous solution (buffers: NaOAc, TRIS, PBS, MES, HEPES), at a suitable pH, ranging from 5.0-7.5, at a temperature ranging from 0° C. to room temperature, followed by treatment with a suitable amine nucleophile such as hydrazines, acylhydrazones, hydroxylamines, amines followed by treatment with a suitable reducing agent, such as $NaCNBH_3$, at temperatures ranging from room temperature to 37° C.

RNA of the general structure XIX, as defined in Formula I can be obtained by reacting RNA with the general structure XX with $NaIO_4$ in a suitably buffered aqueous solution (buffers: NaOAc, TRIS, PBS, MES, HEPES), at a suitable pH, ranging from 5.0-7.5, at a temperature ranging from 0° C. to room temperature, followed by treatment with suitable nucleophile such Meldrum's acid.

Scheme 8

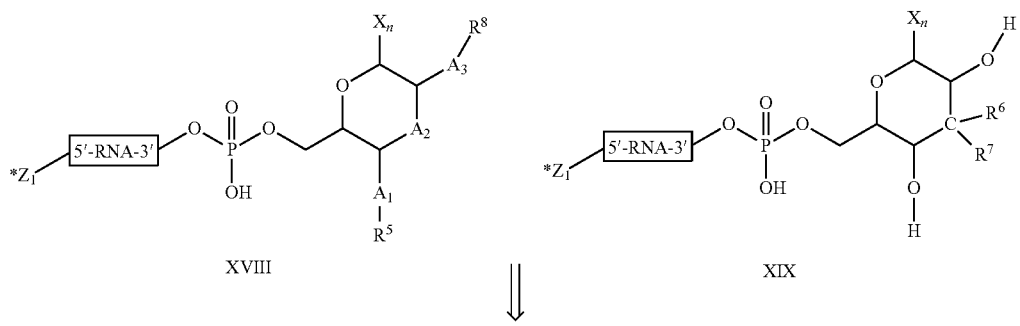

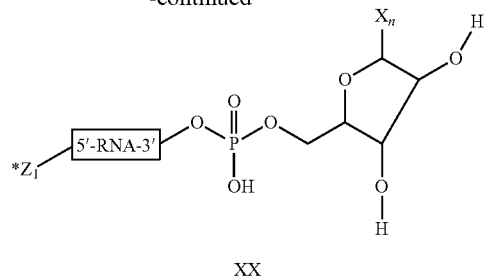
XX
Scheme 9:
5'3'-bismodified RNA of the general structures XXI and XXII, as defined below, can be obtained from 3'-modified RNA of the structure XXIII and XXIV, respectively, by reaction with guanosine derivatives II, under conditions described in Scheme 1.
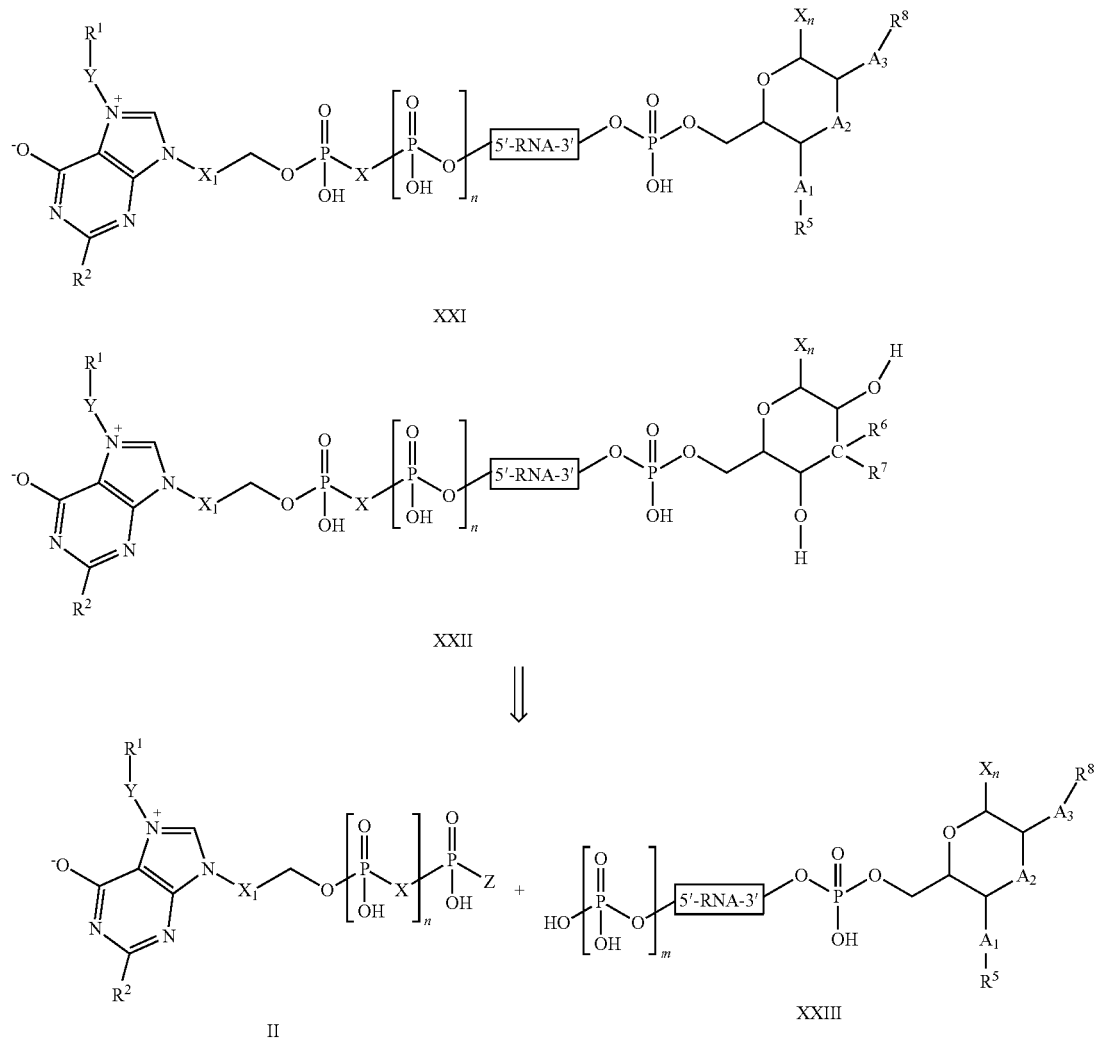

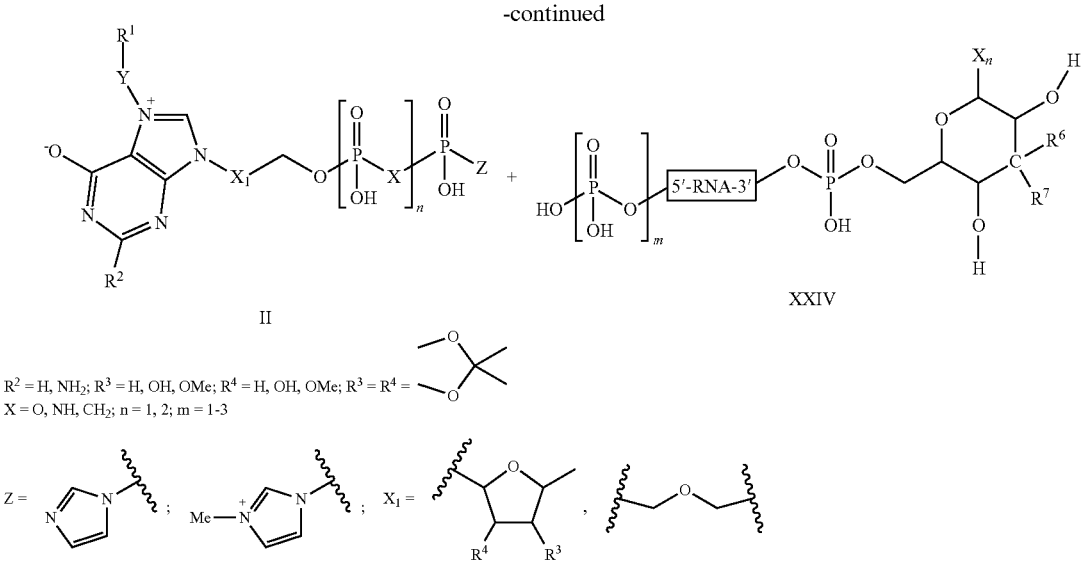

$R^2 = H, NH_2; R^3 = H, OH, OMe; R^4 = H, OH, OMe; R^3 = R^4 =$ (acetonide)
$X = O, NH, CH_2; n = 1, 2; m = 1-3$ Scheme 10:

Chemically capped mRNA of the general structure XXV can be obtained by reacting mRNA-5'-monophosphate with imidazole activated cap structures of the general structure XXVI in a suitably buffered aqueous saline solution (buffers: HEPES, TRIS, MES, PBS) at a suitable pH, ranging from 5.5-7.5, in presence or absence of organic solvents, such as DMF and DMSO, in the presence of a suitable Lewis-acidic activator such as $MnCl_2$, $NiCl_2$, $ZnCl_2$.

Scheme 10

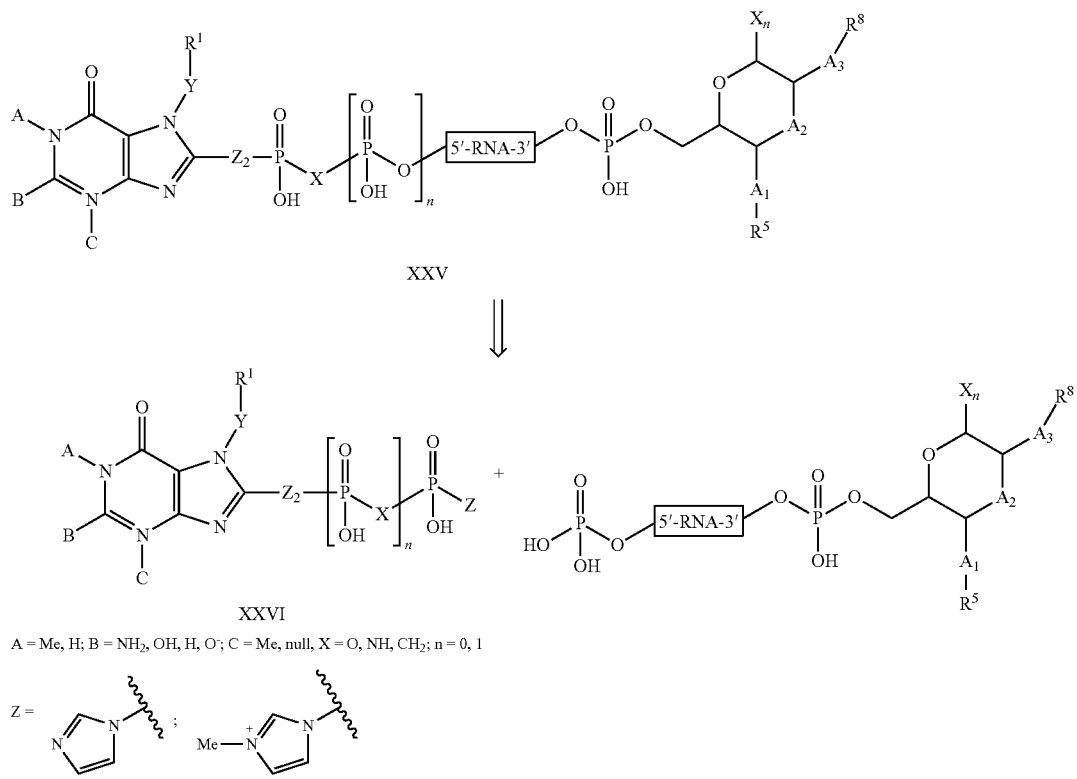

$A = Me, H; B = NH_2, OH, H, O^-; C = Me, null; X = O, NH, CH_2; n = 0, 1$

Exemplary 5' cap structures that can be prepared include,

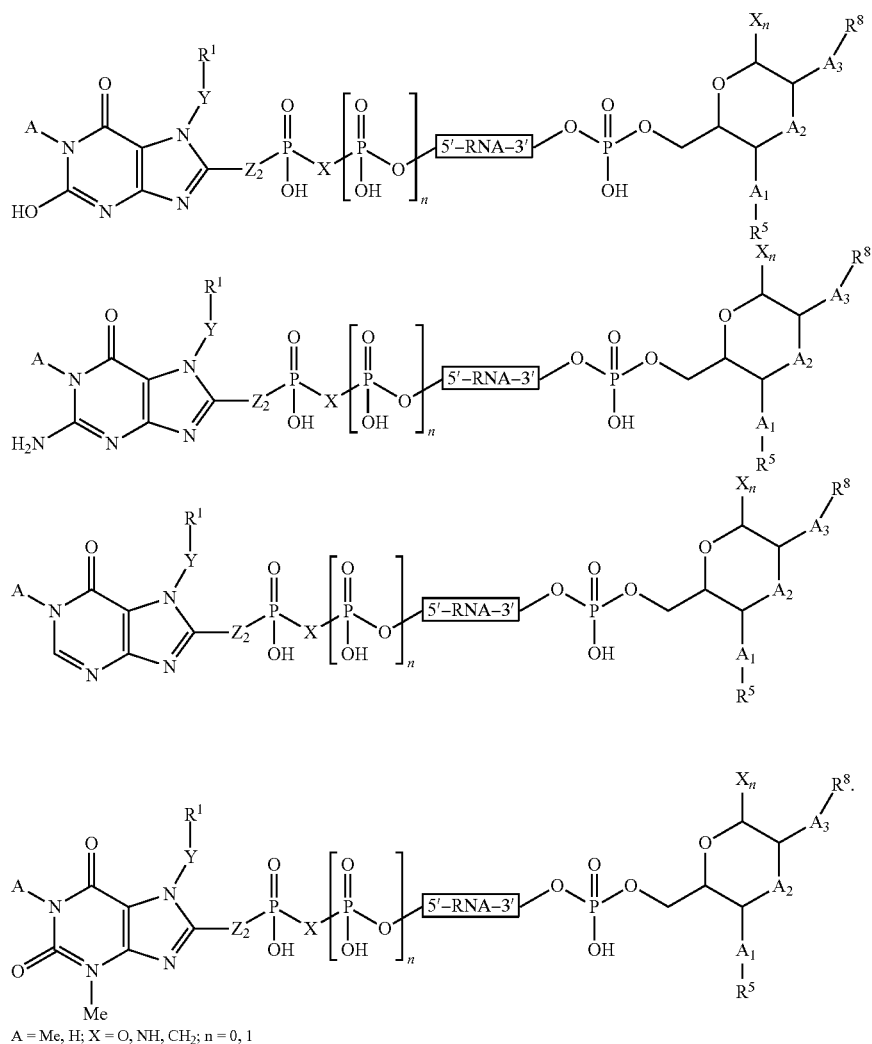

A = Me, H; X = O, NH, CH$_2$; n = 0, 1

Scheme 11:

Compounds of the general structure XXVI, where Y and R$^1$ are defined as in Formula I, can be prepared from by treatment of phosphates XXVII (tributylammonium salts) with imidazole or N-methyl-imidazole, a suitable tertiary phosphine, such as triphenylphosphine, a suitable oxidant, such as 2,2'-dipyridyldissulfide, and a suitable base, such as triethylamine in a suitable solvent, such as DMF, DMSO, NMP, trimethylphosphate at a suitable temperature, such as room temperature (a) M. Lewdorowicz, Y. Yoffe, J. Zuberek, J. Jemielity, J. Stepinski, R. Kierzek, R. Stolarski, M. Shapira, E. Darzynkiewicz, *RNA* 2004, 10, 1469; b) R. Worch, J. Stepinski, A. Niedzwiecka, M. Jankowska-Anyszka, C. Mazza, S. Cusack, R. Stolarski, E. Darzynkiewicz, *Nucleosides Nucleotides and Nucleic Acids* 2005, 24, 1131; c) M. Warminski, J. Kowalska, J. Buck, J. Zuberek, M. Lukaszewicz, C. Nicola, A. N. Kuhn, U. Sahin, E. Darzynkiewicz, J. Jemielity, *Bioorg. Med. Chem.*, 2013, 23, 3753).

Scheme 11

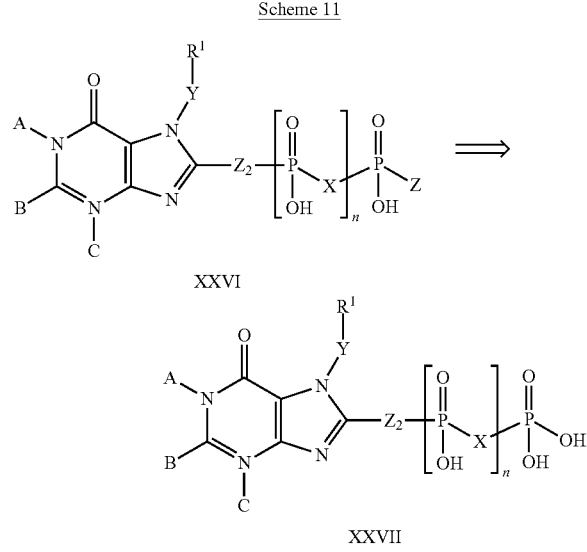

XXVI

XXVII

-continued
A = Me, H; B = NH₂, OH, H, O⁻; C = Me, null; X = O, NH, CH₂; n = 0, 1

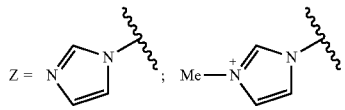

Scheme 12:

Compounds of the general structure XXVII, where Y, $R^1$ and $Z_2$ are defined as in Formula I, can be prepared by reaction of activated phosphates XXIX with triethylammonium phosphate, or a similar phosphate salt, in a suitable solvent such as DMF, DMSO, or water in the presence of a lewis acid such as zinc chloride, magnesium chloride or manganese chloride at a suitable temperature such as room temperature (a) M. Lewdorowicz, Y. Yoffe, J. Zuberek, J. Jemielity, J. Stepinski, R. Kierzek, R. Stolarski, M. Shapira, E. Darzynkiewicz, *RNA* 2004, 10, 1469; b) R. Worch, J. Stepinski, A. Niedzwiecka, M. Jankowska-Anyszka, C. Mazza, S. Cusack, R. Stolarski, E. Darzynkiewicz, *Nucleosides Nucleotides and Nucleic Acids* 2005, 24, 1131; c) M. Warminski, J. Kowalska, J. Buck, J. Zuberek, M. Lukaszewicz, C. Nicola, A. N. Kuhn, U. Sahin, E. Darzynkiewicz, J. Jemielity, *Bioorg. Med. Chem.*, 2013, 23, 3753).

When X=O, compounds of the general structure XXVII, where Y, $R^1$ and $Z_2$ are defined as in Formula I, can also be prepared by reaction of XXVIII with diphosphoric acid tetrachloride in a suitable solvent such as trimethylphosphate at a suitable temperature ranging from 0° C. to room temperature (J. Emsley, J. Moore, P. B. Udy, *J. Chem. Soc. (A) Inorg. Phys. Theor.* 1971, 2863).

When X=NH, compounds of the general structure XXVII, where Y, $R^1$ and $Z_2$ are defined as in Formula I, can also be prepared by reaction of XXVIII with imido-bis(phosphoryldichloride) in a suitable solvent such as trimethylphosphate at a suitable temperature ranging from 0° C. to room temperature (A. M. Rydzik, M. Kulis, M. Lukaszewicz, J. Kowalska, J. Zuberek, Z. M. Darzynkiewicz, E. Darzynkiewicz, J. Jemielity, *Bioorganic & Med. Chem.* 2012, 20, 1699).

When X=CH₂, compounds of the general structure XXVII, where Y, $R^1$ and $Z_2$ are defined as in Formula I, can also be prepared by reaction of XXVIII with methylenebis(phosphonic dichloride) in a suitable solvent such as trimethylphosphate at a suitable temperature such as 0° C. or room temperature (a) M. Honcharenko, M. Zytek, B. Bestas, P. Moreno, J. Jemielity, E. Darzynkiewicz, C. I. E. Smith, R. Stroemberg, *Bioorg. Med. Chem.*, 2013, 21, 7921; b) M. Kalek, J. Jemielity, Z. M. Darzynkiewicz, E. Bojarska, J. Stepinski, R. Stolarski, R. E. Davis, E. Darzynkiewic, *Bioorg. Med. Chem.* 2006, 14, 3223; c) M. Kalek, J. Jemielity, J. Stepinski, R. Stolarski, E. Darzynkiewics, *Tetrahedron Lett.* 2005, 46, 2417).

Compounds of the general structure XXIX (Z=imidazole, N-methylimidazolium), where Y, $R^1$ and $Z_2$ are defined as in Formula I, can be prepared from by treatment of phosphates XXIX (Z=OH, tributylammonium salts) with imidazole or N-methyl-imidazole, a suitable tertiary phosphine, such as triphenylphosphine, a suitable oxidant, such as 2,2'-dipyridyldisulfide, and a suitable base, such as triethylamine in a suitable solvent, such as DMF, DMSO, NMP, trimethylphosphate at a suitable temperature, such as room temperature (a) M. Lewdorowicz, Y. Yoffe, J. Zuberek, J. Jemielity, J. Stepinski, R. Kierzek, R. Stolarski, M. Shapira, E. Darzynkiewicz, RNA 2004, 10, 1469; b) R. Worch, J. Stepinski, A. Niedzwiecka, M. Jankowska-Anyszka, C. Mazza, S. Cusack, R. Stolarski, E. Darzynkiewicz, *Nucleosides Nucleotides and Nucleic Acids* 2005, 24, 1131; c) M. Warminski, J. Kowalska, J. Buck, J. Zuberek, M. Lukaszewicz, C. Nicola, A. N. Kuhn, U. Sahin, E. Darzynkiewicz, J. Jemielity, *Bioorg. Med. Chem.*, 2013, 23, 3753).

Compounds of the general structure XXIX (Z=OH), where Y, $R^1$ and $Z_2$ are defined as in Formula I, can also be prepared by reaction of XXVIII with a suitable phophorylating agent such as phosphoryl chloride in a suitable solvent such as trimethylphosphate at a suitable temperature ranging from 0° C. to room temperature.

Compounds of the general structure XXVII, where Y, $R^1$ and $Z_2$ are defined as in embodiment Formula I, can also be prepared by crosscoupling reaction using the suitable aryl substrates and compound XXX as starting material (N. Miyaura, A. Suzuki, *Chem. Rev.* 1995, 95, 2457).

Compound XXX can be obtained by alkylation of the commercially available 8-bromo-3-methyl-1H-purine-2,6(3H,7H)-dione (A=H) or 8-bromo-1,3-dimethyl-1H-purine-2,6(3H,7H)-dione (A=Me) using a suitable alkylation reagent, such as an alkyl halide, triflate, or mesylate in a suitable solvent such as DMF, DMSO, or NMP at a suitable reaction temperature ranging from room temperature to 60° C.

Scheme 12

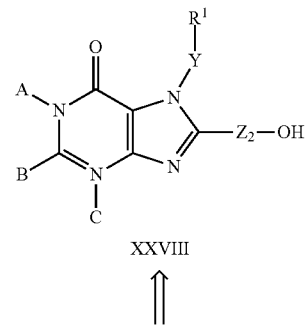

XXVIII

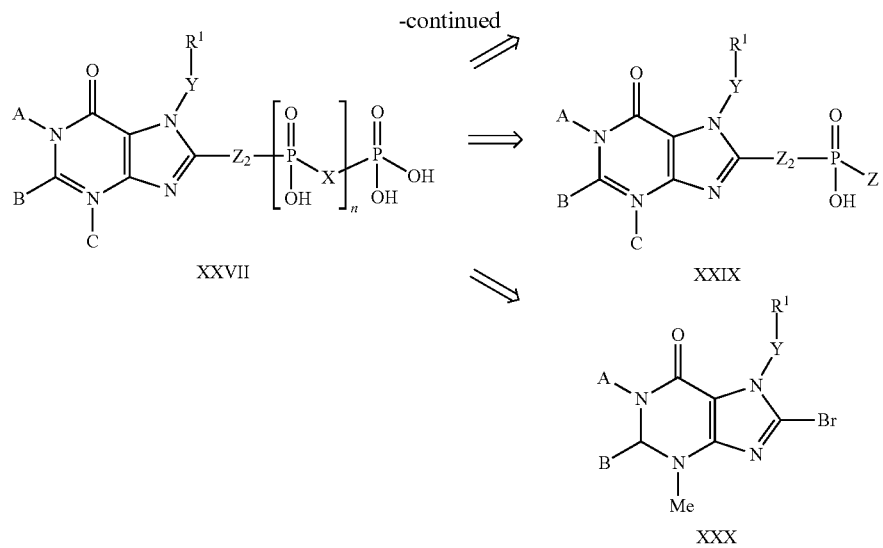

XXVII ⇒ XXIX

XXX

A = Me, H; B = NH₂, OH, H, O⁻; C = Me, null; X = O, NH, CH₂; n = 0, 1

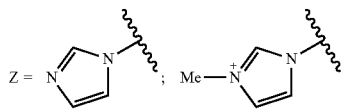

Scheme 13:

Compounds of the general structure XXVIII, where Y, R¹ and Z₂ are defined as in Formula I, can be obtained from amides of the general structure XXXII by cyclization using an appropriate base, such as sodium tert-butoxide, potassium tert-butoxide, or sodium iso-propoxide, in a suitable solvent, such as ethanol, isopropanol, or THF, at temperatures ranging from 50-100° C.

Compounds of the general structure XXIX, where Y, R¹ and Z₂ are defined as in Formula I, can be obtained from mono- or dialkyl phosphanes and phosphates of the general structure XXXI by hydrolysis using a suitable lewis acid, such as trimethylsilyl bromide, boron tribromide, or aluminum trichloride, in a solvent such as DMF, DMSO, NMP, or THF, at temperatures ranging from 0° C. to 30° C.

Compounds of the general structure XXXI, where Y, R¹ and Z₂ are defined as in embodiment Formula I, can be obtained from amides of the general structure XXXII by cyclization using an appropriate base, such as sodium tert-butoxide, potassium tert-butoxide, or sodium iso-propoxide, in a suitable solvent, such as ethanol, isopropanol, or THF, at temperatures ranging from 50-100° C.

Scheme 13

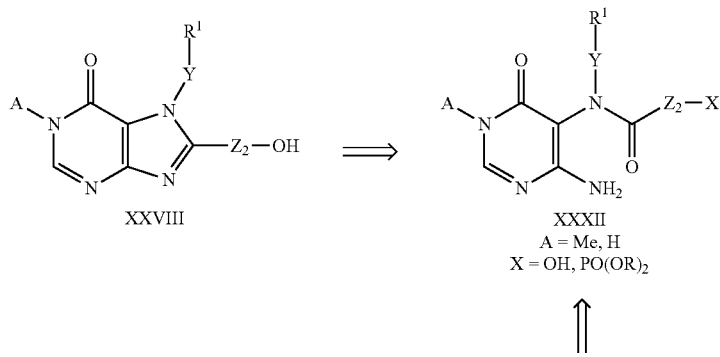

XXVIII  XXXII
A = Me, H
X = OH, PO(OR)₂

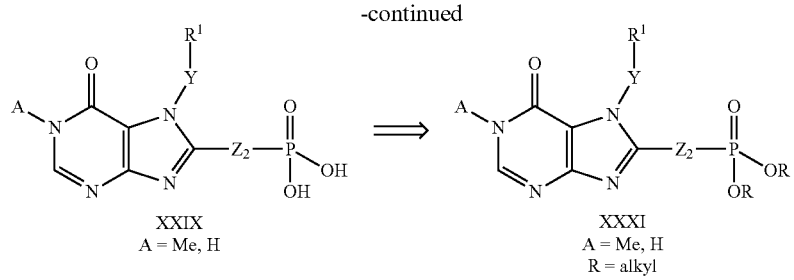

XXIX
A = Me, H

XXXI
A = Me, H
R = alkyl

Scheme 14:

Compounds of the general structure XXXII, where Y, $R^1$ and $Z_2$ are defined as in embodiment XXX, can be obtained by acylation of XXXIII with the appropriate carboxylic acid of the linker unit using a suitable activator such as HATU, HBTU, O-(benzotriazol-1-yl)-N,N,N',N'-tetramethyluronium tetrafluoroborate, or (Benzotriazol-1-yloxy)tripyrrolidinophosphonium hexafluorophosphate and a suitable base such as triethylamine or Hunig's base, in a suitable solvent, such as DMF, DMSO, or NMP at temperatures ranging from room temperature to 50° C.

Compounds of the general structure XXXIII, where Y, $R^1$ is defined as in embodiment Formula I, can be obtained by reduction of XXXIV (where Y is the corresponding carboxylic acid of the substituent R1) using a reducing agent, such as lithium aluminum hydride or Red-Al, in a suitable solvent such as THF, diethylether, or dioxane at temperatures ranging from room temperature to 120° C.

Compounds of the general structure XXXIV, can be obtained by acylation of commercially available 5,6-diaminopyrimidine-4(3H)-one (XXXV) with the appropriate carboxylic acid to introduce substitutent $R^1$ using a suitable activator such as HATU, HBTU, O-(benzotriazol-1-yl)-N,N,N',N'-tetramethyluronium tetrafluoroborate, or (Benzotriazol-1-yloxy)tripyrrolidinophosphonium hexafluorophosphate and a suitable base such as triethylamine or Hunig's base, in a suitable solvent, such as DMF, DMSO, or NMP at temperatures ranging from room temperature to 50° C.

Scheme 14

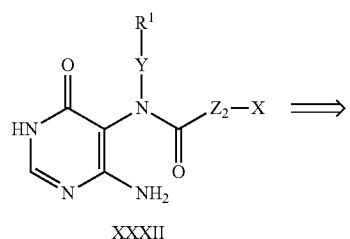

XXXII

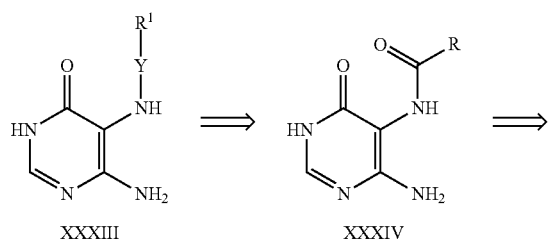

XXXIII

XXXIV

X = OH, PO(OR)$_2$; R = alkyl

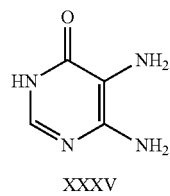

XXXV

Scheme 15:

5'3'-bismodified RNA of the general structures XXXVI and XXXVII, as defined above, can be obtained from 3'-modified RNA of the structure XL and XLI, respectively, by reaction with guanosine derivatives XXVI, under conditions described in Scheme 1. The synthesis of XXVI is described in Scheme 10.

Scheme 15

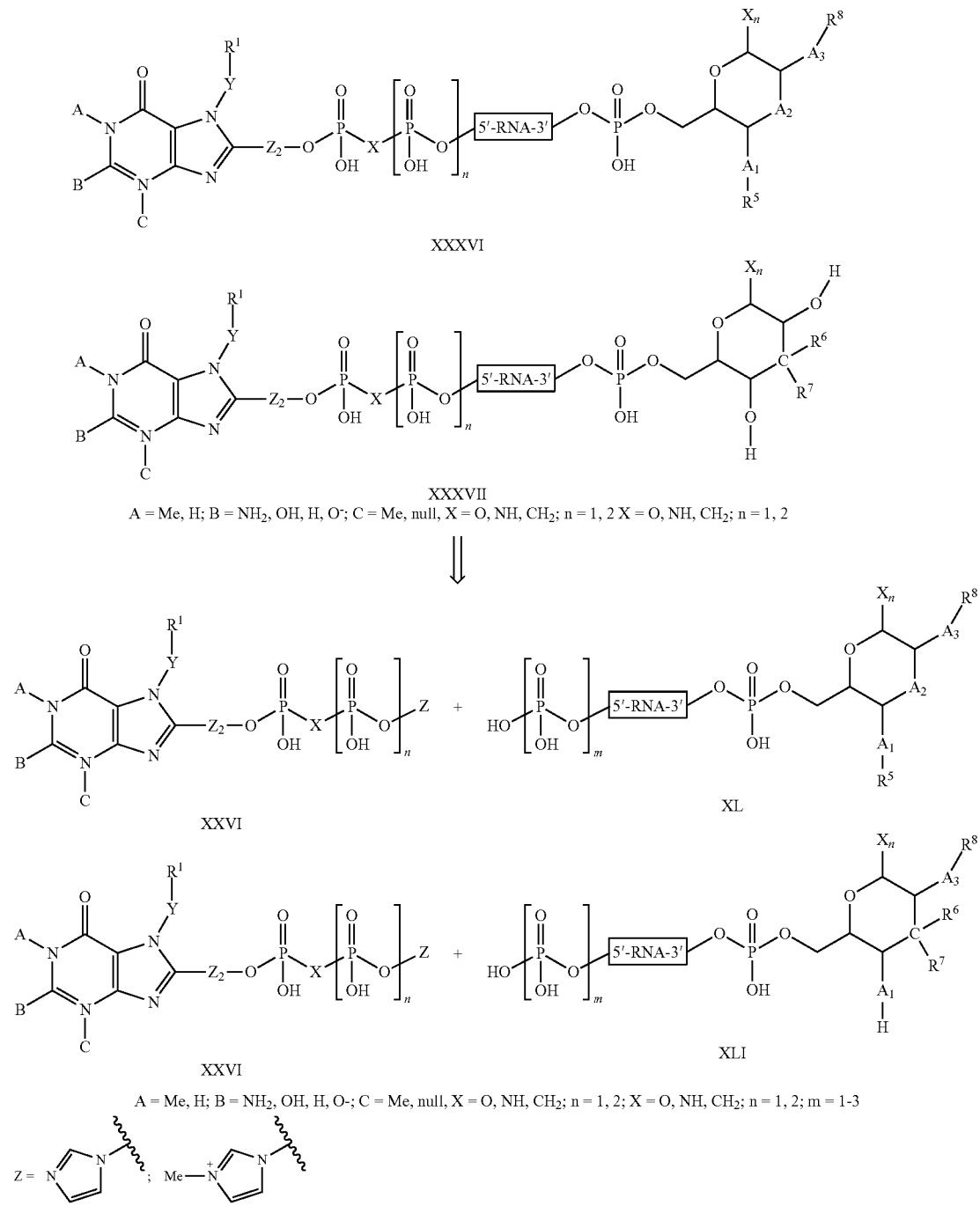

Definitions

The term "acyl" refers to an optionally substituted alkyl carbonyl, optionally substituted arylcarbonyl. Examples of such acyl groups include acetyl, benzoyl, and the like.

The term "affinity moiety" refers to a molecule that specifically binds to a molecule of interest, such as a protein, or nucleic acid or other molecule. Examples of affinity moiety include, but are not limited to, biotin and digoxigenin.

The term "alkanediyl" refers divalent radicals of the general formula $C_nH_{2n}$ derived from aliphatic hydrocarbons. Unless specified otherwise, such alkanediyls include substituted alkanediyls. Suitable examples include methanediyl (—$CH_2$—), ethanediyl (—$CH_2$—$CH_2$—), and the like.

The terms "alkenyl" and "alkynyl" as used herein, alone or in combination, refers to aliphatic straight-chain or branched hydrocarbon chains that contain 1 to 20 carbon atoms and include one or more units of unsaturation. Alkenyl contains at least one carbon-carbon double bond, but no carbon-carbon triple bonds. Alkynyl contains at least one carbon-carbon triple bond. Preferred alkenyl and alkynyl group may comprise from 2 to 10 carbon atoms or from 2 to 6 carbon atoms. Suitable alkenyl groups include, for example, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl. Suitable alkynyl groups include, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl. Alkenyl and Alkynyl groups may be optionally substituted as described herein.

The term "alkyl," as used herein, alone or in combination, refers to an aliphatic straight-chain or branched, saturated hydrocarbon chain containing from 1 to 20 carbon atoms. In certain embodiments, the alkyl group may comprise from 1 to 10 carbon atoms. In further embodiments, the alkyl group may comprise from 1 to 6 carbon atoms. Alkyl groups may be optionally substituted as described herein. Examples of alkyl groups include methyl, ethyl, n-propyl, isopropyl, n-butyl, isobutyl, sec-butyl, tert-butyl, pentyl, iso-amyl, hexyl, octyl, noyl and the like.

The term "amino" refers to the group —$NH_2$.

The term "aminoalkyl" refers to an alkyl substituted with a primary, secondary or tertiary amino group. Preferred aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms. Examples of such aminoalkyl include aminomethyl, aminoethyl, and the like.

The term "aryl," as used herein, alone or in combination, means a carbocyclic aromatic hydrocarbon ring system containing at least one aromatic ring. The aromatic ring system can be a fused ring system including aromatic or non-aromatic hydrocarbon rings or an aromatic ring system that include a non-aromatic hydrocarbon ring. The term "aryl" embraces aromatic groups such as phenyl, naphthyl, anthracenyl, and phenanthryl. Aryl may be optionally substituted as described herein.

The term "cap 0" refers to the caps in which the only methylation is in the $^{m7}G$. The term "cap 1" refers to caps with additional methylation in $N_1$. The generalized cap structure is represented as $^{m7}G(5')ppp(5')N_1{}^mpN_2{}^mpN_3p\ldots$ where N is any nucleotide, preferably a purine or a pyrimidine, p is a phosphate group and m is a methyl group. The $^{m7}G$, containing a methyl group at the $N^7$ position of guanosine, is at the extreme 5' terminus of the mRNA. Methylations at the $N_1$ and $N_2$ positions, on the other hand, are substitutions at the 2'-OH group of the ribose moiety. The various cap structures are classified on the basis of the number of methyl groups they contain (Banerjee, A. K. *Microbiological Rev.*, 1980, 44, 175).

The term "cycloalkenyl," as used herein, alone or in combination with other terms, represents, unless otherwise stated, cyclic versions of "alkenyl" containing at least one carbon-carbon double bond, with preferably 3 to 10 carbon atoms, i.e., 3, 4, 5, 6, 7, 8, 9, or 10 carbon atoms, preferably 3 to 6 carbon atoms, forming a ring. The term "cycloalkenyl" is also meant to include bicyclic versions thereof. If bicyclic rings are formed it is preferred that the respective rings are connected to each other at two adjacent carbon atoms, however, alternatively the two rings are connected via the same carbon atom, i.e., they form a spiro ring system or they form bridged ring systems. Examples of cycloalkenyl include cyclopropenyl, cyclobutenyl, cyclopentenyl, cyclopentadienyl, cyclohexenyl, 1,3-cyclohexenyl, cycloheptenyl, cycloheptatrienyl, cyclooctenyl, cyclononeyl, cyclodecenyl, bicyclo[2.2.1]-2-heptenyl, bicyclo[2.2.1]-2-octenyl, or bicyclo[4.4.0]-2-decenyl. A cycloalkenyl group may be optionally substituted as described herein.

The term "cycloalkyl," as used herein, alone or in combination with other terms, represents, unless otherwise stated, cyclic versions of "alkyl" including bicyclic and polycyclic alkyl groups. The rings of a bicyclic or polycyclic ring system can be fused are linked through a single shared atom i.e., they form a spiro ring system or a bridged ring system. A cycloalkyl can preferably contain 3 to 10 carbon atoms, i.e., 3, 4, 5, 6, 7, 8, 9, or 10 carbon atoms, preferably 3 to 6 carbon atoms forming a ring. Examples of suitable cycloalkyl groups include cyclopropyl, cyclobutyl, cyclopentyl, cyclohexyl, cycloheptyl, cyclooctyl, cyclononyl, or cylcodecyl. Examples of suitable cycloalkyl groups include cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, and the like. A cycloalkyl group may be optionally substituted as described herein.

The term "detection moiety" refers to chemical moieties that can be readily detected using suitable methods. Examples of detection moiety include, but are not limited to, fluorescent materials, luminescent materials, bioluminescent materials, and radioactive materials.

The term "half-life" ($T_{1/2}$) relates to the period of time which is needed to eliminate half of the activity, amount, or number of molecules. In the context of the present invention, the half-life of RNA is indicative of the stability of said RNA.

The term "hetero atom" refers to nitrogen, oxygen and sulfur.

The term "heteroaryl," as used herein, is an aryl in which one or more carbon ring atoms are independently replaced by O, S, and N. In certain embodiments, the heteroaryl may comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like. Heteroaryl may be optionally substituted as described herein.

The term "heterocyclyl" means a cycloalkyl group as defined above in which from 1 to 3 carbon atoms in the ring are independently replaced by O, S, or N. Examples of such heterocyclyl groups are pyrrolidinyl, imidazolidinyl, oxazolidinyl, thiazolidinyl, tetrahydrofuranyl, piperidinyl, piperazinyl, morpholinyl, thiomorpholinyl, tetrahydropyranyl, dioxanyl, indolinyl, isoindolinyl, dihydrobenzofuranyl, dihydro-isobenzofuranyl, tetrahydroquinolinyl, tetrahydroisoquinolinyl, tetrahydroquinoxalinyl, chromanyl, isochromanyl, dihydrobenzooxazinyl, dihydrobenzothiazinyl, or dihydrobenzodioxinyl. A heterocyclyl may be optionally substituted as described herein.

The term "immunogenicity" refers to the capacity to induce an immune reaction.

The term "linking group" refers to a divalent radical that links two other moieties. The linking group generally will contain between 1 and 40 atoms and can be, for example, an alkyl, alkenyl, alkynyl, cycloalkyl, cycloalkenyl, aryl, heteroaryl or heterocycle linking group, each of which can optionally be substituted as described herein. For example, suitable linking groups include methanediyl (—CH$_2$—), ethanediyl (—CH$_2$—CH$_2$—), ethenediyl (—CH=CH—), ethynediyl (—C≡C—), —CH$_2$CH$_2$CH$_2$—, —CH$_2$CH(CH$_3$)—, —C(CH$_3$)$_2$—, —(C$_6$H$_4$)—, —(C$_6$H$_{10}$)—, and the like. Additional examples of suitable linking groups include but not limited to

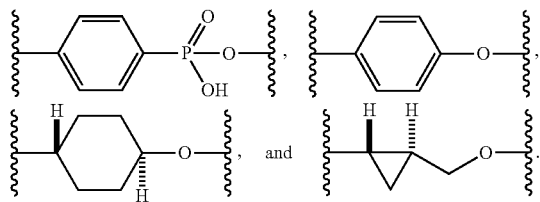

The term "lower," as used herein, alone or in a combination, where not otherwise specifically defined, means containing from 1 to and including 6 carbon atoms.

The term "nucleobase" refers to nitrogen-containing bases that are components of nucleotides. Nucleobases include, for example, the primary nucleobases cytosine, guanine, adenine, thymine, uracil; pseudouracil; as well as modified nucleobases, such as, m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'1m (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); mlG (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluricjine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethy l aminomethyl-2-L-Omethy 1 uridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C$_1$-C$_6$)-alkyluracil, 5-methyluracil, 5-(C$_2$-C$_6$)-alkenyluracil, 5-(C$_2$-C$_6$)-alkynyluracil, 5-(hydroxymethyl)uracil, 5-chlorouracil, 5-fluorouracil, 5-bromouracil, 5-hydroxycytosine, 5-(C$_1$-C$_6$)-alkylcytosine, 5-methylcytosine, 5-(C$_2$-C$_6$)-alkenylcytosine, 5-(C$_2$-C$_6$)-alkynylcytosine, 5-chlorocytosine, 5-fluorocytosine, 5-bromocytosine, N$^2$-dimethylguanine, 7-deazaguanine, 8-azaguanine, 7-deaza-7-(C$_2$-C$_6$)alkynylguanine, 8-hydroxyguanine, 6-thioguanine, 8-oxoguanine, 2-aminopurine, 2-amino-6-chloropurine, 2,4-diaminopurine, 2,6-diaminopurine, 8-azapurine, and the like.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, nitrile, $CF_3$, cycloalkyl, pyridinyl, thiophene, furanyl, lower carbamate, halophenyl, hydroxyphenyl, haloalkyl and hydroxyalkyl. Two substituents may be joined together to form a five-, six-, or seven-membered aromatic or non-aromatic carbocyclic or heterocyclic ring containing one to three heteroatoms, for example forming methylenedioxy or ethylenedioxy. An optionally substituted group may be unsubstituted (e.g., $—CH_2CH_3$), fully substituted (e.g., $—CF_2CF_3$), monosubstituted (e.g., $—CH_2CH_2F$) or substituted at a level anywhere in-between fully substituted and monosubstituted (e.g., $—CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The compounds according to the present invention can be provided in "pharmaceutically acceptable preparations". Such compositions may contain salts, buffers, preserving agents, carriers and optionally other therapeutic agents. "Pharmaceutically acceptable salts" comprise salts that are physiologically compatible and preferably non-toxic. For example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphor sulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate. gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, Berge, S. M. et al *J. Pharm. Sci.* 1977, 66, 1-19).

The term "PEG" refers to polymers having the repeat unit

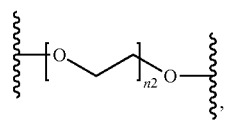

where n2 is 2 to 12. Straight or branched polyethylene glycol polymers are encompassed by this term, and includes the monomethylether of polyethylene glycol (mPEG). The term "PEG" also encompasses Newkome-type dendritic molecules such as

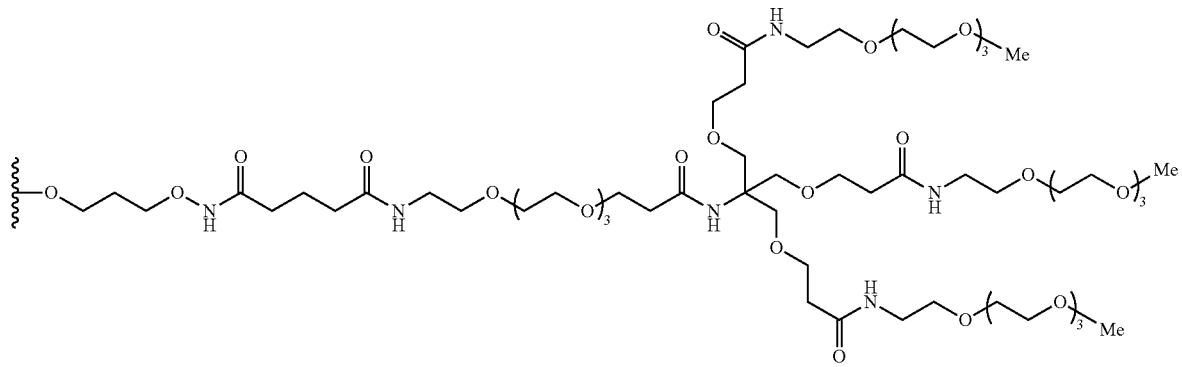

and also

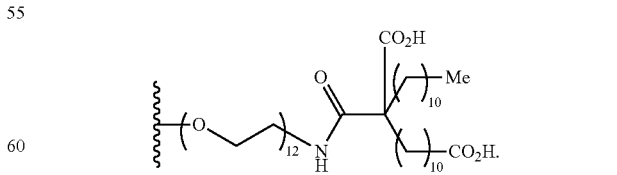

PEGs are commercially available in a number of formulations (e.g., Carbowax™ (Dow Chemical, Midland, Mich.), Poly-G® (Arch Chemicals, Norwalk Conn.), and Solbase).

The term "polyamine" refers to amine compounds containing at least two amino groups which have at least one amino hydrogen atom. Examples of polyamine include, but not limited to polyethylene imine, polypropylene-imine, poly-vinylamine, polyallylamine, ethylene diamine, hexamethylene diamine, diethylene triamine, triethylene tetramine, tetraethylene pentamine and bishexamethylene triamine.

In the Formulas disclosed herein, the representation

5'-RNA-3', refers to an RNA in 5'→3' orientation.

EXAMPLES

Materials and Methods:

All reagents were purchased from commercial sources and used without treatment, unless otherwise indicated. NMR spectra were run on Bruker AVANCE 400 MHz or 500 MHz NMR spectrometers using ICON-NMR, under TopSpin program control. $^{13}C$ NMR and $^{31}P$ NMR spectra were recorded. Spectra were measured at 298K, unless indicated otherwise, and were referenced relative to the solvent resonance. Chemical shifts (δ) are reported in ppm, and signals are described as s (singlet), d (doublet), t (triplet), q (quartet), and m (multiplet). Mass spectra were acquired on LC-MS systems using electrospray ionization methods from a range of instruments of the configurations shown below. $[M+H]^+$ refers to protonated molecular ion of the chemical species. $[M-H]^-$ refers to a deprotonated molecular ion of the chemical species.

LCMS Method 1RXNMON_ACIDC

| Instrument | Agilent 1100 HPLC; Waters Micromass ZQ Mass Spectrometer |
|---|---|
| Column | Sunfire C18 3.5 μm 30 × 3.0 mm, 3.5 μm |
| Column Temperature | 40° C. |
| Eluents | A: $H_2O$ + 0.05% TFA, B: acetonitrile |
| Flow Rate | 2 ml/min |
| Gradient | 5%-95% B in 1.7 min |

LCMS Method 2 RXNMON Acidic_Polar_=RXNMON Acidic_Polar_PosNeg

| Instrument | Agilent 1100 HPLC; Waters Micromass ZQ Mass Spectrometer |
|---|---|
| Column | Sunfire C18 3.5 μm 30 × 3.0 mm, 3.5 μm |
| Column Temperature | 40° C. |
| Eluents | A: $H_2O$ + 0.05% TFA, B: acetonitrile |
| Flow Rate | 2 ml/min |
| Gradient | 1% to 30% B in 1.20 min, 30% to 95% B in 0.65 min |

LCMS Method 4 RXNMON_Basic_Polar

| Instrument | Agilent 1100 HPLC; Waters Micromass ZQ Mass Spectrometer |
|---|---|
| Column | Xbridge C18 3.5 μm 30 × 3.0 mm, 3.5 μm |
| Column Temperature | 40° C. |
| Eluents | A: $H_2O$ + 5 mM ammonium hydroxide, B: acetonitrile |
| Flow Rate | 2 ml/min |
| Gradient | 1% to 30% B in 1.20 min, 30% to 95% B in 0.65 min |

LCMS Method 5 SQ4mRNAcap_FIA Acidic

| Instrument | Waters Acquity UPLC with SQ detector |
|---|---|
| Column | Acquity BEH C18 1.7 μm 2.1 × 50 mm |
| Column Temperature | 50° C. |
| Eluents | A: $H_2O$ + 0.1% formic acid, B: acetonitrile + 0.1% formic acid |
| Flow Rate | 1 ml/min |
| Gradient | 50% B isocratic for 2.16 min |

LCMS Method 6 Acquity LCTp2 Tof_product analysis acidic

| Instrument | Waters Acquity UPLC with Waters LCT Premier XE detector |
|---|---|
| Column | Acquity BEH C18 1.7 μm 2.1 × 50 mm |
| Column Temperature | 50° C. |
| Eluents | A: $H_2O$ + 0.1% formic acid, B: acetonitrile + 0.1% formic acid |
| Flow Rate | 1 ml/min |
| Gradient | 2%-98% B in 7.5 min |

LCMS Method 7 SQ4 acidic polar

| Instrument | Waters Acquity UPLC with SQ detector |
|---|---|
| Column | Acquity BEH C18 1.7 μm 2.1 × 50 mm |
| Column Temperature | 50° C. |
| Eluents | A: $H_2O$ + 0.1% formic acid, B: acetonitrile + 0.1% formic acid |
| Flow Rate | 1 ml/min |
| Gradient | 1%-30% B in 1.20 min; 30%-98% B in 0.95 min |

LCMS Method 8 SQ4 acidic

| Instrument | Waters Acquity UPLC with SQ detector |
|---|---|
| Column | Acquity BEH C18 1.7 μm 2.1 × 50 mm |
| Column Temperature | 50° C. |
| Eluents | A: $H_2O$ + 0.1% formic acid, B: acetonitrile + 0.1% formic acid |
| Flow Rate | 1 ml/min |
| Gradient | 2%-98% B in 1.76 min |

LCMS Method 9 IPC

| Instrument | Micromass Quattro micro API, Agilent 1100 Series pump |
|---|---|
| Column | Xbridge BEH C18 2.5 μm 3.0 × 100 mm |
| Column Temperature | 80° C. |
| Eluents | A: $H_2O$ + 200 mM HFIP + 8 mM TEA, B: methanol |
| Flow Rate | 1 ml/min |
| Gradient | 30% B until 3.65 min; to 99% B at 3.75 min, 99% B until 3.85 min |

LCMS Method 10 scout basic peptide

| Instrument | Agilent 1100 HPLC; Waters Micromass ZQ Mass Spectrometer |
|---|---|

-continued

| | |
|---|---|
| Column | Xbridge C18 3.5 μm, 30 × 3.0 mm, 3.5 μm |
| Column Temperature | 40° C. |
| Eluents | A: H₂O + 5 mM ammonium hydroxide, B: acetonitrile |
| Flow Rate | 2 ml/min |
| Gradient | 5% to 80% B in 4.30 min, to 95% B at 5.0 min |

Abbreviations

ATP adenosine 5'-triphosphate
Atm atmosphere
AcOH acetic acid
Aq aqueous
Ar aryl
br broad
br.s., bs broad singlet
BSA bovine serum albumin
° C. Celsius
CDCl₃ deuterated chloroform
CH₂Cl₂, DCM dichloromethane
CH₃CN, MeCN acetonitrile
d doublet
dd doublet of doublets
ddd doublet of doublets of doublets
DIPEA N-ethyldiisopropylamine
DMF N,N-dimethylformamide
DMAP dimethyl aminopyridine
DMSO dimethylsulfoxide
dt doublet of triplets
ESI electrospray ionization
EtOAc ethyl acetate
EtOH ethanol
FCC flash column chromatography
G gauge
GMP guanosine 5'-monophosphate
GDP guanosine 5'-diphosphate
GTP guanosine 5'-triphosphate
h hour
HCl hydrochloric acid
HATU 1-[Bis(dimethylamino)methylene]-1H-1,2,3-triazolo[4,5-b]pyridinium 3-oxid hexafluorophosphate
HBTU O-(Benzotriazol-1-yl)-N,N,N',N'-tetramethyluronium hexafluorophosphate
HEPES 2-[4-(2-hydroxyethyl)piperazin-1-yl]ethanesulfonic acid
HFIP hexafluoro isopropanol
HOBt hydroxybenzotriazole
HPLC high pressure liquid chromatography
i-PrOH isopropyl alcohol
H₂O water
K kelvin
KOH potassium hydroxide
LC liquid chromatography
M molar
m multiplet, mass
MeOH methanol
MES 2-(N-morpholino)ethanesulfonic acid
MgSO₄ magnesium sulfate
MHz megahertz
mL milliliter
mm millimeter
mmol millimole
min. minute
mRNA messenger ribonucleic acid
MS mass spectroscopy
mw microwave
m/z mass to charge ratio
NaOH sodium hydroxide
Na₂SO₄ sodium sulfate
NEt₃ triethylamine
NH₃ ammonia
NMR nuclear magnetic resonance
PBS phosphate buffered saline
ppt precipitate
ppm parts per million
rbf round bottom flask
Rf retardation factor
RP reverse phase
RT,rt room temperature
Rt Retention time
s singlet
sat. saturated
SM starting material
t triplet
TBA tributylamine
TEA triethylamine
TEAB triethylammonium bicarbonate
TFA trifluoroacetic acid
THF tetrahydrofuran
TLC thin layer chromatography
TRIS 2-Amino-2-hydroxymethyl-propane-1,3-diol
UPLC ultra performance liquid chromatography
Tris.HCl aminotris(hydroxymethyl)methane hydrochloride
wt weight
Xphos Pd G2 2$^{nd}$ Generation Xphos Precatalyst, Chloro(2-dicyclohexylphosphino-2',4',6'-triisopropyl-1,1'-biphenyl)[2-(2'-amino-1,1'-biphenyl)]palladium(II)
μg microgram
μL microliter Nucleotide trialkylammonium salts were obtained from the corresponding commercially available sodium salts following literature procedures (Y. Thillier, E. Decroly, F. Morvan, B. Canard, J.-J. Vasseur, F. Debart *RNA* 2012, 18, 856-868; GMP Na-salt: Sigma-Aldrich No. G8377; GDP Na-salt: Sigma-Aldrich No. G7127; 2'-deoxy GMP Na-salt: Sigma-Aldrich No. D9500; Inosine 5'-monophosphate Na-salt: Sigma-Aldrich No. 14625; Inosine 5'-diphosphate Na-salt: Sigma-Aldrich No. 14375) or under conditions similar to those described below.

GMP Triethylammonium Salt:

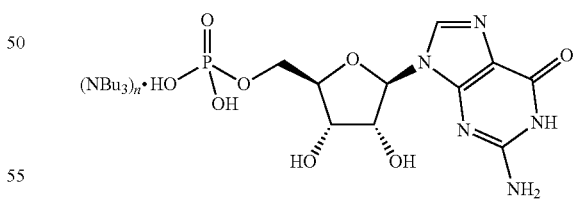

GMP sodium salt (2.0 g, 4.91 mmol) was dissolved RNase free water (40 mL) and passed over DOWEX resin (50WX8, 40 g, rinsed thoroughly with H₂O) into an ice-cooled solution of triethylamine (10 g, 98 mmol) in EtOH (60 mL). The elution was followed by measuring UV absorption of the eluent, and the resin was rinsed with water until no further GMP eluted. The resulting solution was concentrated in vacuum to ca. 500 mL and then lyophilized to obtain the title product as white solid (2.2 g, GMP/TEA ½ judged by ¹H-NMR).

GDP Tributylammonium Salt:

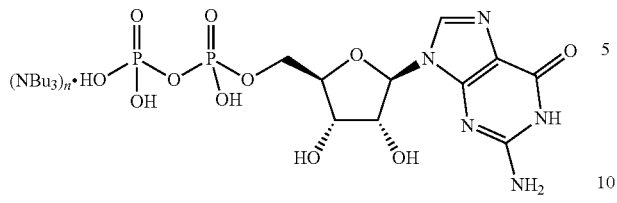

GDP-disodium salt (1.17 g, 2.40 mmol) was dissolved water (100 mL) and passed over DOWEX resin (50WX8, 10 mL, >1.7 meq/mL, rinsed thoroughly with H$_2$O) into an ice-cooled solution of tributylamine (1.34 g, 7.20 mmol) in EtOH (20 mL). The resin was rinsed with water (1000 mL) and the resulting solution was concentrated in vacuum to ca. 500 mL) and then lyophilized to obtain the title product as colorless solid (1.88 g, GDP/TBA 1/2.5 judged by $^1$H-NMR).

General Procedures for N$^7$ Alkylation of GMP

Method A:

In a 2-dram vial, guanosine monophosphate tributylammonium salt (50 mg, 68 umol) was dissolved in DMSO (680 uL) and treated with commercially available alkyl bromide or chloride reagent (4 equiv.). When chloride alkylating reagents were used and in case of the (2-bromoethoxy)-benzene substrates, NaI was added (5 mg, 0.5 eq.). The solution obtained was shaken or stirred at 40° C. for 18 h. The solution obtained was directly subjected to purification by HPLC (reversed phase, H$_2$O+0.1% TFA to MeCN+0.1% TFA 0-100%). Fractions that contained the desired product were pooled, and the solvent was removed by lyophilzation to obtain the pure products as colorless solids or foams.

Method B:

In a 2-dram vial, a 0.1 M solution of GMP or GDP triethyl- or tributylammonium salt in DMSO was treated with the bromide alkylating reagent (4 equiv.). The solution was stirred at room temperature or 55° C. for 18 h and then directly subjected to purification by reversed phase column chromatography (ISCO Teledyne C18 aq. Eluent: 0.1 M triethylammonium bicarbonate (pH=8.0) to MeCN 0-100%). Fractions that contained the desired product were pooled, and the solvent was removed by lyophilzation to obtain the pure products as tributylammonium salts as colorless solids or foams.

Example 1. N-([1,1'-Biphenyl]-4-ylmethyl)-5'-GMP TEA salt

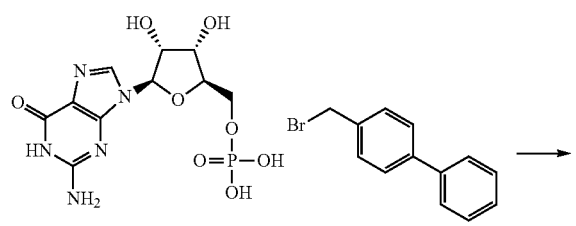

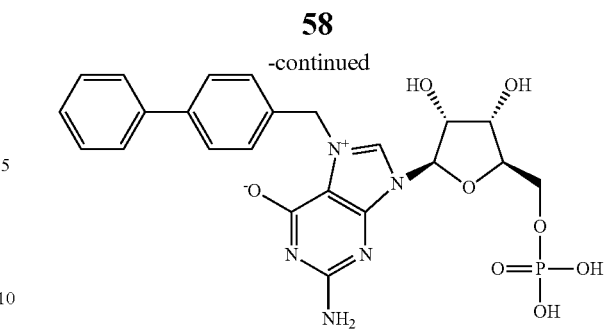

A solution of guanosine monophosphate triethylammonium salt (100 mg, 0.177 mmol) and 4-biphenylmethyl bromide (175 mg, 0.710 mmol) in DMSO (1 mL) was stirred at 55° C. overnight. The solution was directly subjected to purification by reversed phase column chromatography (ISCO Teledyne C18 30 g Gold cartridge, Eluent A: 0.1 M TEAB; B: 20% MeCN in 0.1 M TEAB; Gradient: 0-100% B/A). The product fractions were pooled and lyophilized to give the title compound as white powder (38 mg, 28%). $^1$H NMR (400 MHz, D$_2$O) δ ppm: 7.58-7.67 (4H, m), 7.46-7.53 (4H, m), 7.38-7.46 (1H, m), 5.97-6.03 (1H, m), 5.63-5.76 (2H, m), 4.62-4.69 (1H, m), 4.46-4.52 (1H, m), 4.32-4.40 (1H, m), 3.97-4.18 (2H, m), 3.11-3.25 (8.6H, q), 1.20-1.34 (13H, t). $^{31}$P NMR (162 MHz, D$_2$O): δ ppm: 3.73 (1P). LCMS method 2 R$_t$: 1.39 min, MS [M+H]$^+$ Observed: 529.8. Calculated: 530.1.

Example 2. N$^7$-([1,1'-Biphenyl]-4-ylmethyl)-5'-GDP TEA salt

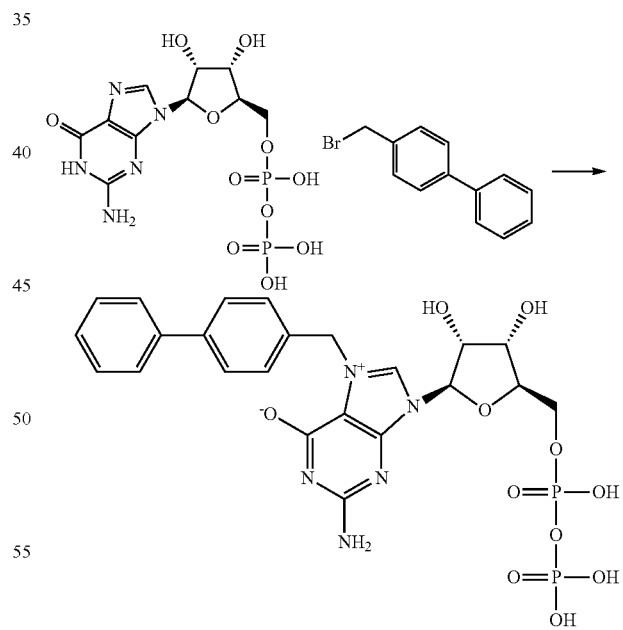

A solution of guanosine diphosphate triethylammonium salt (400 mg, 0.538 mmol) and 4-biphenylmethyl bromide (400 mg, 1.619 mmol) in DMSO (2 mL) was stirred at room temperature overnight. 1M NaClO$_4$ acetone solution (3.23 mL) was added and then diluted with acetone. The precipitate was separated by centrifugation, washed with acetone and dried under vacuum. The solid thus obtained was dissolved in 0.1 M TEAB (5 mL). The resulting solution was subjected to purification by reversed phase column chromatography (ISCO, Teledyne C18, 30 g Gold cartridge, Eluent A: 0.1 M TEAB; B: 90% MeCN in 0.1 M TEAB; Gradient: 0-100% B/A). The product fractions were pooled and lyophilized to give the titled compound as white powder (90 mg, 18%). $^1$H NMR (400 MHz, D$_2$O) δ ppm: 7.57-7.67 (4H, m), 7.39-7.53 (5H, m), 5.92-6.00 (1H, d), 5.64-5.75 (2H, m), 4.67-4.72 (2H, m), 4.56-4.64 (1H, m), 4.34-4.40 (1H, m), 4.26-4.34 (2H, m), 3.12-3.24 (12H, q), 1.27 (18H, t). $^{31}$P NMR (162 MHz, D$_2$O): δ ppm: 7.16 (1P), 10.93 (1P). LCMS method 2 R$_t$: 1.43 min, MS [M−H]$^+$ observed: 608.2, calculated: 608.1.

Example 3. N$^7$-(4-Chlorophenoxyethyl)-5'-GDP TEA salt

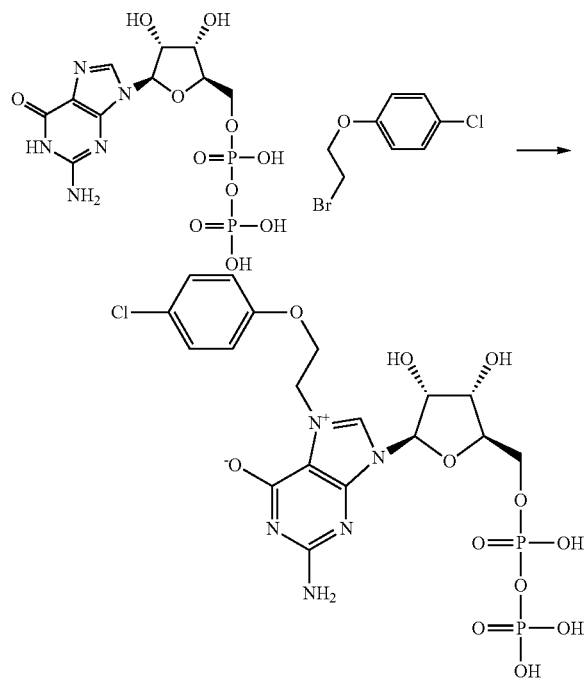

A solution of guanosine diphosphate triethylammonium salt (500 mg, 0.672 mmol) and 4-chlorophenyl 2-bromoethyl ether (633 mg, 2.69 mmol) in DMSO (4 mL) was stirred at 55° C. overnight. 1M NaClO$_4$ acetone solution (4 mL) was added and then diluted with acetone. The precipitate was separated by centrifugation, washed with acetone and dried under vacuum. The solid thus obtained was dissolved in 0.1 M TEAB (5 mL). The resulting solution was subjected to purification by ion exchange chromatography (TOSOH, TSKgel DEAE-5PW, 21.5 mm×15 cm, 13 μm, Eluent A: H$_2$O; B: 1M TEAB in water; Gradient: 0-100% B/A). The product fractions were pooled and lyophilized to give the title compound as white powder (25 mg, 4%). $^1$H NMR (400 MHz, D$_2$O) δ ppm: 7.22-7.31 (2H, d), 6.86-6.94 (2H, d), 5.96-6.03 (1H, m), 4.46-4.52 (1H, m), 4.37-4.44 (1H, m), 4.29-4.37 (1H, m), 4.19-4.29 (2H, m), 3.12-3.26 (9H, q), 1.20-1.34 (16H, t). $^{31}$P NMR (162 MHz, D$_2$O): δ ppm: 9.91 (1P), 11.28 (1P). LCMS method 2 R$_t$: 1.20 min, MS [M−H]$^+$ observed: 596.8, calculated: 596.0.

Example 4. N$^7$-(4-Chlorophenoxyethyl)-5'-GMP TEA salt

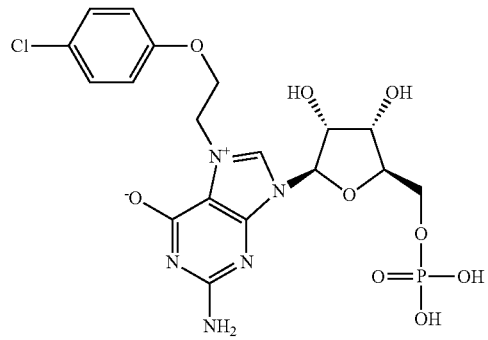

Prepared as described previously (A. R. Kore et al *Bioorg. Med. Chem.* 2013, 21, 4570; Chen et al *J. Med. Chem.* 2012, 55, 3837). The product was obtained as white powder. (84 mg, 12%). $^1$H NMR (400 MHz, D$_2$O) δ ppm: 7.18-7.27 (2H, d), 6.83-6.93 (2H, d), 5.92-6.02 (1H, m), 4.41-4.48 (1H, m), 4.33-4.41 (1H, m), 4.11-4.20 (1H, m), 3.97-4.09 (1H, m), 3.13-3.26 (10H, q), 1.20-1.34 (15H, t). $^{31}$P NMR (162 MHz, D$_2$O): δ ppm: 3.39 (1P). LCMS method 2 R$_t$: 1.20 min, MS [M+H]$^+$ observed: 517.8, calculated: 518.1.

Example 5. N$^7$—Benzyl-5'-GMP TEA Salt

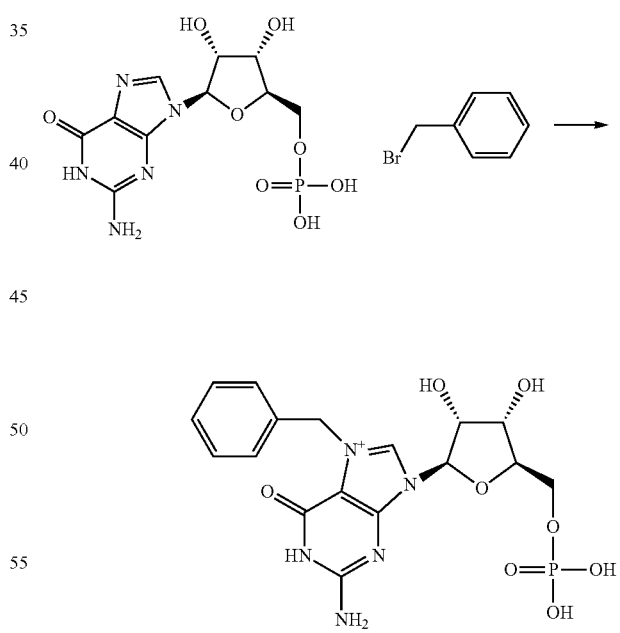

Prepared as described previously (Brown et al *J. Mol Biol.* 2007, 372, 7-15). The product was obtained as white powder (55 mg, 38%). $^1$H NMR (400 MHz, D$_2$O) δ ppm: 7.33-7.45 (5H, m), 6.02-6.11 (1H, m), 5.64-5.73 (2H, m), 4.44-4.53 (1H, m), 4.33-4.42 (1H, m), 3.96-4.17 (2H, m), 3.19 (10H, q), 1.27 (14H, t). $^{31}$P NMR (162 MHz, D$_2$O): δ ppm: 3.78 (1P). LCMS method 2 R$_t$: 0.84 min, MS [M+H]$^+$ observed: 454.2, calculated: 454.1.

Example 6. N⁷-(6-phenylpyridin-3-yl)methyl)-5'-GMP TEA salt

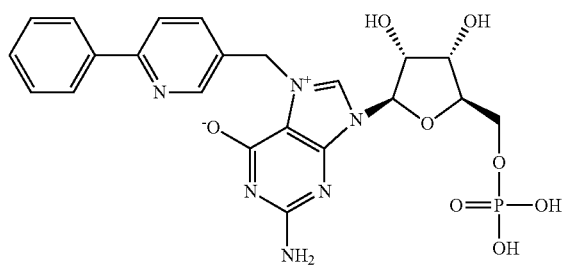

Step 1. 5-(bromomethyl)-2-phenylpyridine

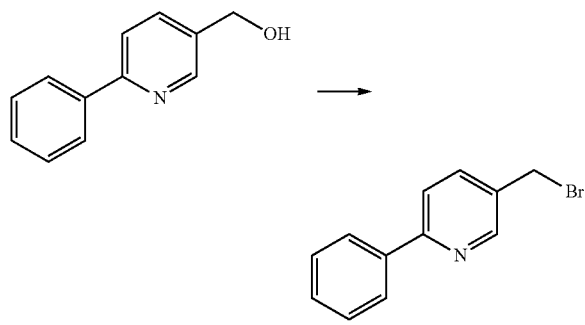

A solution of (6-phenylpyridin-3-yl)methanol (300 mg, 1.620 mmol) in 33% HBr in acetic acid (2.93 mL, 16.20 mmol) was stirred at 40° C. overnight. The volatiles were evaporated. The residue was partitioned between DCM, diluted with sodium bicarbonate solution, and the organic layer was separated. The organic layer was washed with water, dried, and concentrated under vacuum to give a solid (277 mg, 69%). LCMS method 3 $R_t$: 1.36 min, MS [M+H]⁺ observed: 249.9, calculated: 250.0.

Step 2. N⁷-(6-phenylpyridin-3-yl)methyl)-5'-GMP TEA salt

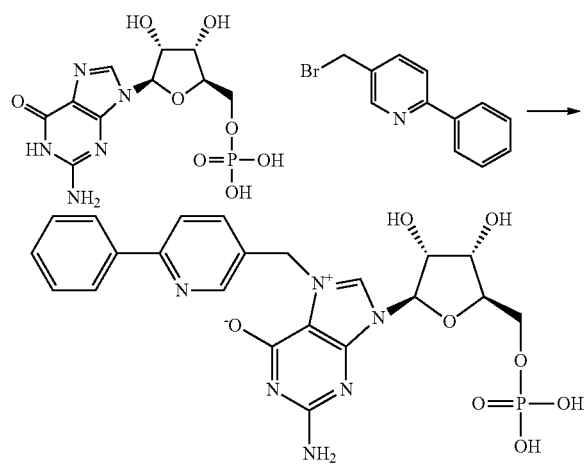

The title compound (40 mg, 23%) was prepared from 130 mg of GMP TEA salts by the method described in Example 5. ¹H NMR (400 MHz, D₂O) δ ppm: 8.57-8.66 (1H, m), 7.85-7.93 (1H, m), 7.66-7.82 (3H, m), 7.39-7.52 (3H, m), 5.91-6.02 (1H, m), 5.58-5.77 (2H, m), 4.42-4.50 (1H, m), 4.28-4.37 (1H, m), 4.06-4.17 (1H, m), 3.95-4.02 (1H, m), 3.06-3.23 (10H, m), 1.11-1.30 (15H, m). ³¹P NMR (162 MHz, D₂O): δ ppm: 3.54 (1P). LCMS method 2 $R_t$: 0.91 min, MS [M+H]⁺ observed: 531.0, calculated: 531.1.

Example 7. N⁷-([1,1'-Biphenyl]-4-ylmethyl)-2',3'-isopropylidene-5'-GMP TEA salt

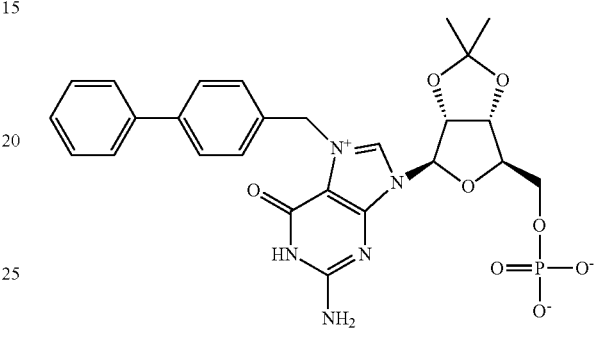

Step 1: N⁷-([1,1'-biphenyl]-4-ylmethyl)-2',3'-isopropylidene guanosine

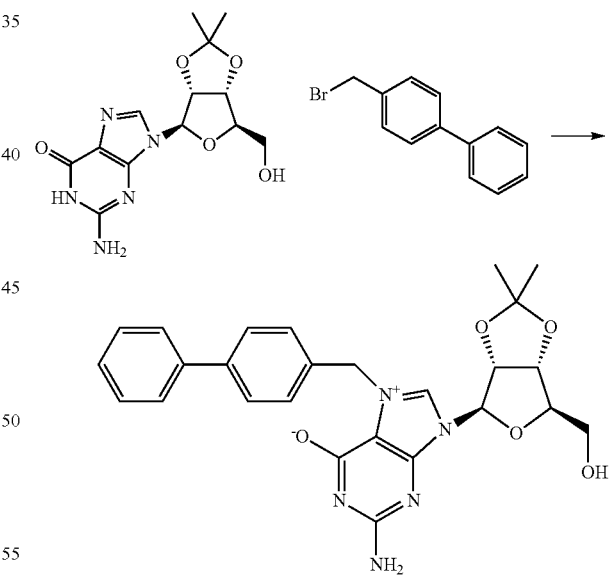

A solution of 2',3'-isopropylidene guanosine (500 mg, 1.547 mmol) and 4-biphenylmethyl bromide (145 mg, 0.849 mmol) in DMSO (2 mL) was stirred at room temperature overnight. The solution was directly subjected to purification by reversed phase HPLC (X-Bridge 50×50 mmm, 5 μm column, Eluent A: water with 5 mM NH₄OH; B MeCN with 5 mM NH₄OH; Gradient: 15-40% B/A). The product fractions were pooled and lyophilized to give the title compound as white powder (260 mg, 34%). LCMS method 1 $R_t$: 1.02 min, MS [M+H]⁺ observed: 490.1, calculated: 490.2.

Step 2: N⁷-([1,1'-Biphenyl]-4-ylmethyl)-2',3'-isopropylidene-5'-GMP TEA salt

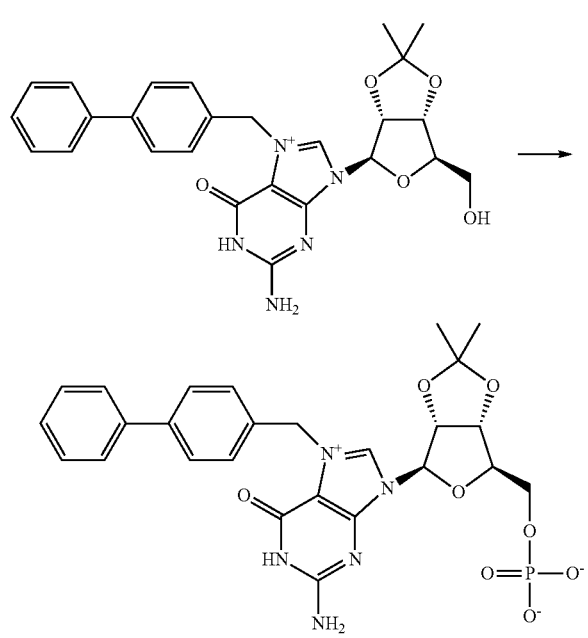

Phosphoryl trichloride (95 μL, 1.021 mmol) was added slowly to a mixture of $N^7$-([1,1'-biphenyl]-4-ylmethyl)-2',3'-isopropylidene guanosine (100 mg, 0.204 mmol) in trimethyl phosphate (1 mL) at 0° C., and stirred under N2 for 3 hrs. The reaction mixture was added dropwise to 1M TEAB solution (3 mL) at 0° C., the resulting mixture was centrifuged. The solution thus obtained was subjected to purification by reversed phase column chromatography (ISCO Teledyne C18 30 g Gold cartridge, Eluent A: 0.1 M TEAB; B: 30% MeCN in 0.1 M TEAB; Gradient: 0-100% B/A). The product fractions were pooled and lyophilized to give the title compound as white powder (38 mg, 24%). $^1$H NMR (400 MHz, D$_2$O) δ ppm: 9.70-9.90 (1H, br), 7.57-7.69 (4H, m), 7.29-7.57 (5H, m), 6.01-6.13 (1H, m), 5.61-5.78 (2H, m), 5.34-5.41 (1H, m), 5.09-5.15 (1H, m), 4.52-4.60 (1H, m), 3.98-4.09 (1H, m), 3.80-3.92 (1H, m), 2.60 (8H, q), 1.50 (3H, s), 1.34 (4H, s), 1.00 (14H, t). $^{31}$C (162 MHz, D$_2$O): δ ppm: 0.224 (1P). LCMS method 4 R$_t$: 0.94 min, MS [M+H]$^+$ observed: 570.1, calculated: 570.2.

Example 8. 7-([1,1'-biphenyl]-4-ylmethyl)-2-amino-9-((2-(phosphonooxy)ethoxy)methyl)-9H-purin-7-ium-6-olate triethyl ammonium salt

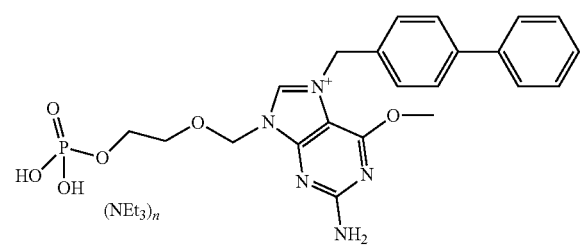 [SMILES: COc1nc(N)nc2c1[n+](Cc1ccc(-c3ccccc3)cc1)cn2COCCOP(=O)(O)O]

Step 1: 7-([1,1'-biphenyl]-4-ylmethyl)-2-amino-9-((2-hydroxyethoxy)methyl)-9H-purin-7-ium-6-olate

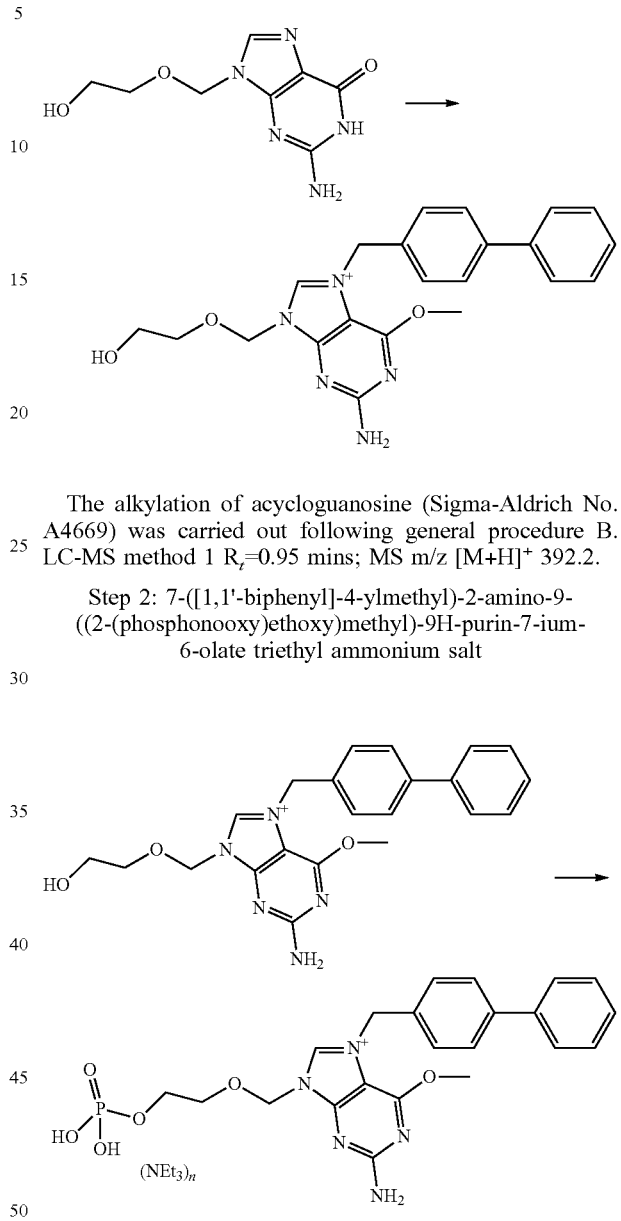

The alkylation of acycloguanosine (Sigma-Aldrich No. A4669) was carried out following general procedure B. LC-MS method 1 R$_t$=0.95 mins; MS m/z [M+H]$^+$ 392.2.

Step 2: 7-([1,1'-biphenyl]-4-ylmethyl)-2-amino-9-((2-(phosphonooxy)ethoxy)methyl)-9H-purin-7-ium-6-olate triethyl ammonium salt The alcohol obtained in step 1 (73 mg, 0.19 mmol) was suspended in PO(OMe)$_3$ (1.9 mL), and POCl$_3$ (86 mg, 0.56 mmol) was added. The solution was stirred for 3 h at rt and then quenched by addition of TEAB (0.1 M, 1 mL). The solution obtained was directly subjected to purification by column chromatography (ISOC RP C18Aq eluting with TEAB 0.1M and MeCN; 0-100% MeCN). After lyophilization of the fractions obtained, the product was obtained as colorless foam (84 mg, 0.14 mmol, 75%, ratio phosphate to NEt$_3$ 1/1.4 as determined by $^1$H-NMR). LC-MS method 6 R$_t$=1.79 mins; MS m/z [M+H]$^+$ 472.1168; calculated: 472.1145, $^1$H NMR (400 MHz, D$_2$O) δ 7.45-7.44 (3H, m), 7.54 (2H, d, J=8.14 Hz), 7.50 (2H, d, J=7.80 Hz), 5.53 (2H, s), 5.50 (2H, s), 3.78-3.74 (2H, m), 3.65-3.62 (2H, m), 3.05 (8.4H, q, J=7.34 Hz, NEt$_3$), 1.13 (12.7H, t, J=7.56 Hz, NEt$_3$).

Example 9. 7-([1,1'-biphenyl]-4-ylmethyl)-2-amino-9-((2-((hydroxy(phosphonooxy)phosphoryl)oxy)ethoxy)methyl)-9H-purin-7-ium-6-olate triethyl ammonium salt

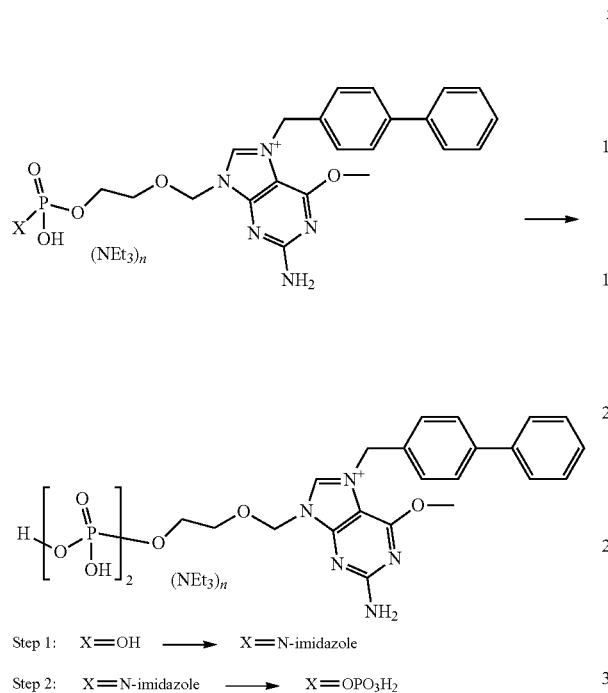

Step 1:   X=OH   ⟶   X=N-imidazole
Step 2:   X=N-imidazole   ⟶   X=OPO$_3$H$_2$

Step 1:

Acycloguanosine phosphate triethylammonium salt (obtained as described above, 77 mg, 0.13 mmol) was suspended in DMF (anhydrous, 6.7 mL) and imidazole (101 mg, 1.48 mmol), 2,2'-dipyridyl disulfide (151 mg, 0.685 mmol), and NEt$_3$ (34 mg, 0.24 mmol) were added. The suspension was stirred for 10 min at rt before triphenylphosphine (183 mg, 0.698 mmol) was added. The reaction mixture turned light yellow and was stirred for 5 h at rt. NaClO$_4$ solution in acetone (1 M, 2.1 mL) and acetone (15 ml) were added and the suspension was kept on ice for 10 min. The resulting solution was centrifuged (3 min, 2000×g) and the pellet was washed twice with 10 mL ice-cold acetone. The pellet was dried under vacuum to obtain the imidazole activated phosphate (50 mg, 0.096 mmol, 71%), which was used without further purification.

Step 2:

The activated phosphate obtained in step 1 was suspended in DMF (0.5 mL), and tributylammonium phosphate (1.0 M in DMF, 0.5 mL, 0.479 mmol) and ZnCl$_2$ (13 mg, 0.096 mmol) were added. The solution was stirred vigorously at rt for 5 h and then directly subjected to purification by column chromatography on ISCO RPAq18 eluting with 0.1 M TEAB and MeCN, 0 to 100% MeCN. Lyophilization of the product containing fractions gave the title product as colorless solid (52 mg, 0.065 mmol, 68%, ratio of phosphate to NEt$_3$ 1/2.45 as determined by $^1$H NMR). LC-MS: R$_t$=0.99 mins; MS m/z [M+H]$^+$ 552.1 LCMS method 1; $^1$H NMR (400 MHz, D$_2$O) δ 7.59-7.54 (4H, m), 7.40-7.36 (4H, m), 7.32-7.28 (1H, m), 5.58 (2H, s), 5.55 (2H, s), 3.98-3.94 (2H, m), 3.73-3.71 (2H, m), 3.08 (q, J=7.22 Hz, NEt$_3$), 1.13 (12.7H, t, J=7.56 Hz, NEt$_3$).

Example 10. 7-((2-chloro-[1,1'-biphenyl]-4-yl)methyl)-5'-GDP TEA salt

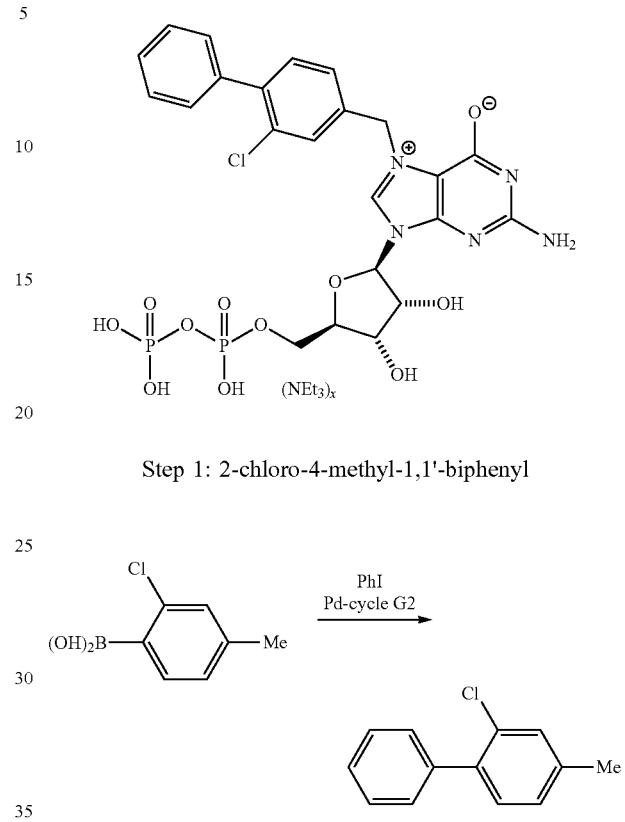

Step 1: 2-chloro-4-methyl-1,1'-biphenyl

In a 2 dram vial, phenyl iodide (200 mg, 0.98 mmol) and (2-chloro-4-methylphenyl)boronic acid (167 mg, 0.98 mmol) were dissolved in DMF (4.9 mL). An aqueous solution of K$_2$CO$_3$ (542 mg in 400 µL H$_2$O) and Sphos Palladacycle G2 (7.1 mg, 9.8 µmol) was added, and the resulting suspension was stirred vigorously at 80° C. for 3 h. After cooling to room temperature, DCM (5 mL) was added, and the organic layer was washed with water (10 mL), 10% LiCl (aq., 3×10 mL), and dried over Na$_2$SO$_4$. The residue obtained after removal of the solvent in vacuo was subjected to purification by flash chromatography (SiO$_2$, heptane to 20% EtOAc in heptane). 2-Chloro-4-methyl-1,1'-biphenyl was obtained as colorless oil (147 mg, 0.725 mmol, 74%). $^1$H NMR (400 MHz, CDCl$_3$) δ 7.45-7.44 (3H, m), 7.41-7.36 (1H, m), 7.32 (1H, br s), 7.25 (1H, d, J=7.58 Hz), 7.14 (1H, d, J=7.58 Hz), 2.40 (3H, s).

Step 2: 4-(bromomethyl)-2-chloro-1,1'-biphenyl

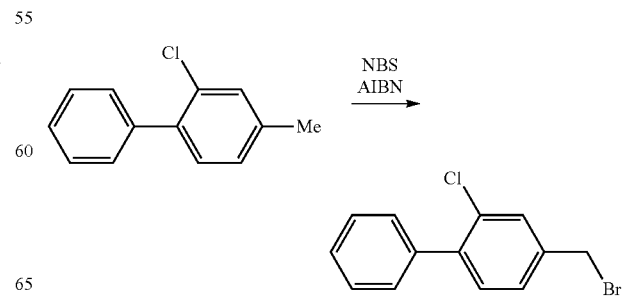

2-Chloro-4-methyl-1,1'-biphenyl (140 mg, 0.691 mmol), N-bromo succinimide (135 mg, 0.760 mmol), and azodi-isobutyro nitrile (11 mg, 0.069 mmol) were dissolved in CCl₄ (6.9 mL), and the solution was stirred at 85° C. for 1 h. The solvent was removed under vacuum and the residue was purified by flash chromatography (SiO₂, heptane to 20% EtOAc in heptane) to obtain the title compound in a mixture with starting material (3:1, judged by 1H NMR) as colorless solid (173 mg, 0.406 mmol, 66%). The mixture was used as such in the subsequent alkylation reaction.

Step 3: 7-((2-chloro-[1,1'-biphenyl]-4-yl)methyl)-5'-GDP TEA salt

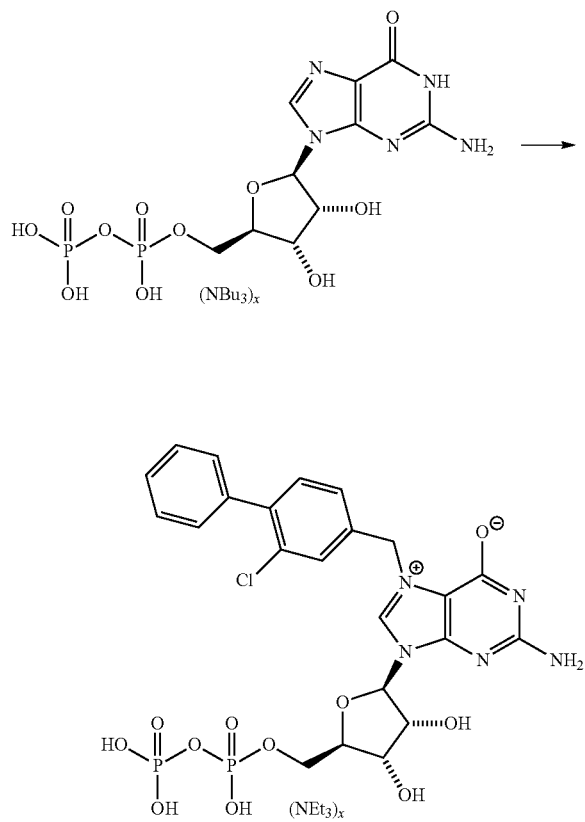

GDP tributylammonium salt (70 mg, 0.086 mmol) was alkylated with the product of step 2 (73 mg, 0.26 mmol) following the general procedure B. The title product was obtained as colorless solid (30 mg, 0.036 mmol, 42%). LCMS method 1: R$_t$=1.01 mins; MS m/z [M+H]⁺ 644.0; ¹H NMR (400 MHz, DMSO-d₆) δ 10.42 (1H, s), 7.93 (1H, s), 7.78 (1H, d, J=8.12 Hz), 7.72-7.63 (1H, m), 7.47-7.35 (9H, m), 5.81 (1H, s), 5.72 (1H, br s), 4.48 (1H, br s), 4.40 (1H, br s), 4.14-4.04 (3H, m), 3.34 (br, NEt₃), 1.03 (12.7H, t, J=7.56 Hz, NEt₃).

Example 11. 7-((3-methoxy-[1,1'-biphenyl]-4-yl)methyl)-5'-GDP TEA salt

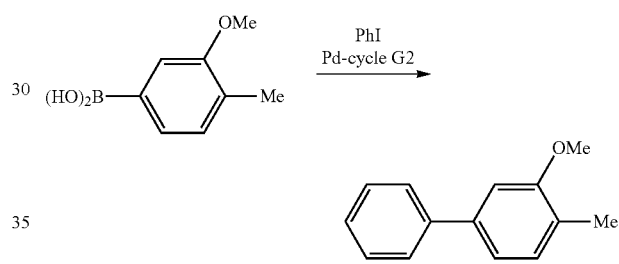

Step 1: 3-methoxy-4-methyl-1,1'-biphenyl

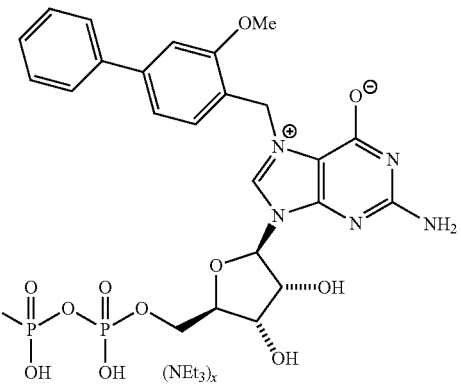

In a 2 dram vial, phenyl iodide (200 mg, 0.98 mmol) and (3-methoxy-4-methylphenyl)boronic acid (163 mg, 0.98 mmol) were dissolved in DMF (4.9 mL). An aqueous solution of K₂CO₃ (542 mg in 400 μL H₂O) and Sphos Palladacycle G2 (7.1 mg, 9.8 μmol) was added, and the resulting suspension was stirred vigorously at 80° C. for 12 h. After cooling to room temperature, DCM (5 mL) was added, and the organic layer was washed with water (10 mL), 10% LiCl (aq., 3×10 mL), and dried over Na₂SO₄. The residue obtained after removal of the solvent in vacuo was subjected to purification by flash chromatography (SiO₂, heptane to 20% EtOAc in heptane). 3-Methoxy-4-methyl-1,1'-biphenyl was obtained as colorless oil (149 mg, 0.752 mmol, 77%). ¹H NMR (400 MHz, DMSO-d₆) δ 7.70-7.66 (2H, m), 7.53-7.49 (2H, m), 7.44-7.39 (1H, m), 7.28 (1H, d, J=7.04 Hz), 7.19 (1H, dd, J=7.60, 1.77 Hz), 7.13 (1H, d, J=1.50 Hz), 3.97 (3H, s), 2.37 (3H, s).

Step 2: 4-(bromomethyl)-3-methoxy-1,1'-biphenyl

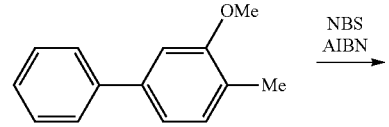

-continued

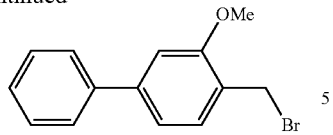

3-methoxy-4-methyl-1,1'-biphenyl (147 mg, 0.741 mmol), N-bromo succinimide (145 mg, 0.816 mmol), and azodiisobutyro nitrile (12 mg, 0.074 mmol) were dissolved in CCl$_4$ (7.4 mL), and the solution was stirred at 85° C. for 1 h. The solvent was removed under vacuum and the residue was purified by flash chromatography (SiO$_2$, heptane to 20% EtOAc in heptane) to obtain the title compound as colorless solid (163 mg, 0.588 mmol, 79%). $^1$H NMR (400 MHz, CDCl$_3$) δ 7.62-7.59 (2H, m), 7.49-7.45 (2H, m), 7.43-7.39 (2H, m), 7.18 (1H, dd, J=7.75, 1.66 Hz), 7.11 (1H, d, J=1.59 Hz), 4.65 (2H, s), 3.99 (3H, s).

Step 3: 7-((3-methoxy-[1,1'-biphenyl]-4-yl)methyl)-5'-GDP TEA salt

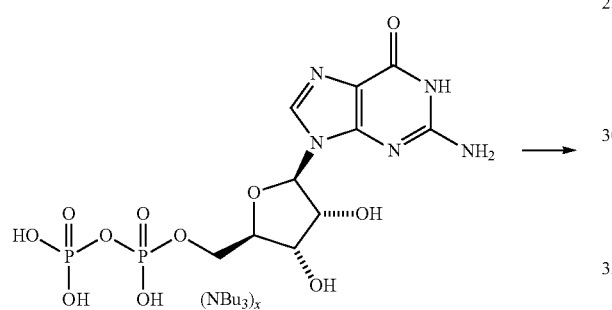

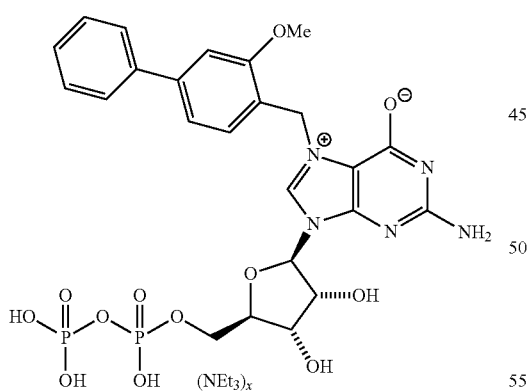

GDP tributylammonium salt (100 mg, 0.123 mmol) was alkylated with the product of step 2 (102 mg, 0.369 mmol) following the general procedure B. The title product was obtained as colorless solid (46 mg, 0.056 mmol, 45%). LCMS method 1 R$_t$=0.99 mins; MS m/z [M+H]$^+$640.0; $^1$H NMR (400 MHz, DMSO-d6) δ 9.80 (1H, s), 7.66 (2H, d, J=7.49 Hz), 7.47-7.43 (3H, m), 7.38-7.34 (1H, m), 7.21 (1H, br s), 7.15 (1H, d, J=7.59 Hz), 5.83 (1H, s), 5.56 (2H, s), 4.48 (2H, s), 4.14 (1H, br s), 4.06 (1H, br s), 3.95 (3H, s), 2.68 (br, NEt$_3$), 1.04 (t, J=6.81 Hz, NEt$_3$).

Example 12. 7-(6-phenylpyridin-2(1H)-one-3-yl)-5'-GDP TEAsalt

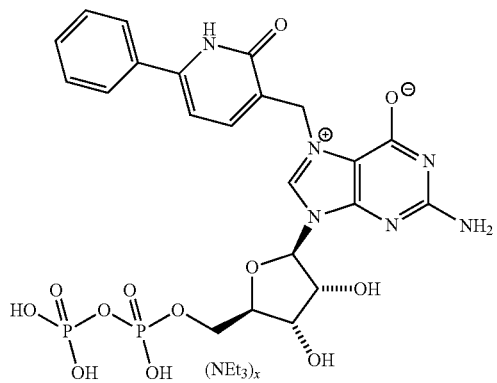 [SMILES: Nc1nc([O-])c2c(n1)n([C@@H]1O[C@H](COP(=O)(O)OP(=O)(O)O)[C@@H](O)[C@H]1O)c[n+]2Cc1ccc(-c2ccccc2)[nH]c1=O]

Step 1: 3-(hydroxymethyl)-6-phenylpyridin-2(1H)-one

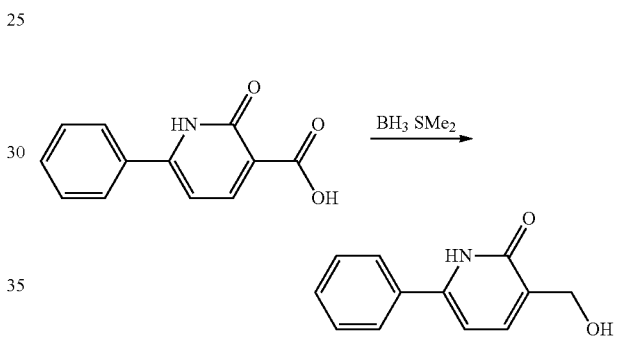

To a solution of 2-oxo-6-phenyl-1,2-dihydropyridine-3-carboxylic acid (533 mg, 2.48 mmol) in THF (24 mL) was added borane dimethylsulfide complex (1.0 M in THF, 991 µL, 9.91 mmol), and the suspension was stirred at room temperature for 18 h. MeOH was slowly added until gas evolution ceased. The resulting solution was partitioned between EtOAc and brine, and the organic layer was dried over NaSO$_4$. Removal of the solvent under vacuum and purification of the residue by flash chromatography (SiO$_2$, DCM to 5% MeOH in DCM) gave the title compound as pale yellow solid (331 mg, 1.65 mmol, 66%). LCMS method 1 R$_t$=0.89 mins; MS m/z [M-OH-]$^+$183.6.

Step 2: 3-(bromomethyl)-6-phenylpyridin-2(1H)-one

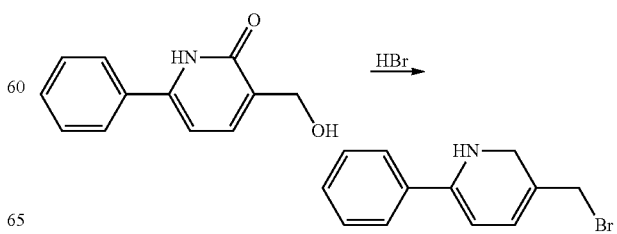

3-(hydroxymethyl)-6-phenylpyridin-2(1H)-one (331 mg, 1.65 mmol) was treated with HBr (aq. 48%, 16.5 mL), and the suspension was stirred at room temperature for 1 h and then at 60° C. for 1 h. During this time the suspension first clears, and then a precipitate is formed. The precipitate is filtered, washed thoroughly with water, and dried in vacuum to give 3-(bromomethyl)-6-phenylpyridin-2(1H)-one as colorless powder (388 mg, 1.469 mmol, 89%). $^1$H NMR (400 MHz, DMSO-d6) δ 7.08-7.74 (4H, m), 7.55-7.51 (3H, m), 7.50-7.46 (1H, m), 5.28 (2H, s).

Step 3: 7-(6-phenylpyridin-2(1H)-one-3-yl)-5'-GDP TEA salt

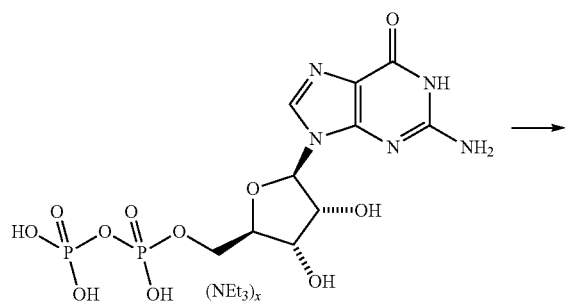

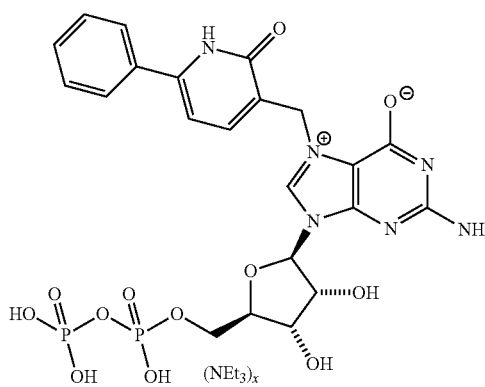

GDP tributylammonium salt (100 mg, 0.123 mmol) was alkylated with the product of step 2 (102 mg, 0.369 mmol) following the general procedure B. The title product was obtained as colorless solid (46 mg, 0.056 mmol, 45%). LCMS method 1 $R_t$=0.73 mins; MS m/z [M+H]$^+$627.1; $^1$H NMR (400 MHz, DMSO-d6) δ 9.7 (1H, s), 7.78-7.76 (2H, m), 7.63 (1H, d, J=7.33 Hz), 7.47-7.55 (5H, m), 6.69 (1H, d, J=7.33 Hz), 5.82 (1H, d, J=2.04 Hz), 5.45 (2H, s), 4.47 (1H, br), 4.40 (1H, dd, J=5.48 Hz), 4.13 (1H, br), 4.08 (1H, br), 4.03 (1H, br), 3.35 (br, NEt$_3$), 1.05 (t, J=6.49 Hz, NEt$_3$).

Example 13. 7-(3,5-dimethylbenzyl)-5'-GDP TEA salt

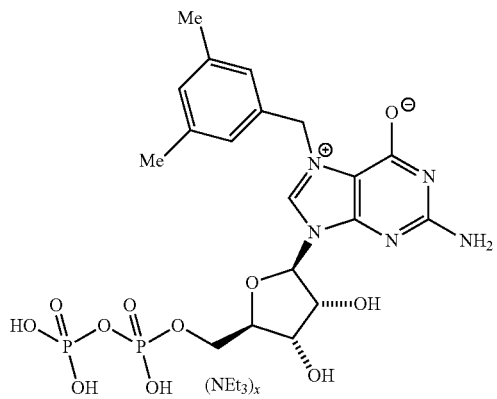 [SMILES: Cc1cc(C)cc(C[n+]2cn([C@@H]3O[C@H](COP(=O)(O)OP(=O)(O)O)[C@@H](O)[C@H]3O)c3nc(N)nc([O-])c32)c1]

GDP tributylammonium salt (150 mg, 0.184 mmol) was alkylated with 3,5-dimethylbenzyl bromide (110 mg, 0.553 mmol) following the general procedure B. The title product was obtained as colorless solid (66 mg, 0.090 mmol, 49%). LCMS method 1 $R_t$=0.80 mins; MS m/z [M+H]$^+$ 561.9; $^1$H NMR (400 MHz, DMSO-d6) δ 10.38 (1H, s), 8.20 (1H, d, J=7.48 Hz), 7.95 (1H, d, J=8.73 Hz), 7.65-7.58 (1H, m), 5.81 (2H, br s), 4.44 (1H, br s), 4.38 (1H, br s), 4.13-4.04 (2H, m), 2.69 (br, NEt$_3$), 1.05 (t, J=6.49 Hz, NEt$_3$).

Example 14. 7-(3-fluorobenzyl)-guanosine-5'-GDP TEA Salt

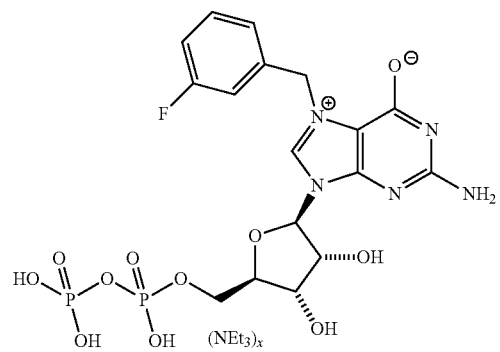 [SMILES: Nc1nc([O-])c2c(n1)n([C@@H]1O[C@H](COP(=O)(O)OP(=O)(O)O)[C@@H](O)[C@H]1O)c[n+]2Cc1cccc(F)c1]

GDP tributylammonium salt (150 mg, 0.184 mmol) was alkylated with 3-fluorobenzyl bromide (105 mg, 0.553 mmol) following the general procedure B. The title product was obtained as colorless solid (40 mg, 0.055 mmol, 30%). LCMS method 1: $R_t$=0.59 mins; MS m/z [M+H]$^+$ 551.9; $^1$H NMR (400 MHz, DMSO-d$_6$) δ 10.38 (1H, s), 7.61 (1H, d, J=9.96 Hz), 7.54 (1H, d, J=7.87 Hz), 7.38 (1H, dd, J=14.50, 7.44 Hz), 5.79 (1H, d, J=1.82 Hz), 5.66 (1H, br s), 4.45 (1H, br s), 4.39 (1H, br s), 4.11-4.05 (2H, m), 2.73 (br, NEt$_3$), 1.05 (t, J=6.49 Hz, NEt$_3$).

Example 15. 7-((3-fluoro-[1,1'-biphenyl]-4-yl)methyl)-5'-GDP TEA salt

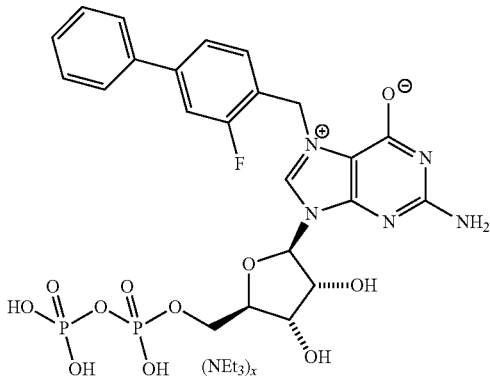 [SMILES: Nc1nc([O-])c2c(n1)n([C@@H]1O[C@H](COP(=O)(O)OP(=O)(O)O)[C@@H](O)[C@H]1O)c[n+]2Cc1ccc(-c2ccccc2)cc1F]

Step 1: 3-Fluoro-4-methyl-1,1'-biphenyl

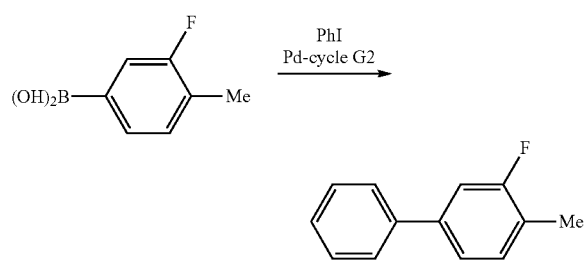

In a 2 dram vial, phenyl iodide (800 mg, 3.92 mmol) and (3-fluoro-4-methylphenyl)boronic acid (604 mg, 3.92 mmol) were dissolved in DMF (19.6 mL). An aqueous solution of $K_2CO_3$ (2.17 g in 1.9 mL $H_2O$) and Sphos Palladacycle G2 (28.3 mg, 39.0 μmol) was added, and the resulting suspension was stirred vigorously at 80° C. for 16 h. After cooling to room temperature, DCM (15 mL) was added, and the organic layer was washed with water (10 mL), 10% LiCl (aq., 3×10 mL), and dried over $Na_2SO_4$. The residue obtained after removal of the solvent in vacuo was subjected to purification by flash chromatography ($SiO_2$, heptane to 20% EtOAc in heptane). 3-Fluoro-4-methyl-1,1'-biphenyl was obtained as colorless oil (746 mg, 3.61 mmol, 91%, 90% purity). $^1$H NMR (400 MHz, DMSO-d6) δ 7.69-7.66 (2H, m), 7.48-7.36 (6H, m), 2.27 (3H, d, J=1.68 Hz).

Step 2: 4-(bromomethyl)-3-fluoro-1,1'-biphenyl

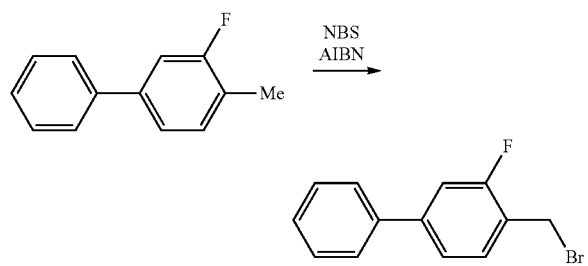

3-Fluoro-4-methyl-1,1'-biphenyl (300 mg, 1.611 mmol), N-bromo succinimide (315 mg, 1.77 mmol), and azodiisobutyro nitrile (26.5 mg, 0.161 mmol) were dissolved in $CCl_4$ (16 mL), and the solution was stirred at 85° C. for 1 h. The solvent was removed under vacuum and the residue was purified by flash chromatography ($SiO_2$, heptane to 20% EtOAc in heptane) to obtain the title compound as pale yellow solid (311 mg, 1.17 mmol, 72%). $^1$H NMR (400 MHz, DMSO-d6) δ 7.74-7.71 (2H, m), 7.62 (1H, d, J=7.92 Hz), 7.57 (1H, dd, J=11.47, 1.70 Hz), 7.53 (1H, dd, J=7.92, 1.60 Hz), 7.51-7.46 (2H, m), 7.43-7.38 (1H, m).

Step 3: 7-((3-fluoro-[1,1'-biphenyl]-4-yl)methyl)-5'-GDP TEA salt

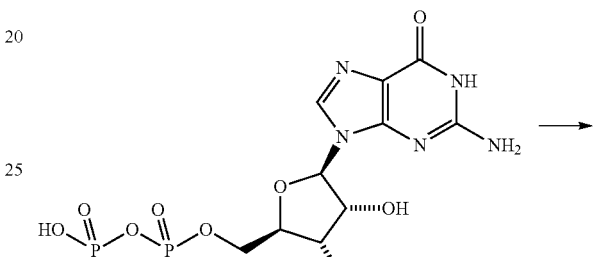

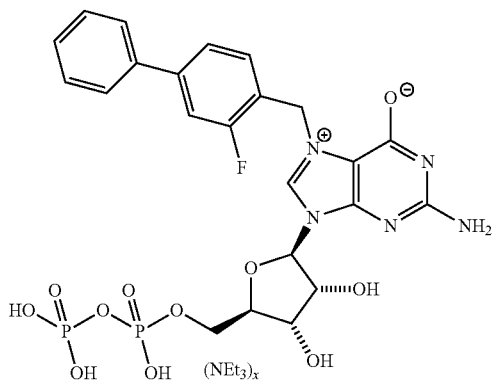

GDP tributylammonium salt (150 mg, 0.184 mmol) was alkylated with the bromide obtained in step 2 (147 mg, 0.553 mmol) following the general procedure B. The title product was obtained as colorless solid (45 mg, 0.056 mmol, 30%). LCMS method 1 $R_t$=0.96 mins; MS m/z [M+H]$^+$ 627.9; $^1$H NMR (400 MHz, DMSO-d6) δ 10.13 (1H, s), 7.69-7.67 (2H, m), 7.55-7.50 (2H, m), 7.48-7.44 (3H, m), 7.41-7.38 (1H, m), 5.84-5.78 (2H, m), 4.46-4.43 (2H, m), 4.11-4.06 (2H, m), 2.75 (br, NEt$_3$), 1.05 (t, J=6.49 Hz, NEt$_3$).

Example 16. 7-(benzhydryl)-guanosine-5'-GDP TEA Salt

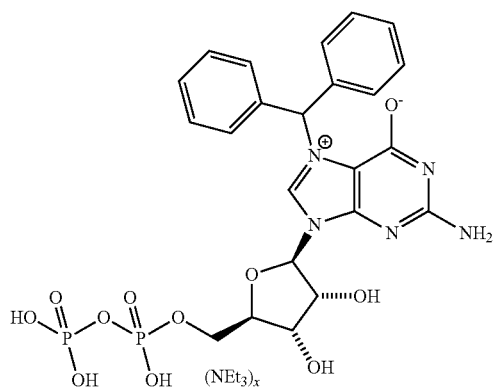 [SMILES: Nc1nc([O-])c2c(n1)n([C@@H]1O[C@H](COP(=O)(O)OP(=O)(O)O)[C@@H](O)[C@H]1O)c[n+]2C(c1ccccc1)c1ccccc1]

GDP tributylammonium salt (150 mg, 0.184 mmol) was alkylated with benzhydryl bromide (91 mg, 0.369 mmol) following the general procedure B. The title product was obtained as colorless solid (20 mg, 0.021 mmol, 30%). LCMS method 1 $R_t$=0.90 mins; MS m/z [M+H]$^+$610.1; $^1$H NMR (400 MHz, DMSO-d6) δ 7.53-7.47 (2H, m), 7.44-7.29 (8H, m), 5.86 (1H, d, J=4.62 Hz), 5.82 (1H, d, J=4.32), 4.72 (1H, br s), 4.48-4.40 (1H, br s), 4.20-4.02 (3H, m), 3.98-3.92 (2H, m), 2.62 (br, NEt$_3$), 1.00 (t, J=6.49 Hz, NEt$_3$).

Example 17. 7-((1-(5-methyl-1,2,4-oxadiazol-3-yl) phenyl 4-yl)methyl)-5'-GDP TEA salt

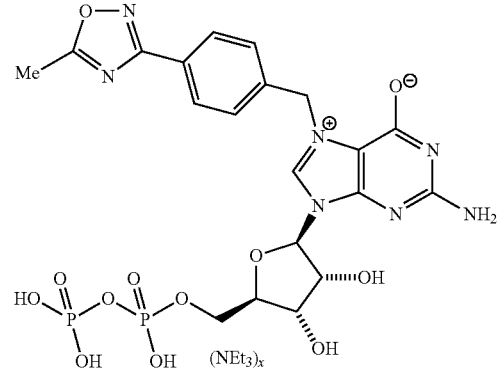 [SMILES: Cc1nc(-c2ccc(C[n+]3cn([C@@H]4O[C@H](COP(=O)(O)OP(=O)(O)O)[C@@H](O)[C@H]4O)c4nc(N)nc([O-])c43)cc2)no1]

Analytical data for N$^7$-alkylated GMP derivatives are presented in Table 1. The following analogs were prepared similarly by general methods A or B or analogously to the methods described in Examples 1-17.

TABLE 1

Analytical data for N$^7$-alkylated GMP derivatives.

| No. | —Y—R$^1$ | R$^3$ | R$^4$ | Synthetic method | LCMS method | $R_t$ min | Calc. mass [M + H]$^+$ | Exp. Mass [M + H]$^+$ |
|---|---|---|---|---|---|---|---|---|
| 1 | propyloxy-phenyl-ethyl | H | OH | A | 2 | 1.43 | 512.15 | 512.2 |
| 2 | propyloxy-phenyl-OMe | H | OH | A | 7 | 0.71 | 514.1 | 514.5 |
| 3 | propyloxy-phenyl-CF$_3$ | H | OH | A | 2 | 1.51 | 552.1 | 552.1 |
| 4 | propyloxy-phenyl-methyl | H | OH | A | 2 | 1.23 | 498.1 | 498.4 |

TABLE 1-continued

Analytical data for N7-alkylated GMP derivatives.

| No. | —Y—R$^1$ | R$^3$ | R$^4$ | Synthetic method | LCMS method | R$_t$ min | Calc. mass [M + H]$^+$ | Exp. Mass [M + H]$^+$ |
|---|---|---|---|---|---|---|---|---|
| 5 | propoxy-(3-methylphenyl) | H | OH | A | 2 | 1.47 | 498.1 | 498.1 |
| 6 | propoxy-(4-chlorophenyl) | Me | OH | A | 2 | 1.35' | 532.8 | 533.0 |
| 7 | propoxy-(4-chlorophenyl) | H | OMe | A | 2 | 1.31' | 532.8 | 533.1 |
| 8 | propoxy-(4-fluorophenyl) | H | OH | A | 2 | 1.12 | 502.1 | 502.2 |
| 9 | (2-bromo-4-ethylthiophene) | H | OH | A | 2 | 1.41 | 538.0 | 539.9 |
| 10 | ethyl-(4-iodophenyl) | H | OH | B | 2 | 1.17 | 579.2 | 579.8 |
| 11 | ethyl-[3-(4-fluorophenoxy)phenyl] | H | OH | A | 6 | 1.70' | 564.1290 | 564.1311 |
| 12 | ethyl-(3-phenoxyphenyl) | H | OH | A | 6 | 1.62' | 546.1384 | 546.1390 |

TABLE 1-continued

Analytical data for N⁷-alkylated GMP derivatives.

| No. | —Y—R¹ | R³ | R⁴ | Synthetic method | LCMS method | R$_t$ min | Calc. mass [M + H]⁺ | Exp. Mass [M + H]⁺ |
|---|---|---|---|---|---|---|---|---|
| 13 | 4-ethylbenzoate methyl ester | H | OH | A | 6 | 0.75' | 512.1177 | 512.1195 |
| 14 | 3-fluorophenethyl | H | OH | A | 6 | 0.72' | 472.1034 | 472.0985 |
| 15 | 4-cyanophenethyl | H | OH | A | 6 | 0.52' | 479.1075 | 479.1103 |
| 16 | methyl 3-(3-ethylbenzamido)thiophene-2-carboxylate | H | OH | A | 6 | 1.72' | 637.1112 | 637.1117 |
| 17 | methyl 2-(3-ethylbenzamido)thiophene-3-carboxylate | H | OH | A | 6 | 1.75' | 637.1112 | 637.1146 |
| 18 | 3-(benzyloxymethyl)phenethyl | H | OH | A | 6 | 1.68' | 560.1541 | 560.1544 |
| 19 | 2-ethylthiazole | H | OH | A | 2 | 0.61 | 460.1 | 460.9 |

TABLE 1-continued
Analytical data for N[7]-alkylated GMP derivatives.
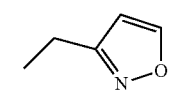
| No. | —Y—R[1] | R[3] | R[4] | Synthetic method | LCMS method | $R_t$ min | Calc. mass $[M + H]^+$ | Exp. Mass $[M + H]^+$ |
|---|---|---|---|---|---|---|---|---|
| 20 | 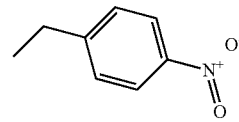 | H | OH | A | 2 | 0.68 | 445.0867 | — |
| 21 | 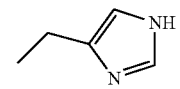 | H | OH | A | 6 | 0.64 | 499.0973 | 499.0975 |
| 22 | 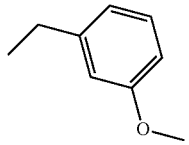 | H | OH | A | 2 | 0.67 | 458.1 | 458.9 |
| 23 | 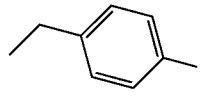 | H | OH | A | 6 | 0.80' | 484.1228 | 484.1217 |
| 24 | 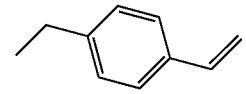 | H | OH | A | 6 | 1.21' | 500.0999 | 500.0981 |
| 25 | 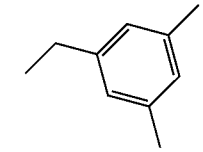 | H | OH | A | 6 | 1.06' | 480.1279 | 480.1281 |
| 26 | 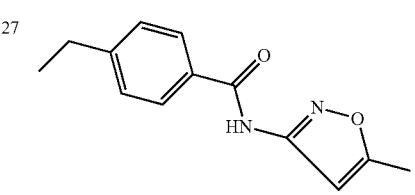 | H | OH | A | 6 | 1.20' | 482.1435 | 482.1461 |
| 27 |  | H | OH | A | 6 | 0.91' | 578.1395 | 578.1382 |

TABLE 1-continued

Analytical data for N[7]-alkylated GMP derivatives.

| No. | —Y—R[1] | R[3] | R[4] | Synthetic method | LCMS method | $R_t$ min | Calc. mass [M + H]+ | Exp. Mass [M + H]+ |
|---|---|---|---|---|---|---|---|---|
| 28 | diphenylethyl | H | OH | B | 6 | 1.44' | 530.1435 | 530.1442 |
| 29 | (4-ethyl-3-phenylisoxazol-5-yl)methyl | H | OH | A | 2 | 1.42 | 535.1 | 535.1 |
| 30 | 4-ethylbenzoic acid | H | OH | A | 2 | 0.50 | 498.1 | 498.1 |
| 31 | 4-ethylphenylacetic acid | H | OH | A | 2 | 1.05 | 512.1 | 512.1 |
| 32 | methyl 5-ethylfuran-2-carboxylate | H | OH | A | 2 | 0.83 | 502.1 | 501.9 |
| 33 | 4-(trifluoromethyl)ethylbenzene | H | OH | A | 6 | 1.20' | 522.0996 | 522.1002 |
| 34 | 4-tert-butylethylbenzene | H | OH | A | 6 | 1.67' | 510.1748 | 510.1759 |

TABLE 1-continued

Analytical data for N⁷-alkylated GMP derivatives.

| No. | —Y—R¹ | R³ | R⁴ | Synthetic method | LCMS method | $R_t$ min | Calc. mass $[M + H]^+$ | Exp. Mass $[M + H]^+$ |
|---|---|---|---|---|---|---|---|---|
| 35 | 2,6-dichlorobenzyl | H | OH | A | 6 | 0.90' | 522.0343 | 522.0334 |
| 36 | 4-(benzyloxy)benzyl | H | OH | A | 6 | 1.74' | 560.1541 | 560.1552 |
| 37 | 3-(trifluoromethoxy)benzyl | H | OH | A | 6 | 1.30' | 538.0945 | 538.0955 |
| 38 | 3,5-dimethoxybenzyl | H | OH | A | 6 | 0.96' | 514.1334 | 514.1344 |
| 39 | 2-((phenylsulfonyl)methyl)benzyl | H | OH | A | 6 | 1.20' | 608.1211 | 608.1221 |
| 40 | 3,4-bis(benzyloxy)benzyl | H | OH | A | 6 | 2.46' | 666.1960 | 666.1987 |

TABLE 1-continued

Analytical data for N[7]-alkylated GMP derivatives.

| No. | —Y—R[1] | R[3] | R[4] | Synthetic method | LCMS method | R$_t$ min | Calc. mass [M + H]+ | Exp. Mass [M + H]+ |
|---|---|---|---|---|---|---|---|---|
| 41 | 4-ethylphenyl benzoate 2,6-dichlorophenyl ester | H | OH | A | 6 | 2.05' | 642.0554 | 642.0544 |
| 42 | MeO, ethyl-biphenyl | H | OH | B | 6 | 1.86' | 560.1541 | 560.1520 |
| 43 | ethyl-pyridinone-phenyl | H | OH | B | 6 | 1.03' | 547.1337 | 547.1345 |
| 44 | ethyl-chlorobiphenyl | H | OH | B | 6 | 1.92' | 564.1046 | 564.1058 |
| 45 | F, ethyl-fluorobiphenyl | H | OH | B | 6 | 1.77' | 548.1341 | 548.1339 |
| 46 | Me, ethyl-methylbiphenyl | H | OH | B | 6 | 1.91' | 544.1592 | 544.1557 |
| 47 | F, ethyl-fluorobiphenyl | H | OH | A | 8 | 0.73 | 548.1 | 548.3 |

TABLE 1-continued

Analytical data for N⁷-alkylated GMP derivatives.

| No. | —Y—R¹ | R³ | R⁴ | Synthetic method | LCMS method | R$_t$ min | Calc. mass [M + H]⁺ | Exp. Mass [M + H]⁺ |
|---|---|---|---|---|---|---|---|---|
| 48 | (ethyl-phenyl-1,2,4-triazole) | H | OH | A | 6 | 0.49' | 521.1293 | 521.1323 |
| 49 | (ethyl-phenyl-thiophene) | H | OH | A | 1 | 1.09 | 536.1 | 536.3 |
| 50 | (ethyl-phenyl-pyrazole) | H | OH | B | 2 | 0.98' | 520.1 | 519.9 |
| 51 | (ethyl-phenyl-cyclohexyl) | H | OH | B | 2 | 1.65' | 536.2 | 535.9 |
| 52 | (ethyl-phenyl-thiadiazole) | H | OH | A | 6 | 0.82' | 538.0904 | 538.0918 |
| 53 | (ethyl-phenyl-benzoyl) | H | OH | A | 6 | 1.34' | 558.1384 | 558.140 |
| 54 | (ethyl-thiazole-phenyl) | H | OH | A | 2 | 1.28 | 537.1 | 537.0 |
| 55 | (ethyl-phenyl-1,2,3-triazole) | H | OH | A | 8 | 0.51 | 521.1 | 521.3 |

TABLE 1-continued
Analytical data for N[7]-alkylated GMP derivatives.
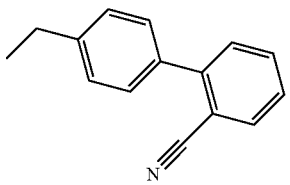 [SMILES: CCc1ccc(-c2ccccc2C#N)cc1]
| No. | —Y—R[1] | R[3] | R[4] | Synthetic method | LCMS method | $R_t$ min | Calc. mass $[M + H]^+$ | Exp. Mass $[M + H]^+$ |
|---|---|---|---|---|---|---|---|---|
| 56 | 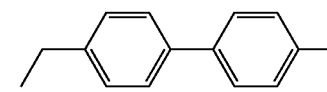 | H | OH | A | 6 | 1.42' | 555.1388 | 555.1341 |
| 57 | 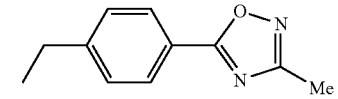 | H | OH | B | 6 | 1.38' | 572.1541 | 572.1576 |
| 58 | 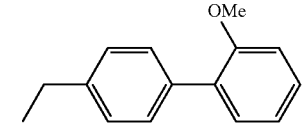 | H | OH | A | 2 | 1.00 | 536.1 | 536.0 |
| 59 | 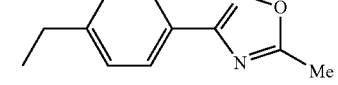 | H | OH | B | 6 | 1.73' | 560.1541 | 560.1559 |
| 60 | 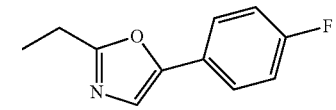 | H | OH | A | 2 | 1.31 | 536.1 | 536.1 |
| 61 | 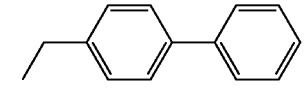 | H | OH | A | 2 | 1.28 | 537.1 | 537.0 |
| 62 | 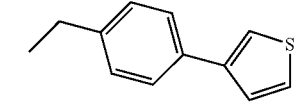 | H | H | B | 6 | 1.79' | 514.1486 | 514.1504 |
| 63 | 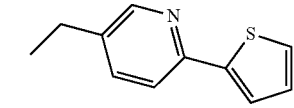 | H | OH | A | 8 | 0.69 | 536.1 | 536.3 |
| 64 |  | H | OH | A | 8 | 0.56 | 537.1 | 537.2 |

TABLE 1-continued
Analytical data for N⁷-alkylated GMP derivatives.
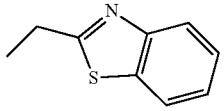
| No. | —Y—R¹ | R³ | R⁴ | Synthetic method | LCMS method | R$_t$ min | Calc. mass [M + H]⁺ | Exp. Mass [M + H]⁺ |
|---|---|---|---|---|---|---|---|---|
| 65 | 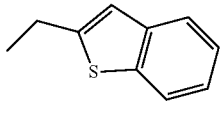 | H | OH | A | 2 | 1.30 | 511.1 | 511.2 |
| 66 | 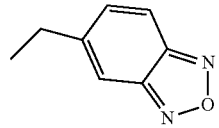 | H | OH | A | 2 | 1.22 | 510.1 | 510.0 |
| 67 | 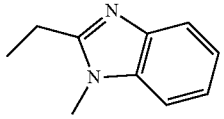 | H | OH | A | 6 | 0.66' | 496.0976 | 496.0986 |
| 68 | 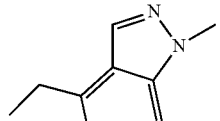 | H | OH | A | 2 | 1.00 | 508.1 | 508.1 |
| 69 | 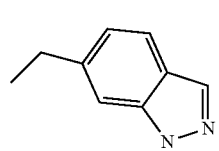 | H | OH | A | 6 | 0.74' | 508.1340 | 508.1321 |
| 70 | 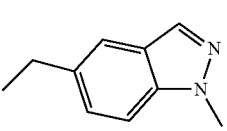 | H | OH | A | 6 | 0.70' | 508.1340 | 508.1352 |
| 71 | 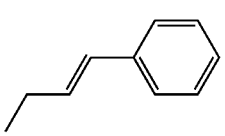 | H | OH | A | 6 | 0.63' | 508.1340 | 508.1350 |
| 72 | Me | H | OH | A | 2 | 0.27 | 378.1 | 378.1 |
| 73 |  | H | OH | B | 6 | 1.09' | 480.1279 | 480.1273 |

TABLE 1-continued

Analytical data for N[7]-alkylated GMP derivatives.

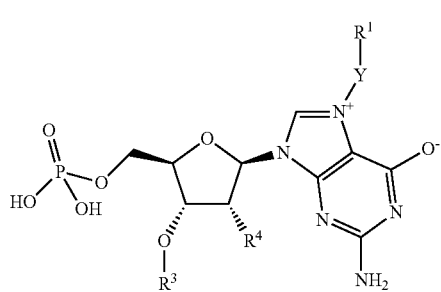

| No. | —Y—R[1] | R[3] | R[4] | Synthetic method | LCMS method | $R_t$ min | Calc. mass $[M + H]^+$ | Exp. Mass $[M + H]^+$ |
|---|---|---|---|---|---|---|---|---|
| 74 | 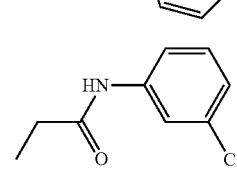 | H | OH | A | 2 | 1.34 | 512.1 | 512.1 |
| 75 | 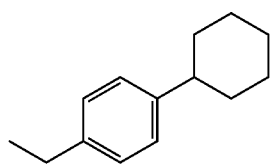 | H | OH | A | 2 | 1.48 | 531.1 | 531.0 |

Analytical data for N[7]-alkylated GDP derivatives are presented in Table 2. The following analogs were prepared similarly by general methods A or B or analogously to the methods described in Examples 1-17.

TABLE 2

Analytical data for N[7]-alkylated GDP derivatives

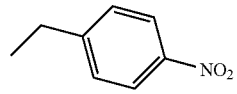

| No. | —Y—R[1] | R[3] | R[4] | Synthetic method | LC/MS method | $R_t$ Min | Calc. mass $[M + H]^+$ | Exp. Mass $[M + H]^+$ |
|---|---|---|---|---|---|---|---|---|
| 1 | Me | H | Me | A | 2 | 0.30' | 472.1 | 473.1 |
| 2 |  | H | H | B | 2 | 1.69 | 617.2 | 617.3 |
| 3 |  | H | H | B | 1 | 0.55 | 579.1 | 579.0 |

TABLE 2-continued
Analytical data for N[7]-alkylated GDP derivatives
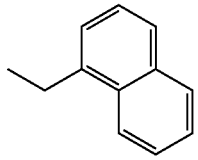
| No. | —Y—R[1] | R[3] | R[4] | Synthetic method | LC/MS method | R$_t$ Min | Calc. mass [M + H]+ | Exp. Mass [M + H]+ |
|---|---|---|---|---|---|---|---|---|
| 4 | 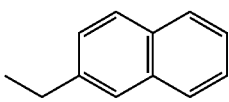 | H | H | B | 1 | 0.82 | 584.1 | 584.2 |
| 5 | 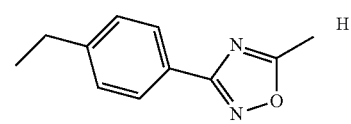 | H | H | B | 1 | 0.83 | 584.1 | 584.2 |
| 6 | 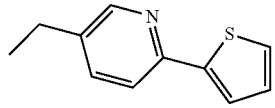 | H | H | A | 2 | 1.00 | 616.1 | 616.1 |
| 7 | 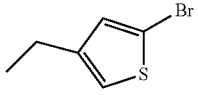 | H | H | A | 2 | 0.96 | 617.1 | 617.1 |
| 8 | 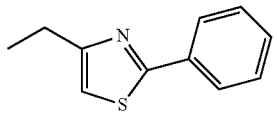 | H | H | A | 2 | 1.10 | 618.0 | 619.9 |
| 9 | 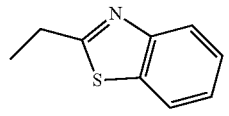 | H | H | A | 2 | 1.30 | 617.1 | 617.0 |
| 10 | 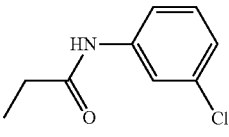 | H | H | A | 2 | 0.98 | 591.1 | 591.0 |
| 11 |  | H | H | A | 2 | 1.23 | 611.1 | 611.0 |

TABLE 2-continued

Analytical data for N[7]-alkylated GDP derivatives

| No. | —Y—R[1] | R[3] | R[4] | Synthetic method | LC/MS method | $R_t$ Min | Calc. mass $[M + H]^+$ | Exp. Mass $[M + H]^+$ |
|---|---|---|---|---|---|---|---|---|
| 12 | (benzyl propanoate group) | H | H | A | 2 | 1.06 | 592.1 | 592.1 |
| 13 | (4-(thiophen-2-yl)phenethyl group) | H | H | A | 2 | 1.45 | 616.1 | 616.1 |
| 14 | (4-chlorocinnamyl-type group) | H | H | A | 1 | 0.91' | 594.8 | 594.0 |

Analytical data for N[7]-alkylated ionosine derivatives are presented in Table 3. The following analogs were prepared similarly by general methods A or B or analogously to the methods described in Examples 1-17.

TABLE 3

Analytical data for N[7]-alkylated inosine derivatives.

| No. | n | Synthetic method | LC/MS method | $R_t$ | Calc. mass $[M + H]^+$ | Exp. Mass $[M + H]^+$ |
|---|---|---|---|---|---|---|
| 1 | 1 | B | 2 | 1.38 | 515.1 | 515.2 |
| 2 | 2 | B | 2 | 1.47 | 595.1 | 595.1 |

101

Procedures for Synthesis of C8 Substituted Xanthines

Example 18. 7-([1,1'-biphenyl]-4-ylmethyl)-8-bromo-3-methyl-1H-purine-2,6(3H,7H)-dione

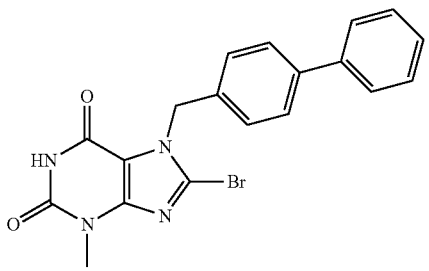 [SMILES: Cn1c(=O)[nH]c(=O)c2c1nc(Br)n2Cc1ccc(-c2ccccc2)cc1]

A mixture of 8-bromo-3-methyl-1H-purine-2,6(3H,7H)-dione (245 mg, 1.000 mmol), 4-(bromomethyl)-1,1'-biphenyl (247 mg, 1.000 mmol), and $K_2CO_3$ (38.5 mg, 1.000 mmol) in DMF (5 mL) was stirred at RT overnight. Water was added to the reaction mixture. The resultant solid was collected by filtration, washed with water, and dried. ISCO purification (Silica 80 g, 0-5% MeOH in DCM) gave the titled product.

Example 19: (4-(7-([1,1'-biphenyl]-4-ylmethyl)-3-methyl-2,6-dioxo-2,3,6,7-tetrahydro-1H-purin-8-yl)phenyl)phosphonic acid

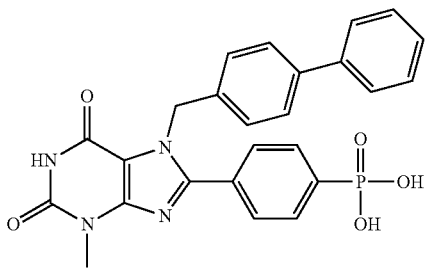 [SMILES: Cn1c(=O)[nH]c(=O)c2c1nc(-c1ccc(P(=O)(O)O)cc1)n2Cc1ccc(-c2ccccc2)cc1]

A reaction mixture of Example 18 (60 mg, 0.146 mmol), dimethyl (4-(4,4,5,5-tetramethyl-1,3,2-dioxaborolan-2-yl)phenyl)phosphonate (45.5 mg, 0.146 mmol), $Na_2CO_3$ (30.9 mg, 0.292 mmol), tetrakis(triphenylphosphine)palladium (16.9 mg, 0.015 mmol), and water (0.2 mL) in dioxane (1 mL) was purged with N2 for 2 minutes, then stirred at 100° C. in a sealed vial overnight. Prep-HPLC purification (Waters X-Bridge C18 30×50 mm 5 μm column, ACN/$H_2O$ w/5 mM $NH_4OH$ @75 ml/min, 15-40% ACN over 3.5 min gradient) isolated mono-methyl ester and dimethyl ester. The fractions containing these two products were combined and concentrated under vacuum. The residue was dissolved in DMF (1 mL), bromotrimethylsilane (112 mg, 0.729 mmol) was added. The reaction mixture was stirred at RT overnight. Water and MeOH was added to quench the reaction, and the resultant solution was concentrated under vacuum. Prep-HPLC purification (Waters X-Bridge 30×50 mm 5 um column ACN/$H_2O$ w/5 mM $NH_4OH$ @75 ml/min, 5-20% ACN over 3.2 min gradient) gave the desired product. $^1H$ NMR (400 MHz, DMSO-d6): δ ppm 7.64-7.77 (2H, m), 7.54-7.64 (6H, m), 7.27-7.46 (3H, m), 7.03-7.15 (2H, m), 5.56-5.71 (2H, m), 3.42 (3H, s). LCMS (XBridge C18 3.5 μm 3.0×30 mm ACN/$H_2O$ w/5 mM $NH_4OH$ @75 ml/min, 5-95 over 2 min gradient) $R_t$=0.51 min, MS $[M+H]^+$ Observed: 489.3, calculated: 489.4.

Example 20: 7-([1,1'-biphenyl]-4-ylmethyl)-8-bromo-1,3-dimethyl-1H-purine-2,6(3H,7H)-dione

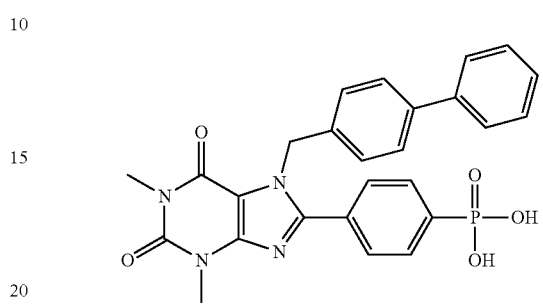

The titled product was prepared analogously according to the method described above. $^1H$ NMR (400 MHz, methanol-d4): δ ppm 7.88-8.00 (2H, m), 7.68-7.78 (2H, m), 7.49-7.59 (4H, m), 7.27-7.44 (3H, m), 7.03-7.15 (2H, m), 5.72-5.81 (2H, m), 3.63 (3H, s), 3.38 (3H, s). LCMS (XBridge C18 3.5 μm 3.0×30 mm ACN/$H_2O$ w/5 mM $NH_4OH$ @75 ml/min, 5-95 over 2 min gradient) $R_t$: 0.63 min, MS $[M+H]^+$ observed: 503.3, calculated: 503.4.

General synthesis of C8 substituted purines:

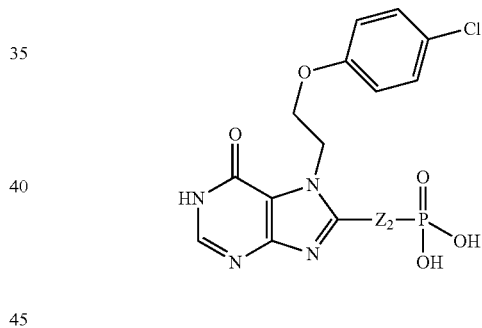

Step 1: 6-amino-5-((2-(4-chlorophenoxy)ethyl)amino)pyrimidin-4(3H)-one

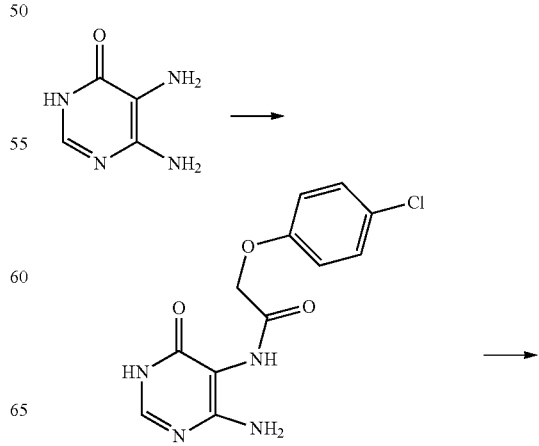

103
-continued

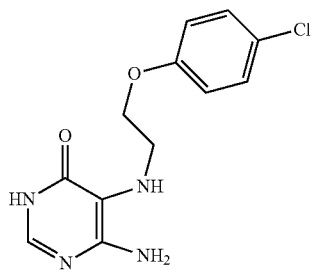

2-(4-chlorophenoxy)acetic acid (13.3 g, 71.4 mmol) was dissolved in DMF (90 mL, 0.8 M), and triethylamine (14.4 g, 143 mmol, 2 equiv.) and HATU (27.1 g, 71.4 mmol) was added. The reaction was stirred at room temperature for 30 min before the pyridone (9.0 g, 71.4 mmol) was added. After stirring the mixture at room temperature over night, the reaction was quenched with water, and the pH was adjusted to 1 by addition of 5 N HCl. The white precipitate was collected, washed with 1 N HCl, and dried under vacuum for 2 days (12.7 g, 43.1 mmol, 60%). The amide obtained was used as such in the next step.

The amide obtained above (10 g, 33.9 mmol) was dissolved in THF (250 mL) and cooled to 0° C. LiAlH$_4$ (7.73 g, 204 mmol) was slowly added, and the mixture was stirred at room temperature for 30 min and 50° C. for 5 hours. The mixture was then cooled to 0° C. and quenched by addition of IN HCl. The white precipitate was collected, washed with 1 N HCl, and dried under vacuum for 2 days. The product was obtained as white solid and was used without further purification (3.0 g, 10.7 mmol, 32%).

Step 2: General Procedure for Acylation and Ring Closure

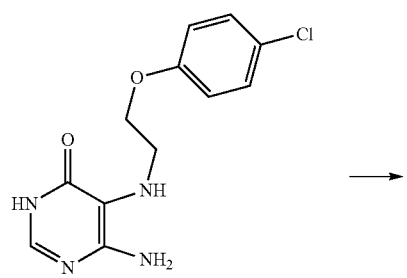

104
-continued

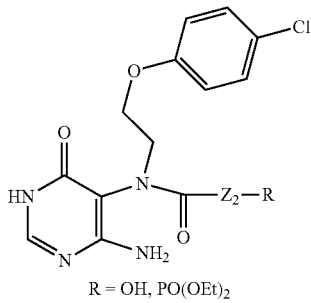
R = OH, PO(OEt)$_2$

The carboxylic acid was taken up in DMF (0.1 M) and treated with HATU (2 equiv.) and triethylamine (4.5 equiv.). The solution was stirred at room temperature for 15 min before the pyrimidine obtained in step 1 was added. The resulting solution was stirred for 16 h at room temperature and then diluted with EtOAc and washed with a buffered solution (pH=7.0). The aqueous layers were extracted 2× with EtOAc, and the combined organic layers were dried over Na$_2$SO$_4$. Concentration of the solution under vacuum gave a brown oil, which was purified by RP-HPLC.

For R=OH: The amide obtained above was taken up in isopropanol (0.1 M), sodium tert-butoxide was added (5 equiv.), and the mixture was stirred at 80° C. for 4 h. Acetic acid was added until the solution was acidic and a precipitate was formed. The precipitate was filtered, washed with water, and dried in vacuum. The resulting alcohol was phosphorylated by treatment with POCl$_3$ in trimethylphosphate for 2 h at 0° C. The reaction was quenched with TEAB (1M) and directly subjected to purification by RP-HPLC.

For R=PO(OEt)$_2$: The phosphate esters obtained above were hydrolyzed by treatment of a 0.7 M solution in DMF with TMSBr (5.5 eq.). After stirring for 16 h at room temperature, the reaction was quenched by addition of MeOH/H$_2$O 1/1 and 1 M TEAB. The suspension was filtered and directly subjected to purification by RP-HPLC.

Analytical data for C8-substituted purines are presented in Table 4. The following analogs were prepared by methods described above.

TABLE 4

Analytical data for C8 substituted purines.

| No. | $Z_2$ | LC/MS method | $R_t$ | Calc. mass $[M + H]^+$ | Exp. Mass $[M + H]^+$ |
|---|---|---|---|---|---|
| 3 | (phenyl-phenyl) | 1 | 0.95' | 447.8 | 447.1 |
| 4 | (phenyl-P(O)(OH)-O) | 2 | 1.44' | 525.8 (M − H⁺) | 525.3 (M − H⁺) |
| 5 | (phenyl-O) | 1 | 1.59' | 463.8 | 463.3 |
| 6 | (propylene) | 1 | 0.91' | 413.8 | 413.1 |
| 7 | (trans-cyclohexyl-O) | 10 | 1.64' | 469.8 | 469.3 |
| 8 | (cyclopropyl-CH2-O) | 3 | 0.14' | 441.8 | 441.2 |

Preparation of Imidazole Activated mRNA Caps

General Procedure for Imidazole Activation for GMP and GDP Derivatives:

To a solution of the triethylammonium salt of the $N^7$-alkylated-GMP/GDP derivative in DMF was added imidazole (10 eq.), 2,2'-dipyridyl disulfide (4 eq.) and TEA (2 eq.). The reaction stirred at RT for 5 min and then triphenylphosphine (4 eq.) was added turning the reaction yellow in color. After stirring at RT for 16-18 h, 1M NaClO₄ in acetone (10 eq.) was added to the reaction generating a white precipitate. Additional acetone was added to the reaction, and the resulting suspension was cooled at 4° C. for 20 min and centrifuged. The supernatant was decanted and the precipitate washed with acetone, cooled at 4° C. for 10 min, and centrifuged. This wash procedure was repeated one or two more times. The resulting precipitate was dried under vacuum to give the sodium salt of the imidazole activated $N^7$-alkylated GMP/GDP derivative.

Example 21: $P^2$-imidazolide $N^7$-([1,1'-biphenyl]-4-ylmethyl)-5'-GDP Na salt

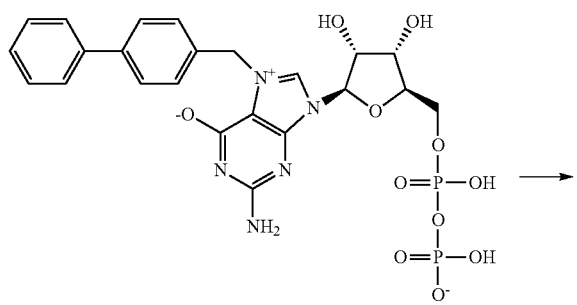

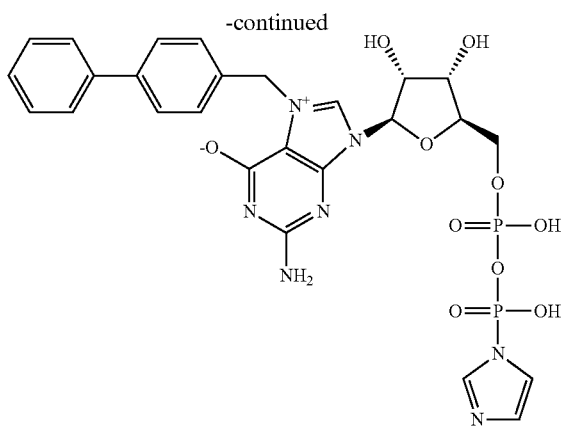

A mixture of triethylammonium salt of $N^7$-([1,1'-biphenyl]-4-ylmethyl)-5' GDP (45 mg, 0.049 mmol), imidazole (50 mg, 0.742 mmol), 2,2'-dithiodipyridine (65 mg, 0.297 mmol), triethylamine (207 μL, 1.484 mmol), and triphenylphosphine (78 mg, 0.297 mmol) in dimethylformamide (1.0 mL) was stirred at room temperature for 3 h. A solution of sodium perchlorate in acetone (1M, 1 mL) was added and then diluted with acetone (40 mL). The precipitate was separated by centrifugation, washed with acetone three times and dried under vacuum to afford the title compound as sodium salt (34 mg, 93%). $^1$H NMR (400 MHz, D$_2$O) δ ppm: 7.80-7.90 (1H, s), 7.63-7.72 (4H, m), 7.38-7.56 (5H, m), 7.18-7.27 (1H, s), 6.86-6.95 (1H, s), 5.97-6.07 (1H, m), 5.59-5.75 (2H, m), 4.58-4.64 (2H, m), 4.33-4.40 (3H, m), 4.16-4.29 (1H, m), 4.06-4.16 (1H, m). $^{13}$C NMR (162 MHz, D$_2$O): δ ppm: 11.712 (1P), 19.863 (1P). LCMS method 2 $R_t$: 1.35 min, MS [M–H]$^+$ observed: 659.1, calculated: 659.1.

Example 22: P$^2$-imidazolide $N^7$-([1,1'-biphenyl]-4-ylmethyl)-5'-GMP Na salt

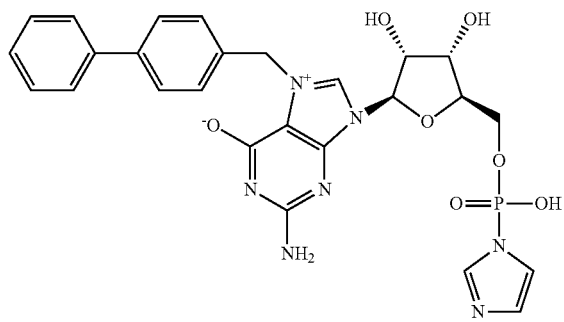

The title compound was synthesized analogously to the method described in Example 21. $^1$H NMR (400 MHz, D$_2$O) δ ppm: 7.78-7.83 (1H, s), 7.43-7.49 (4H, m), 7.16-7.40 (5H, m), 7.01-7.08 (1H, s), 6.83-6.90 (1H, s), 5.79-5.87 (1H, m), 5.51-5.76 (2H, m), 4.50-4.57 (1H, m), 4.20-4.35 (2H, m), 4.00-4.16 (2H, m). $^{31}$P NMR (162 MHz, D$_2$O): δ ppm: 8.134 (1P). LCMS method 2 $R_t$: 1.32 min, MS [M–H]$^+$ observed: 577.9, calculated: 578.2.

Example 23: 7-([1,1'-biphenyl]-4-ylmethyl)-2-amino-9-((2-((hydroxy((hydroxy(1H-imidazol-1-yl)phosphoryl)oxy)phosphoryl)oxy)ethoxy)methyl)-9H-purin-7-ium-6-olate

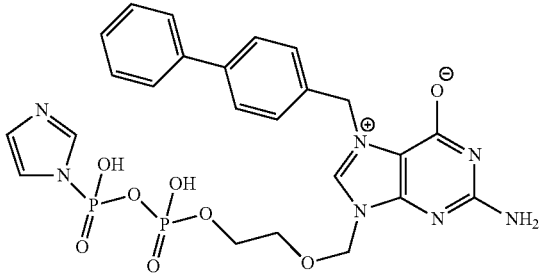 [SMILES: Nc1nc([O-])c2c(n1)n(COCCOP(=O)(O)OP(=O)(O)n1ccnc1)c[n+]2Cc1ccc(-c2ccccc2)cc1]

The title compound was synthesized following the general procedure for imidazole activation of bisphosphates described above. LCMS method 5 MS [M–H]$^+$ observed: 602.3, calculated: 602.1.

Example 24: P$^2$-imidazolide-$N^7$-(2-(4-chlorophenoxy)ethyl)-2'-O-methyl-5'-GDP Na salt

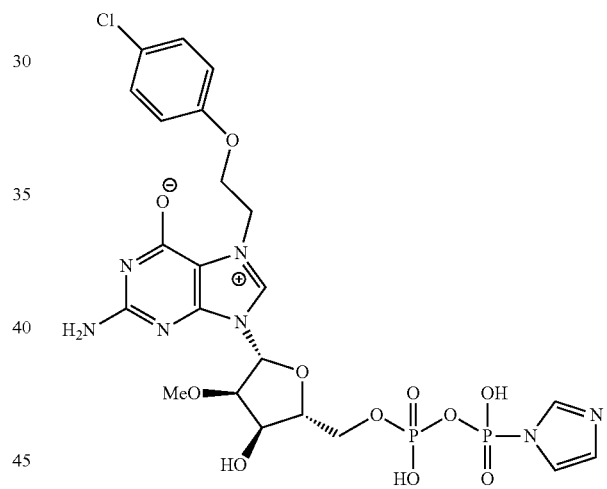

Step 1: $N^7$-(2-(4-chlorophenoxy)ethyl)-2'-O-methyl-guanosine

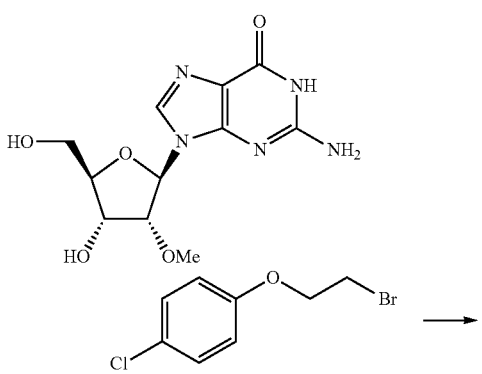

-continued

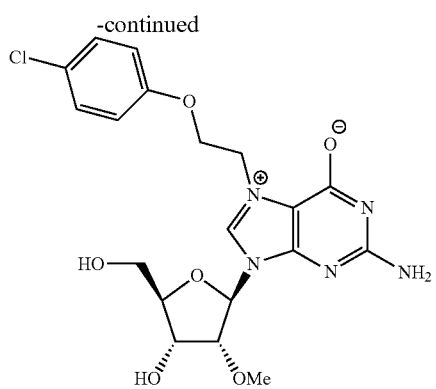

2'OMe-Guanosine (0.673 mmol) and 1-(2-bromoethoxy)-4-chlorobenzene (2.70 mmol) were taken up in 4 ml anh. DMSO and stirred at 50° C. for 20 h. The reaction was cooled to RT, diluted with DMSO, and purified on prepatory HPLC [Shimadzu Prep HPLC (Sunfire Prep C18 5 μm, 100 mm×30 mm column; 0-20 min: 5 to 30% 0.1% TFA in ACN/0.1% TFA in H₂O; 42 mL/min)]. Product fractions were pooled and concentrated while azeotroping with toluene to afford the trifluoroacetate salt of the title compound as a white solid (99 mg, 0.17 mmol, 26%). LCMS method 2 R$_t$=1.38 mins; MS m/z [M+H]⁺ 452.2.

Step 2: N⁷-(2-(4-chlorophenoxy)ethyl)-2'-O-methyl-5'-GMP TEA salt

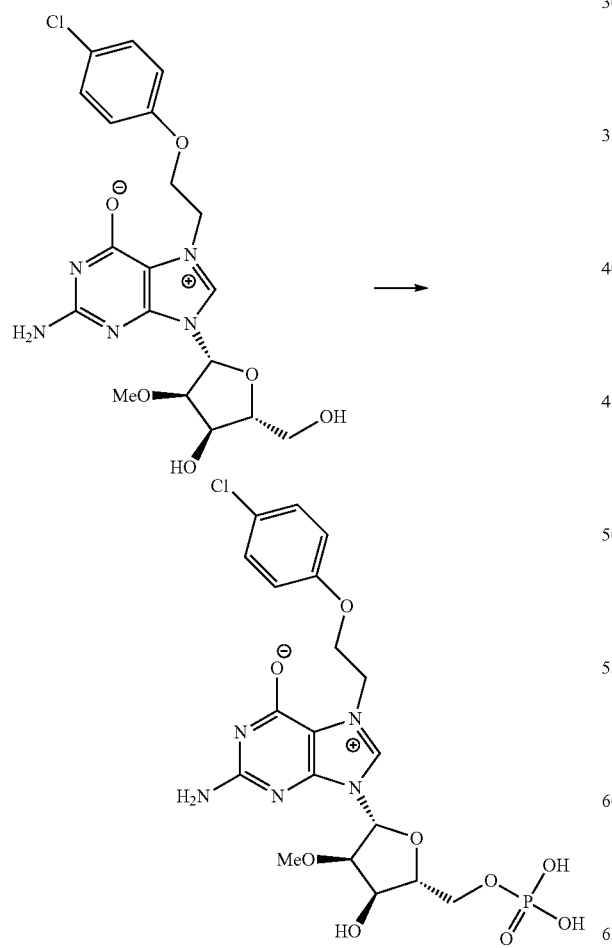

To a solution of N⁷-(2-(4-chlorophenoxy)ethyl)-2'-O-methyl-guanosine (0.085 mmol) in 1.0 ml trimethyl phosphate cooled to 0° C. was slowly added POCl3 (0.536 mmol) dropwise. The reaction stirred at 0° C. for 6.5 h and was then cooled to −20° C. for 16 h. The reaction was then warmed to 0° C. for 2 h. Additional POCl₃ (0.536 mmol) was added to the reaction and the reaction stirred at 0° C. for 3 h. The reaction was slowly quenched at 0° C. with 1M TEAB (aq.) (3.5 ml). Upon completion of the TEAB addition, the reaction was warmed to RT to ensure quenching of excess POCl₃. The quenched reaction was purified directly on prepatory ion exchange chromatography [(Tosoh TSKgel DEAE-5PW, 13 μm, 21.5×150 mm, 0-30 min: 0-100% 1M TEAB, 5 ml/min)]. Lyophilization of product fractions yielded the triethylammonium salt of the title compound as a white solid, which was used directly in the next step. LCMS method 2 R$_t$=1.34 mins; MS m/z [M+H]+ 532.9; ¹H NMR (D₂O) δ: 7.16-7.22 (m, 2H), 6.80-6.86 (m, 2H), 6.03 (d, J=3.4 Hz, 1H), 4.78-4.84 (m, 2H), 4.48-4.54 (m, 2H), 4.46 (t, J=5.3 Hz, 1H), 4.25-4.30 (m, 1H), 4.18-4.22 (m, 1H), 4.09-4.17 (m, 1H), 3.96-4.03 (m, 1H), 3.51 (s, 3H), 3.14 (q, J=7.4 Hz, NEt₃), 1.21 (t, J=7.3 Hz, NEt₃).

Step 3: P¹-imidazolide N⁷-(2-(4-chlorophenoxy)ethyl)-2'-O-methyl-5'-GMP Na salt

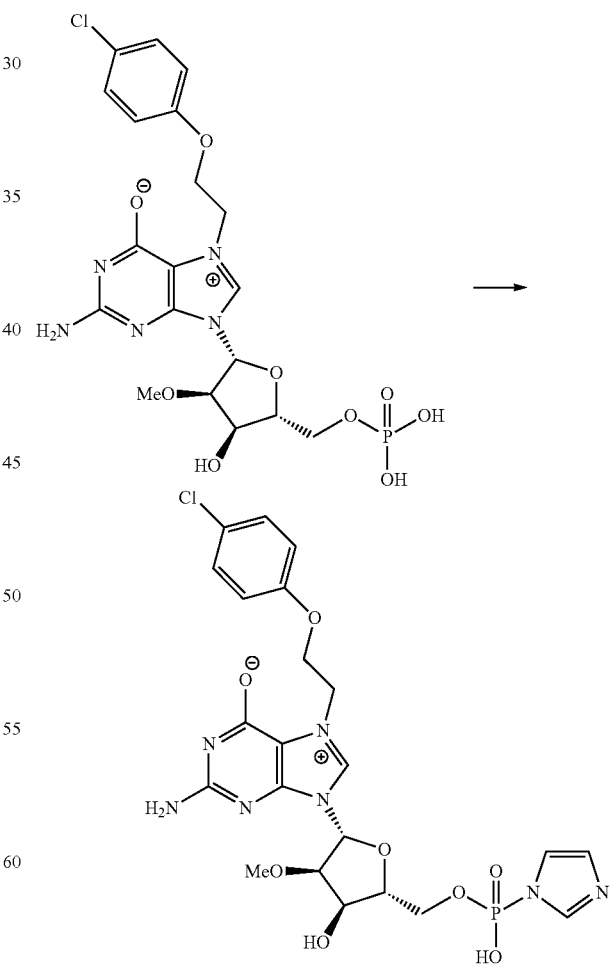

To a suspension of N⁷-(2-(4-chlorophenoxy)ethyl)-2'-O-methyl-5'-GMP (0.05 mmol) in 1.0 ml anhydrous DMF was added imidazole (0.514 mmol), 2,2'-dipyridyl disulfide (0.227 mol) and TEA (0.072 mmol). PPh₃ (0.229 mmol) was then added to the reaction turning it yellow in color. After stirring at RT for 18 h, 1M NaClO₄ in acetone (0.250 mmol) was added to the reaction followed by 4 ml of acetone. The resulting suspension was cooled at 4° C. for 20 min and centrifuged. The supernatant was decanted and the resulting precipitate was washed with 5 ml of acetone, cooled at 4° C. for 20 min and centrifuged again. This wash procedure was repeated two more times. The resulting off-white solid was dried under vacuum to afford the sodium salt of the title compound (30 mg). This compound was used directly in Step 4. LCMS method 5 MS(ES):m/z=580.4 (M−H+).

Step 4: N⁷-(2-(4-chlorophenoxy)ethyl)-2'-O-methyl-5'-GDP TEA salt

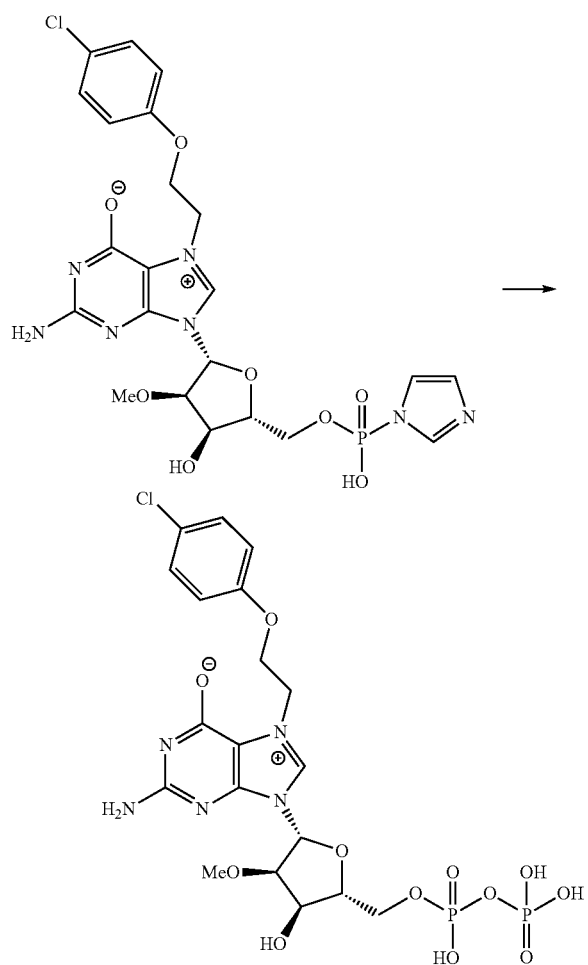

To a solution of P¹-imidazolide N⁷-(2-(4-chlorophenoxy)ethyl)-2'-O-methyl-5'-GMP Na salt (0.05 mmol) in 1 ml anh. DMF was added tributylammonium orthophosphate (prepared as described in: A. R. Kore, G. Parmar, Syn. Comm. 2006, 36, 3393-3399; 1 M in DMF, 0.250 mmol) dropwise followed by ZnCl₂ (0.051 mmol). The reaction stirred at RT for 4.5 h and was then quenched with water (1 ml) and concentrated to an oily solid. This solid was taken up in DMF (1 ml) and 1 M NaClO₄ in acetone (0.500 mmol) was added followed by 7 ml of acetone. The resulting suspension was cooled to 0° C. for ~10 min, centrifuged, and the supernatant decanted. The solid was washed once with acetone, centrifuged, and the supernatant decanted. The resulting solid was then dried under vacuum to remove any residual organics and taken up in H₂O and purified using prepatory ion exchange chromatography [(Tosoh TSKgel DEAD-5PW, 13 μm, 21.5×150 mm, 0-100% 1M TEAB, 5 ml/min)]. Product fractions were pooled, concentrated, and azeotroped with ethanol to afford the triethylammonium salt of the title compound as a white solid (5.7 mg, 6.6 tmol, 13%). LCMS method 5 MS(ES+):m/z=612.0 (M+H+); ¹H NMR (D₂O) δ: 9.25 (s, 1H), 7.13 (d, J=8.9 Hz, 2H), 6.79 (d, J=8.9 Hz, 2H), 5.99 (d, J=3.1 Hz, 1H), 4.76-4.87 (m, 2H), 4.40-4.54 (m, 3H), 4.24-4.35 (m, 2H), 4.13-4.23 (m, 2H), 3.50 (s, 3H), 3.13 (q, J=7.3 Hz, NEt₃), 1.17-1.23 (m, J=7.3, 7.3 Hz, NEt₃).

Step 5: P²-imidazolide-N⁷-(2-(4-chlorophenoxy)ethyl)-2'-O-methyl-5'-GDP Na salt

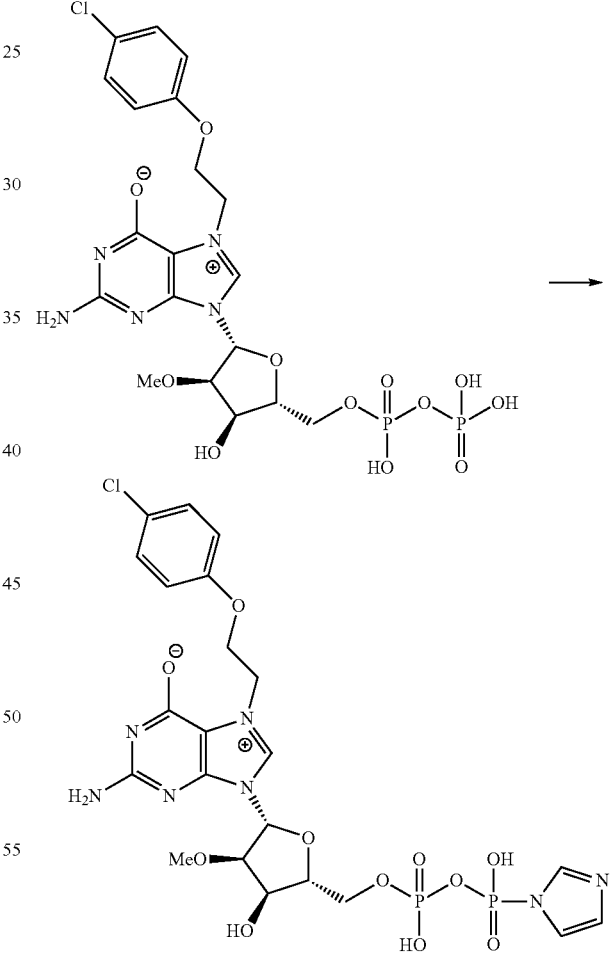

To a suspension of N⁷(2-(4-chlorophenoxy)ethyl)-2'-O-methyl-5'-GDP TEA salt (6.55 μmol) in 0.5 ml anh. DMF was added imidazole (88 μmol), 2,2'-dipyridyl disulfide (27.2 μmol) and TEA (14.31 μmol). PPh₃ (26.7 μmol) was then added to the reaction turning it yellow in color. After stirring at RT for 18 h, 1 M NaClO₄ in acetone (0.100 mmol) was added to the reaction followed by acetone (2 ml)

generating a white precipitate. This suspension was cooled at 4° C. for 20 min and centrifuged. The supernatant was decanted and the resulting precipitate was washed with acetone (3 ml), cooled at 4° C. for 10 min and centrifuged. This acetone wash procedure was repeated one more time. The resulting white solid was dried under vacuum to give the sodium salt of the title compound (4.6 mg, 6.4 μmol, 97%). This compound was used directly in the mRNA capping reaction. LCMS method 5 MS(ES):m/z=660.2 (M–H+).

Example 25: P²-imidazolide-N⁷-(2-(4-chlorophenoxy)ethyl)-3'-O-methyl-5'-GDP Na salt

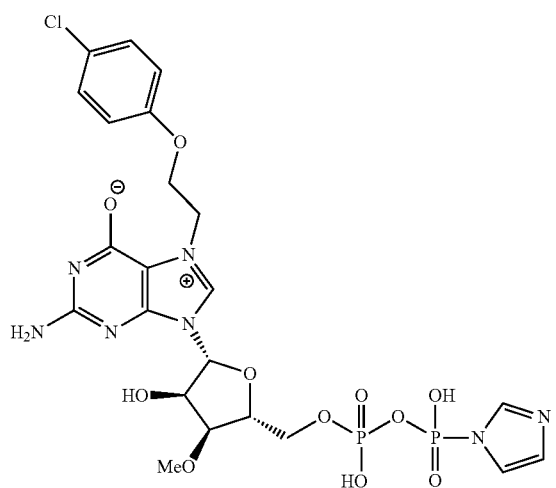 [SMILES: CO[C@H]1[C@@H](O)[C@H](n2c[n+](CCOc3ccc(Cl)cc3)c3c([O-])nc(N)nc32)O[C@@H]1COP(=O)(O)OP(=O)(O)n1ccnc1]

Step 1: N⁷-(2-(4-chlorophenoxy)ethyl)-3'-O-methyl-5'-guanosine

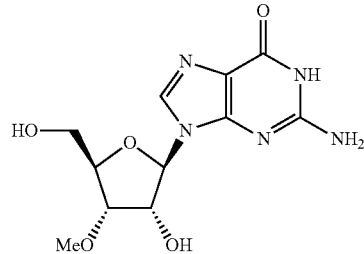

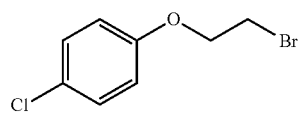

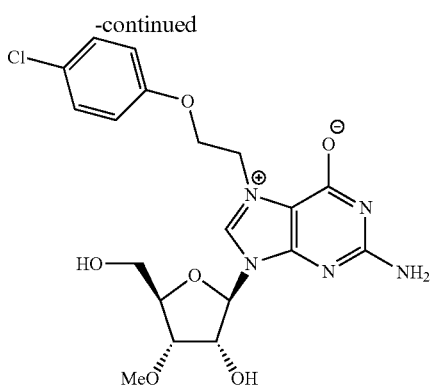

3'OMe-Guanosine (0.673 mmol) and 1-(2-bromoethoxy)-4-chlorobenzene (2.70 mmol) were taken up in 4 ml anh. DMSO and stirred at 50° C. for 2 0 h. The reaction was cooled to RT, diluted with DMSO, and purified on prepatory HPLC [Shimadzu Prep HPLC (Sunfire Prep C18 5m, 100 mm×30 mm column; 0-20 min: 5 to 30% 0.1% TFA in ACN/0.1% TFA in H₂O; 42 mL/min)]. Product fractions were pooled and concentrated while azeotroping with toluene to afford the triflouroacetate salt of the title compound as a white solid (124 mg, 0.223 mmol, 33%). LCMS method 2 $R_f$=1.39 mins; MS m/z [M+H]⁺ 452.9.

Step 2: N⁷-(2-(4-chlorophenoxy)ethyl)-3'-O-methyl-5'-GMP TEA salt

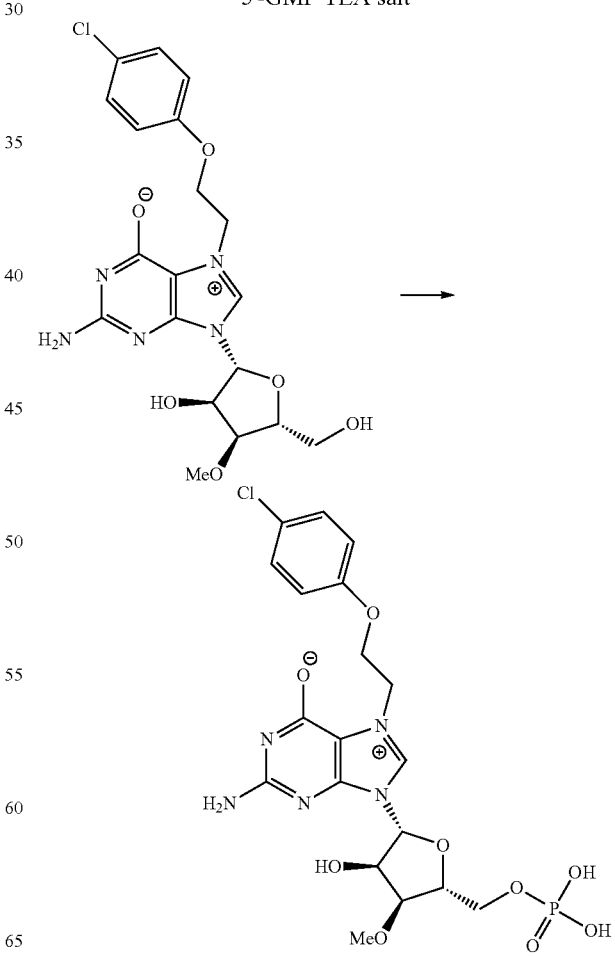

To a solution of N⁷-(2-(4-chlorophenoxy)ethyl)-3'-O-methyl-5'-guanosine (0.115 mmol) in 1.0 ml trimethyl phosphate cooled to 0° C. was slowly added POCl₃ (0.536 mmol) dropwise. The reaction stirred at 0° C. for 6.5 h and was then cooled to −20° C. for 16 h (placed in the freezer overnight). The reaction was then warmed to 0° C. for 2 h. Additional POCl₃ (0.536 mmol) was added to the reaction and the reactions stirred at 0° C. for 3 h. The reaction was slowly quenched at 0° C. with 1M TEAB(aq.) (3.5 ml). Upon completion of the TEAB addition, the reaction was warmed to RT to ensure quenching of excess POCl₃. The quenched reaction was purified directly on prepatory ion exchange chromatography [(Tosoh TSKgel DEAE-5PW, 13 μm, 21.5× 150 mm, 0-30 min: 0-100% 1M TEAB, 5 ml/min)]. Lyophilization of product fractions yielded the triethylammonium salt of the title compound as a white solid, which was used as obtained in the next step. LCMS method 2 $R_t$=1.34 mins; MS m/z [M+H]+ 532.8; ¹H NMR (D₂O) δ: 7.16-7.23 (m, 2H), 6.79-6.87 (m, 2H), 5.94 (d, J=4.0 Hz, 1H), 4.78-4.86 (m, 2H), 4.47-4.52 (m, J=5.0, 5.0 Hz, 2H), 4.36-4.43 (m, 1H), 4.09-4.17 (m, 1H), 4.07 (t, J=5.0 Hz, 1H), 3.93-4.01 (m, 1H), 3.43 (s, 3H), 3.13 (q, J=7.4 Hz, NEt₃), 1.21 (t, J=7.3 Hz, NEt₃).

Step 3: P¹-imidazolide-N⁷-(2-(4-chlorophenoxy)ethyl)-3'-O-methyl-5'-GMP Na salt

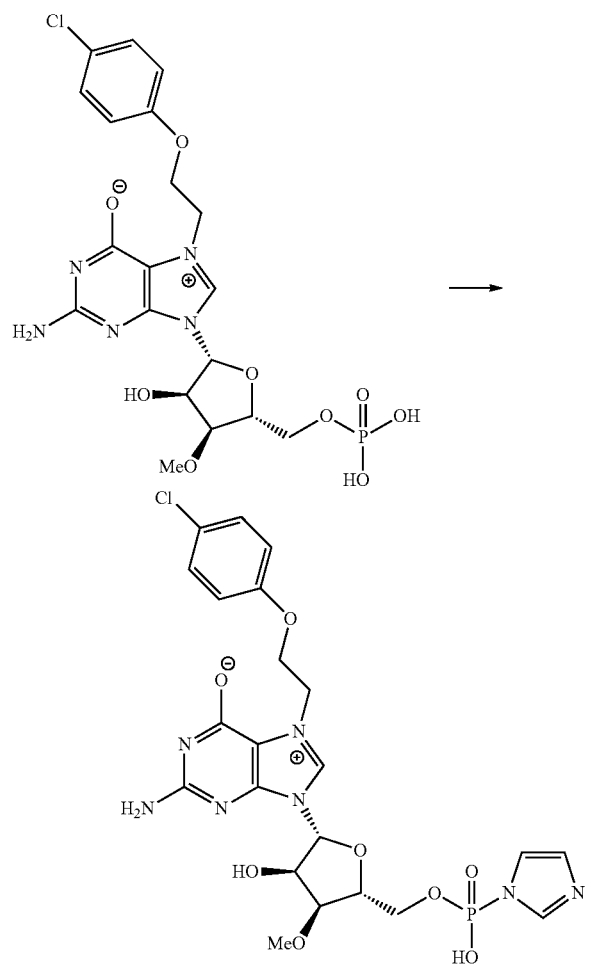

To a suspension of N⁷-(2-(4-chlorophenoxy)ethyl)-3'-O-methyl-5'-GMP TEA salt (0.075 mmol) in 1.0 ml anh. DMF was added imidazole (0.734 mol), 2,2'-dipyridyl disulfide (0.340 mmol) and TEA (0.108 mmol). PPh₃ (0.343 mmol) was then added to the reaction turning it yellow in color. After stirring at RT for 18 h, 1M NaClO₄ in acetone (0.375 mmol) was added followed by 4 ml of acetone. The resulting suspension was cooled at 4° C. for 20 min and centrifuged. The supernatant was decanted and the resulting precipitate was washed with acetone (5 ml), cooled at 4° C. for 20 min, and centrifuged. This wash procedure was repeated two more times. The resulting off-white solid was dried under vacuum to give the sodium salt of the title compound (45 mg). This compound was used directly in Step 4. LCMS method 5 MS(ES⁻):m/z=580.4 (M−H+).

Step 4: N⁷-(2-(4-chlorophenoxy)ethyl)-3'-O-methyl-5'-GDP TEA salt

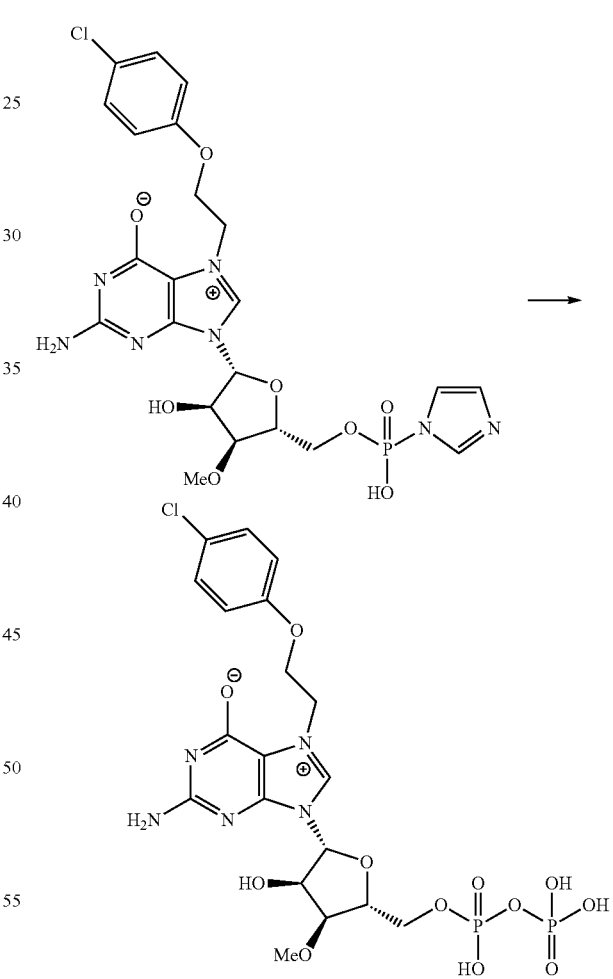

To a solution of P¹-imidazolide-N⁷-(2-(4-chlorophenoxy)ethyl)-3'-O-methyl-5'-GMP Na salt (0.075 mmol) in 1 ml anh. DMF was added tributylammonium orthophosphate (prepared as described in: A. R. Kore, G. Parmar, *Syn. Comm.* 2006, 36, 3393-3399; 1 M in DMF, 0.375 mmol) dropwise followed by ZnCl₂ (0.076 mmol). The rxn stirred at RT for 4.5 h and was then quenched with water (1 ml) and concentrated to an oily solid. This solid was taken up in DMF (1 ml) and 1M NaClO₄ in acetone (1.00 mmol) was added followed by acetone (7 ml). The resulting suspension was cooled to 0° C. for 10 min, centrifuged, and the supernatant decanted. The solid was washed once with acetone, centrifuged, and the supernatant decanted. The resulting solid was then dried under vacuum to remove any residual organics and purified using prepatory ion exchange chromatography [(Tosoh TSKgel DEAD-5PW, 13 μm, 21.5×150 mm, 0-100% 1M TEAB, 5 ml/min)]. Product fractions were pooled, concentrated, and azeotroped with ethanol to afford the triethylammonium salt of the title compound as a white solid (14.3 mg, 4.21 μmol, 8%). LCMS method 5 MS(ES−):m/z=610.2 (M−H+); ¹H NMR (D₂O) δ: 9.30 (s, 1H), 7.15 (d, J=9.0 Hz, 2H), 6.80 (d, J=9.0 Hz, 2H), 5.92 (d, J=4.0 Hz, 1H), 4.77-4.87 (m, 2H), 4.71-4.75 (m, 1H), 4.39-4.49 (m, 3H), 4.23-4.32 (m, 1H), 4.06-4.17 (m, 2H), 3.43 (s, 3H), 3.13 (q, J=7.4 Hz, NEt₃), 1.21 (t, J=7.3 Hz, NEt₃).

Step 5: P²-imidazolide-N⁷-(2-(4-chlorophenoxy) ethyl)-3'-O-methyl-5'-GDP Na salt To a suspension of 2-amino-7-(2-(4-chlorophenoxy) ethyl)-9-((2R,3R,4S,5R)-3-hydroxy-5-(((hydroxy(phosphonooxy)phosphoryl)oxy)methyl)-4-methoxytetrahydrofuran-2-yl)-6-oxo-6,9-dihydro-1H-purin-7-ium (4.20 μmol) in 0.5 ml anhydrous DMF was added imidazole (88 mol), 2,2'-dipyridyl disulfide (27.2 μmol) and TEA (14.3 μmol). PPh₃ (26.71 μmol) was then added to the reaction turning it yellow in color. After stirring at RT for 18 h, 1M NaClO₄ in acetone (0.100 mmol) was added to the reaction followed by acetone (2 ml) generating a white precipitate. This suspension was cooled at 4° C. for 20 min and centrifuged. The supernatant was decanted and the resulting precipitate was washed with acetone (3 ml), cooled at 4° C. for 10 min. and centrifuged. This acetone wash procedure was repeated one more time. The resulting white solid was dried under vacuum to give the sodium salt of the title compound (7.2 mg). This compound was used directly in the mRNA capping reaction. LCMS method 5 MS(ES):m/z=660.2 (M−H+).

Example 26: 7-([1,1'-biphenyl]-4-ylmethyl)-2-amino-9-((2R,3R,4S,5R)-3,4-dihydroxy-5-(((hydroxy((hydroxy(1H-imidazol-1-yl)phosphoryl) methyl)phosphoryl)oxy)methyl)tetrahydrofuran-2-yl)-6-oxo-6,9-dihydro-1H-purin-7-ium

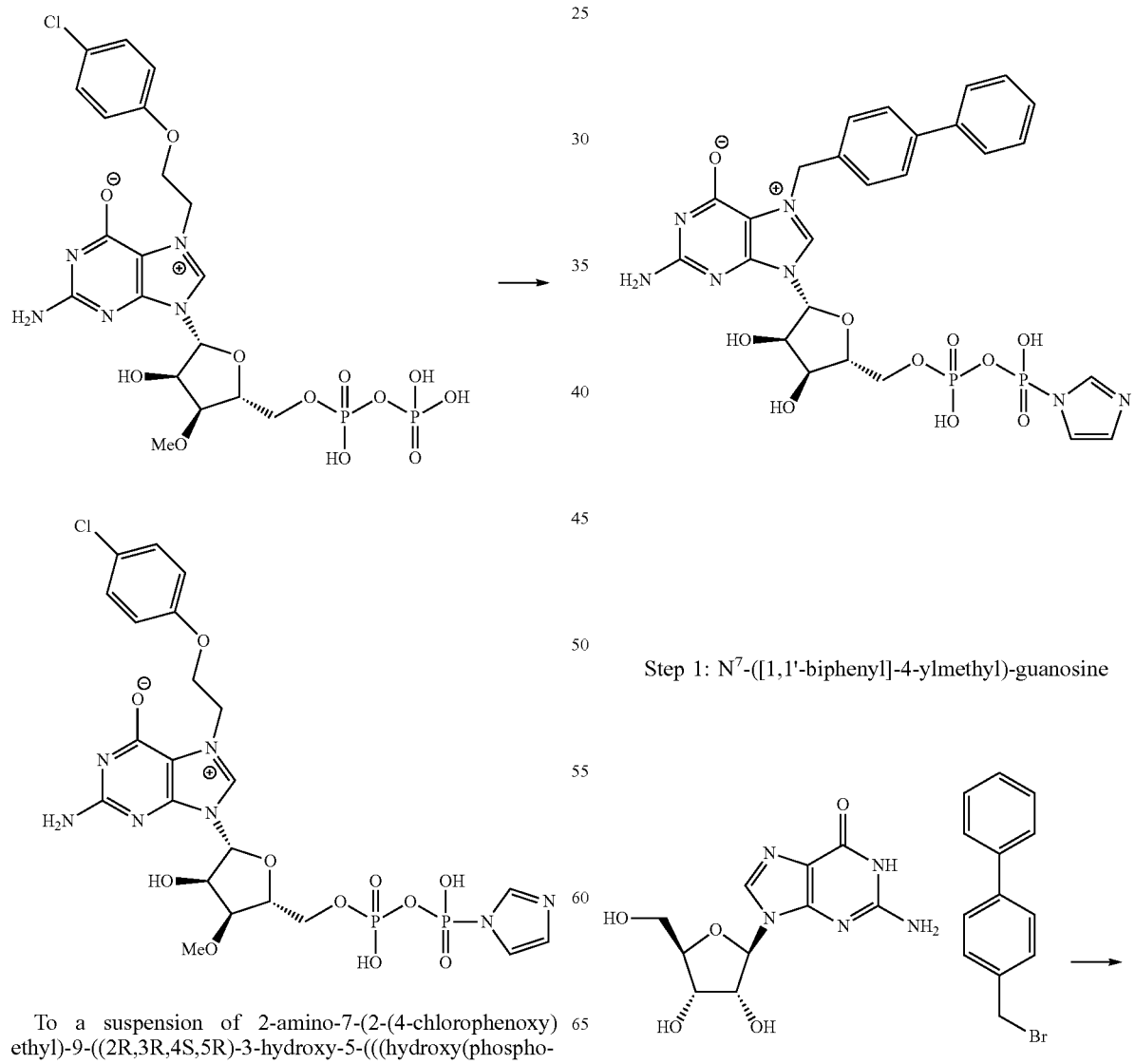

Step 1: N⁷-([1,1'-biphenyl]-4-ylmethyl)-guanosine

-continued

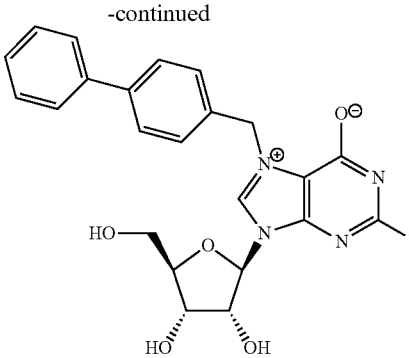

Guanosine (2.65 mmol) and 4-bromomethylbiphenyl (6.07 mmol) were taken up in anhydrous DMSO (7.5 ml) and stirred at RT for 60 h. The reaction was diluted with DMSO and purified on prepatory RP-HPLC. Pooled product fractions were concentrated while azeotroping with toluene, taken up in 1:1 H₂O/acetonitrile, frozen, and lyophilized to give the trifluoroacetate salt of the title compound as a white solid. LCMS method 1 R$_t$=0.94 mins; MS m/z [M+H]⁺ 450.0.

Step 2: 7-([1,1'-biphenyl]-4-ylmethyl)-2-amino-9-((2R,3R,4S,5R)-3,4-dihydroxy-5-(((hydroxy(phosphonomethyl)phosphoryl)oxy)methyl)tetrahydrofuran-2-yl)-6-oxo-6,9-dihydro-1H-purin-7-ium

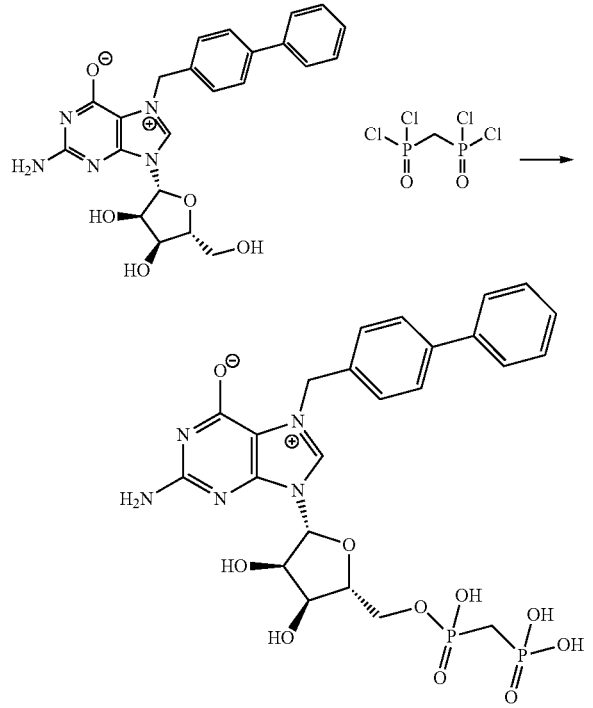

To a solution of N⁷-([1,1'-biphenyl]-4-ylmethyl)-guanosine (0.266 mmol) in 1.0 ml of trimethyl phosphate at −10° C. was slowly added a solution of methylenediphosphonic dichloride (1.00 mmol) in 1.0 ml trimethylphosphate cooled to −10° C. The reaction stirred at −10° C.–0° C. for 6.5 h and then sat at −20° C. for 60 h. The reaction was slowly quenched by adding it to 1M TEAB (9 ml) at 0° C. Upon completion of the addition, the reaction was warmed to RT to ensure quenching of the excess methylenediphosphonic dichloride. The resulting solution was purified directly on prepatory HPLC [(Phenomenex Gemini-NX 5 μm C18 100 mm×30 mm column; 0-15 min: 10 to 40% ACN/0.1M TEAB in H₂O, 25 ml/min)]. Product fractions were pooled, frozen, and lyophilized to afford the triethylammonium salt of the title compound as a white solid (16 mg, 0.02 mmol, 7%). LCMS method 2 R$_t$=1.46 mins; MS m/z [M+H]⁺ 608.1; ¹H NMR (D₂O) 6:9.51 (s, 1H), 7.25-7.35 (m, 4H), 7.10-7.25 (m, 5H), 5.70 (d, J=3.4 Hz, 1H), 5.42-5.58 (m, 2H), 4.50 (t, J=3.9 Hz, 1H), 4.40 (t, J=5.1 Hz, 1H), 4.28-4.33 (m, 1H), 4.20-4.28 (m, 1H), 4.06-4.17 (m, 1H), 3.12 (q, J=7.3 Hz, NEt₃), 2.17 (t, J=19.7 Hz, 2H), 1.20 (t, J=7.3 Hz, NEt₃).

Step 3: 7-([1,1'-biphenyl]-4-ylmethyl)-2-amino-9-((2R,3R,4S,5R)-3,4-dihydroxy-5-(((hydroxy((hydroxy(1H-imidazol-1-yl)phosphoryl)methyl)phosphoryl)oxy)methyl)tetrahydrofuran-2-yl)-6-oxo-6,9-dihydr-1H-purin-7-ium

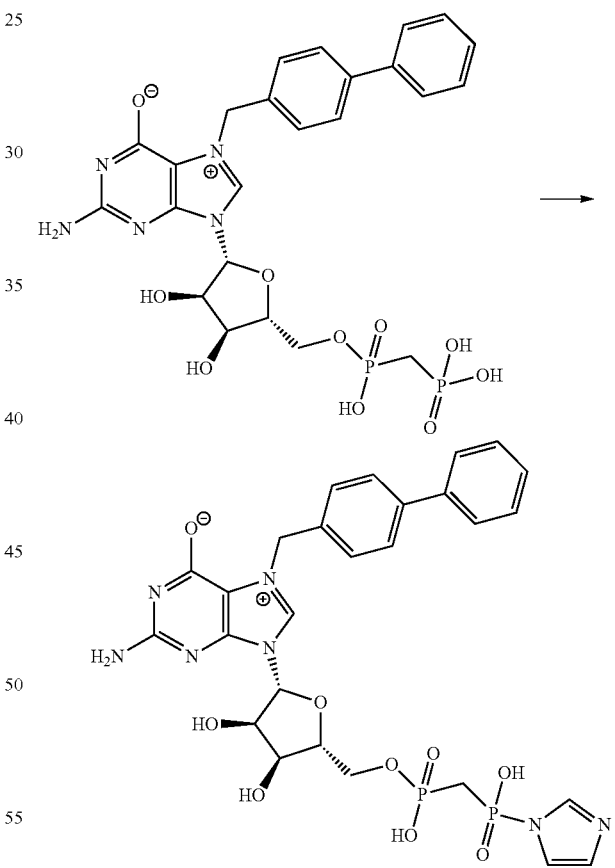

To a solution of 7-([1,1'-biphenyl]-4-ylmethyl)-2-amino-9-((2R,3R,4S,5R)-3,4-dihydroxy-5-(((hydroxy(phosphonomethyl)phosphoryl)oxy)methyl)tetrahydrofuran-2-yl)-6-oxo-6,9-dihydro-1H-purin-7-ium (0.016 mmol) in 1.0 ml of anhydrous DMF was added imidazole (0.176 mmol), 2,2'-dipyridyl disulfide (0.082 mmol) and TEA (0.029 mmol). The reaction stirred at RT for 10 min and then triphenylphosphine (0.084 mmol) was added turning the reaction yellow in color. After stirring at RT for 18 h, 1 M NaClO₄ in acetone (0.250 mmol) was added to the reaction followed by acetone (5 ml) generating a white precipitate. The resulting suspension was cooled at 4° C. for 20 min and centrifuged. The supernatant was decanted and the precipitate washed with acetone (5 ml), cooled at 4° C. for 10 min, and centrifuged. This wash procedure was repeated one more time. The resulting precipitate was dried under vacuum to afford the sodium salt of the title compound as a white solid (10.8 mg, 0.013 mmol, 81%). This compound was used directly in the mRNA capping reaction. LCMS method 5 MS(ES):m/z=657.5 (M−H+).

Example 27: 7-([1,1'-biphenyl]-4-ylmethyl)-2-amino-9-((2R,3R,4S,5R)-3,4-dihydroxy-5-(((hydroxy((hydroxy(1H-imidazol-1-yl)phosphoryl)amino)phosphoryl)oxy)methyl)tetrahydrofuran-2-yl)-6-oxo-6,9-dihydro-1H-purin-7-ium $N^7$-([1,1'-biphenyl]-4-ylmethyl)-guanosine (0.177 mmol) was added to a solution of dichlorophosphinylphosphorimidic trichloride (J. Emsley, J. Moore, P. B. Udy, J. Chem. Soc. A 1971, 2863-2864; 0.891 mmol) in trimethylphosphate (2.0 ml) at 0° C. The reaction stirred at 0° C. for 1.5 h and was then cooled to −20° C. and sat for 16 h. The reaction was warmed to 0° C. and additional dichlorophosphinylphosphorimidic trichloride (0.891 mmol) was added to the reaction. The reaction stirred at 0° C. for 5 h until only traces of the starting material remained as monitored by LCMS (Method 2 RXNMON_Acidic_Polar_PosNeg.olp-ZQ1). The reaction was quenched by slowly adding it to 1M TEAB (10 ml) at 0° C. Upon completion of the addition, the reaction was warmed to RT to ensure quenching of the excess dichlorophosphinylphosphorimidic trichloride. The resulting suspension was filtered and the filtrate subjected to preparatory HPLC [(Phenomenex Gemini-NX 5 jim C18 100 mm×30 mm column; 0-15 min: 10 to 50% ACN/0.1M TEAB in $H_2O$, 25 ml/min)]. Product fractions were pooled, frozen, and lyophilized to the triethylammonium salt of the title compound as a white solid (13.5 mg, 0.018 mmol, 10%). LCMS method 6 Calc.: 608.1186; Found: 609.1290 [M+H+]; $^1$H NMR ($D_2O$) δ: 9.51 (s, 1H), 7.49-7.57 (m, 4H), 7.38-7.44 (m, 4H), 7.31-7.38 (m, 1H), 5.90 (d, J=3.6 Hz, 1H), 5.55-5.68 (m, 2H), 4.63 (t, J=4.3 Hz, 1H), 4.48 (t, J=5.1 Hz, 1H), 4.29-4.38 (m, 1H), 4.17-4.26 (m, 1H), 4.04-4.17 (m, 1H), 3.13 (q, J=7.3 Hz, $NEt_3$), 1.21 (t, J=7.3 Hz, $NEt_3$).

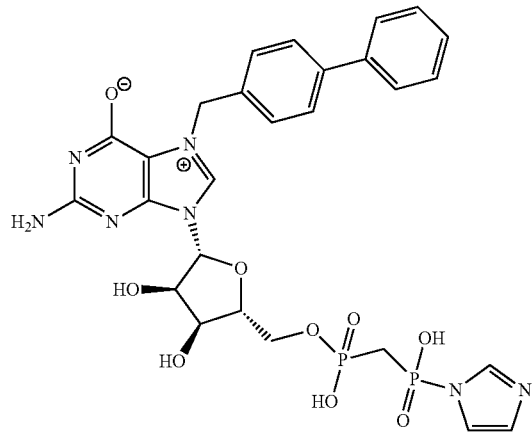 [SMILES: Nc1nc([O-])c2c(n1)n([C@@H]1O[C@H](COP(=O)(O)CP(=O)(O)n3ccnc3)[C@@H](O)[C@H]1O)c[n+]2Cc1ccc(-c2ccccc2)cc1]

Step 1: 7-([1,1'-biphenyl]-4-ylmethyl)-2-amino-9-((2R,3R,4S,5R)-3,4-dihydroxy-5-(((hydroxy(phosphonoamino)phosphoryl)oxy)methyl)tetrahydrofuran-2-yl)-6-oxo-6,9-dihydro-1H-purin-7-ium

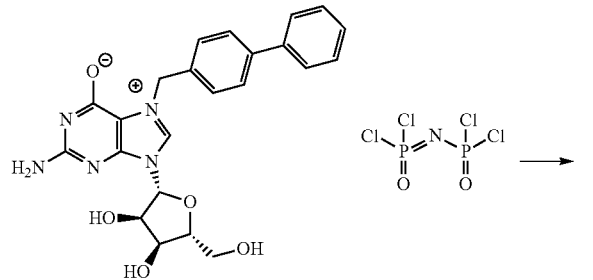

Step 2: 7-([1,1'-biphenyl]-4-ylmethyl)-2-amino-9-((2R,3R,4S,5R)-3,4-dihydroxy-5-(((hydroxy((hydroxy(1H-imidazol-1-yl)phosphoryl)amino)phosphoryl)oxy)methyl)tetrahydrofuran-2-yl)-6-oxo-6,9-dihydro-1H-purin-7-ium

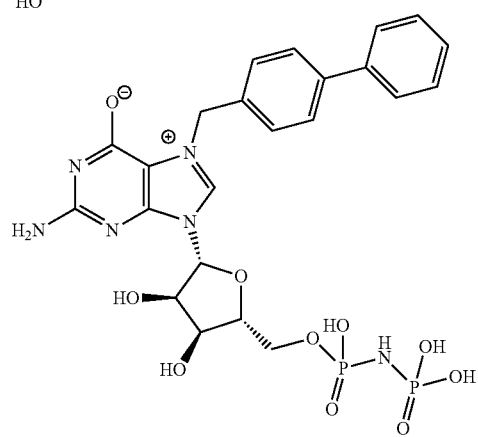
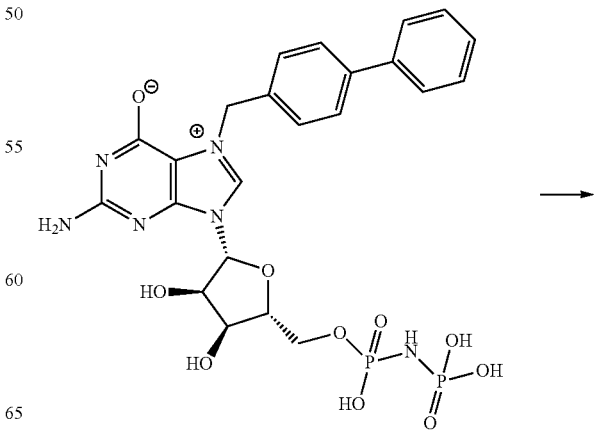

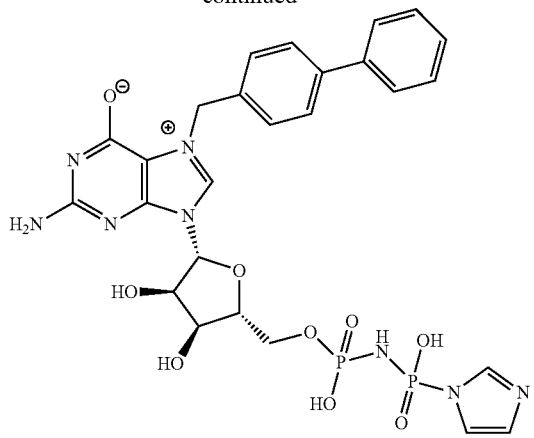

7-([1,1'-biphenyl]-4-ylmethyl)-2-amino-9-((2R,3R,4S,5R)-3,4-dihydroxy-5-(((hydroxy(phosphonoamino)phosphoryl)oxy)methyl)tetrahydrofuran-2-yl)-6-oxo-6,9-dihydro-1H-purin-7-ium (0.007 mmol) was taken up in 1.0 ml of anh. DMF and imidazole (0.073 mmol), 2,2'-dipyridyl disulfide (0.036 mmol) and TEA (0.014 mmol) was added. The reaction stirred at RT for 5 min and then triphenylphosphine (0.038 mmol) was added turning the reaction yellow in color. After stirring at RT for 16 h, 1M NaClO$_4$ in acetone (0.100 mmol) was added to the reaction followed by acetone (5 ml) generating a white precipitate. The resulting suspension was cooled at 4° C. for 20 min and centrifuged. The supernatant was decanted and the precipitate washed with acetone (5 ml), cooled at 4° C. for 10 min, and centrifuged. This wash procedure was repeated one more time. The resulting precipitate was dried under vacuum to give the sodium salt of the title compound as a white solid (2.3 mg, 3.4 μmol, 33%). This compound was used directly in the mRNA capping reaction. LCMS method 5 MS(ES−):m/z=658.3 (M−H+).

Analytical data for imidazole activated GDP derivatives are presented in Table 5. The following examples were prepared according to the general procedure for imidazole activation described above or analogously to the methods described in Example 21-27.

TABLE 5

Analytical data for imidazole activated GDP derivatives.

| No. | —Y—R$^1$ | R$^3$ | R$^4$ | R$^2$ | LC/MS method | R$_t$ | Calc. mass [M − H]$^-$ | Exp. Mass [M − H]$^-$ |
|---|---|---|---|---|---|---|---|---|
| 1 | Me | H | H | NH$_2$ | 5 | — | 507.3 | 507.3 |
| 2 | Me | H | Me | NH$_2$ | 5 | — | 521.3 | 521.4 |
| 3 | propyloxy-(4-Cl-phenyl) | H | H | NH$_2$ | 2 | 1.14' | 645.8 | 646.1 |
| 4 | propyloxy-(4-Cl-phenyl) | Me | H | NH$_2$ | 5 | — | 661.9 | 661.4 |
| 5 | propyloxy-(4-Cl-phenyl) | H | Me | NH$_2$ | 5 | — | 661.9 | 661.4 |
| 6 | ethyl-(3-F-biphenyl) | H | H | NH$_2$ | 5 | — | 676.1 | 676.4 |
| 7 | ethyl-(3-MeO-biphenyl) | H | H | NH$_2$ | 5 | — | 688.1 | 688.4 |

TABLE 5-continued

Analytical data for imidazole activated GDP derivatives.

| No. | —Y—R¹ | R³ | R⁴ | R² | LC/MS method | $R_t$ | Calc. mass [M − H]⁻ | Exp. Mass [M − H]⁻ |
|---|---|---|---|---|---|---|---|---|
| 8 | 3-F-benzyl (ethyl linker) | H | H | NH₂ | 5 | — | 600.1 | 600.3 |
| 9 | 3,5-dimethylbenzyl (ethyl linker) | H | H | NH₂ | 5 | — | 610.1 | 610.3 |
| 10 | 2-chloro-4-biphenyl (ethyl linker) | H | H | NH₂ | 5 | — | 692.1 | 692.3 |
| 11 | 1,1-diphenylethyl | H | H | NH₂ | 5 | — | 658.1 | 658.4 |
| 12 | 3-ethyl-6-phenyl-2-pyridinone | H | H | NH₂ | 5 | — | 675.1 | 675.4 |
| 13 | 4-(5-methyl-1,2,4-oxadiazol-3-yl)phenyl (ethyl linker) | H | H | NH₂ | 2 | 1.00 | 666.3 | 666.1 |
| 14 | 5-bromo-2-thienyl (ethyl linker) | H | H | NH₂ | 2 | 1.06 | 669.9 | 668.0 |
| 15 | N-(3-chlorophenyl)propanamide | H | H | NH₂ | 2 | 1.16 | 661.1 | 661.1 |
| 16 | 4-(thien-2-yl)phenyl (ethyl linker) | H | H | NH₂ | 2 | 1.36 | 666.1 | 666.1 |

TABLE 5-continued

Analytical data for imidazole activated GDP derivatives.

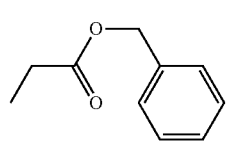

| No. | —Y—R¹ | R³ | R⁴ | R² | LC/MS method | $R_t$ | Calc. mass $[M - H]^-$ | Exp. Mass $[M - H]^-$ |
|---|---|---|---|---|---|---|---|---|
| 17 | 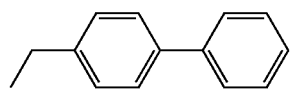 | H | H | NH₂ | 2 | 1.01 | 642.1 | 642.1 |
| 18 | 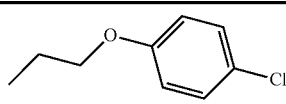 | H | H | H | 2 | 1.32' | 644.2 | 644.1 |

Analytical data for imidazole activated GMP derivatives are presented in Table 6. The following examples were prepared according to the general procedure for imidazole activation described above or analogously to the methods described in Example 21-27.

TABLE 6

Analytical data for imidazole activated GMP derivatives.

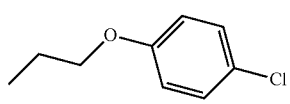

| No. | —Y—R¹ | R³ | R⁴ | LC/MS method | $R_t$ | Calc. mass $[M + H]^+$ | Exp. Mass $[M + H]^+$ |
|---|---|---|---|---|---|---|---|
| 1 | 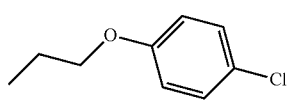 | H | H | 2 | 1.20' | 567.1 | 567.9 |
| 2 | 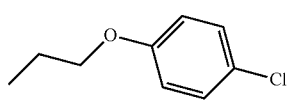 | H | Me | 2 | 1.20' | 582.9 | 532.9 |
| 3 | 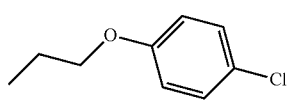 | Me | H | 2 | 1.18' | 582.9 | 582.9 |

TABLE 6-continued

Analytical data for imidazole activated GMP derivatives.

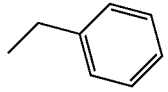

| No. | —Y—R¹ | R³ | R⁴ | LC/MS method | $R_t$ | Calc. mass $[M + H]^+$ | Exp. Mass $[M + H]^+$ |
|---|---|---|---|---|---|---|---|
| 4 | 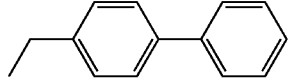 | H | H | 2 | 0.85' | 505.1 | 505.2 |
| 5 |  | H | H | 2 | 1.32' | 578.5 | 577.9 |

For capping of oligonucleotides and RNAs, the imidazole activated mono- and diphosphates, obtained in the examples shown above, were dissolved in RNAse-free water to give a 20 mM solution of the imidazole activated GMP/GDP derivative in $H_2O$ (based on the amount of activated imidazole present in the sample as determined by $^1$H-NMR).

General Procedure for the 3' End Modification of Oligo Nucleotides:

The oligos 5-/5Phos/rGrArAr ArArA rArArAr ArA-3 (oligonucleotide 1) and 5-/5Phos/rGrU/iFluorT/rUrCrG rCr-CrA rUrU/i6-TAMN/rArArA rArArA rArArA rA-3 (oligonucleotide 2) were purchased from IDT.

Procedure A (Condensation Reactions):

A solution containing 10 μM oligonucleotide in PBS buffer was treated with 50×NaIO₄ (5 mM stock solution, 500 μM final conc.) and kept at 0° C. for 1 h. The solution obtained was treated with 100×Na₂SO₃ (10 mM stock solution, 1 mM final conc.) and brought to RT. After 10 min, 100× of the nucleophile in water was added (10 mM stock solution, 1 mM final conc.) and the solution was kept at RT over night. The solution was desalted using Princeton Separation CS100 spin columns.

Procedure B (Reductive Amination Reactions):

A solution containing 10 μM oligonucleotide in PBS buffer was treated with 50×NaIO₄ (5 mM stock solution, 500 μM final conc.) and kept at 0° C. for 1 h. The solution obtained was treated with 200×Na₂SO₃ (10 mM stock solution, 2 mM final conc.) and brought to RT. After 10 min, 100× of the nucleophile (10 mM stock solution in water, 1 mM final conc.) and NaBH3CN (100 mM stock solution in water, 10 mM final conc.) were added. The solution was shaken at 37° C. over night and desalted using Princeton Separation CS100 spin columns.

Analytical data for 3'-modified oligonucleotides are presented in Table 7. The following examples were prepared according to the general procedure described above.

TABLE 7

Analytical data for 3'-modified oligonucleotides.

[Structure: adenine-deoxyribose with R1^a at 3' position and 5'-phosphate linked to 5'-oligonucleotide-3']

| No. | R1^a | Oligo nucleotide | Synthetic method | R_t^c | Calc. mass | Exp. Mass |
|---|---|---|---|---|---|---|
| 1 | HO–CH(–O–)CH–OH (wavy bonds) | 1 | A^b | 1.92' | 3572.5 [M − H]⁻ | 3571.3 [M − H]⁻ |
| 2 | HO–CH(–N(Me)–NH–N–)CH–OH (wavy bonds) | 1 | A | 1.54' | 3600.4 [M − H]⁻ | 3600.2 [M − H]⁻ |

TABLE 7-continued
Analytical data for 3'-modified oligomucleotides.
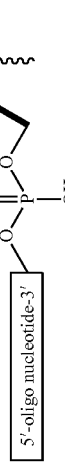
| No. | R1$^a$ | Oligo nucleotide | Synthetic method | R$_t^c$ | Calc. mass | Exp. Mass |
|---|---|---|---|---|---|---|
| 3 |  | 2 | A | 3.17' | 8180.5 [M − H$_3$O]$^-$ | 8180.5 [M − H$_3$O]$^-$ |
| 4 |  | 1 | B | 1.83' | 3587.4 [M − H]$^-$ | 3587.0 [M − H]$^-$ |
| 5 |  | 1 | A | 1.69' | 3628.4 [M − H]$^-$ | 3630.1 [M − H]$^-$ |

TABLE 7-continued

Analytical data for 3'-modified oligonucleotides.

| No. | R1$^a$ | Oligo nucleotide | Synthetic method | R$_t^c$ | Calc. mass | Exp. Mass |
|---|---|---|---|---|---|---|
| 6 | (acetyl hydrazide piperidine) | 1 | B | 1.76 | 3614.4 [M − H]$^-$ | 3613.1 [M − H]$^-$ |
| 7 | (N-methoxy bis-hydroxymethyl) | 1 | A | 1.32' | 3601.3 [M − H]$^-$ | 3601.1 [M − H]$^-$ |
| 8 | (N-methoxy piperidine) | 1 | B | 2.02' | 3587.3 [M − H]$^-$ | 3587.4 [M − H]$^-$ |

TABLE 7-continued

Analytical data for 3'-modified oligonucleotides.

| No. | R1$^a$ | Oligo nucleotide | Synthetic method | R$_t^c$ | Calc. mass | Exp. Mass |
|---|---|---|---|---|---|---|
| 9 | | 2 | A | 3.76 | 9040.4 [M − H]$^-$ | 9037.5 [M − H]$^-$ |
| 10 | | 1 | A | 4.09' | 4926.9 [M − H]$^-$ | 4928.1 [M − H]$^-$ |

TABLE 7-continued
Analytical data for 3'-modified oligonucleotides.
| No. | R1$^a$ | Oligo nucleotide | Synthetic method | R$_t^c$ | Calc. mass | Exp. Mass |
|---|---|---|---|---|---|---|
| 11 | 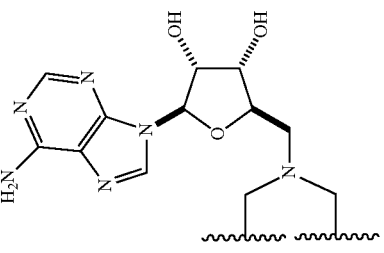 | 1 | B | 1.68$^i$ | 3806.5 [M − H]$^−$ | 3806.5 [M − H]$^−$ |
| 12 |  | 1 | A | 1.91$^i$ | 3699.4 [M − H$_3$O]$^−$ | 3699.3 [M − H$_3$O]$^−$ |
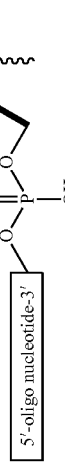

TABLE 7-continued
Analytical data for 3'-modified oligonucleotides.
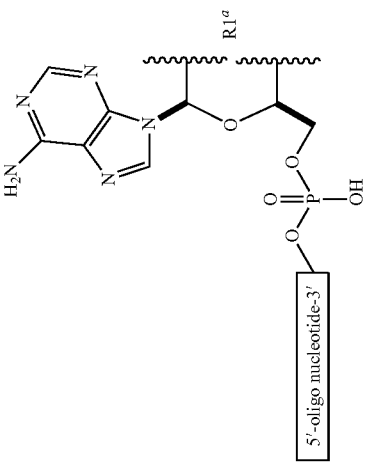
| No. | R1[a] | Oligo nucleotide | Synthetic method | $R_f^c$ | Calc. mass | Exp. Mass |
|---|---|---|---|---|---|---|
[a]Structure shown represent one of the possible regioisomeric condensation products.
[b]Compound obtained if no nucleophile was added.
[c]LCMS method 9

General Procedure for the 3' End Modification of mRNA:

mRNA in water (0.5-1.5 mg/mL, 90 µL) was treated with NaIO$_4$ (0.1 M in 3 M NaOAc buffer, pH 5.2, final conc. 10 mM), and the solution was kept on ice in the dark for 1 h. The sample was desalted using Princeton Separations Centrispin columns, equilibrated with PBS buffer. The solution was treated with the appropriate nucleophile (in H$_2$O or DMSO for a final concentration of 5 mM), diluted 0.75× with H$_2$O and shaken at 500 rpm at room temperature for 2 h. The resulting solution was desalted twice with Princeton Separations CentriSpin 10 columns (PBS equilibrated, then H$_2$O equilibrated). The RNA solutions obtained were further purified by LiCl precipitation.

BIOLOGICAL DATA

Analysis of Cap Analog Binding to Biotinylated and Surface Immobilized hEIF4E:

Dual histidine and Avi tagged human EIF4E (His6-3C-avi-eIF4E) was expressed in 8 L of TB Media. Induction by 0.4 mM IPTG occurred at 2.0 OD600, and cells were harvested at 15 OD600. 225 gram pellet was diluted in buffer (50 mM Tris, 500 mM NaCl, 2 mM MgCl2, 1 mM TCEP, pH 7.5 containing 10% glycerol, protease inhibitors, and DNase) to volume of 600 mL and passed once over the microfluidizer. Sample was run on 5 mL HisTrap HP IMAC at 4.0 mL/min IMAC with a 25 mM to 500 mM imidazole gradient for one column volume. GST-PreScission Protease (2 mg, made in-house) was added to sample and allowed to react overnight at 4° C. The cleaved pool was passed over 0.5 mL GST and 0.5 IMAC resin in a gravity column. Sample volume was increased to 800 mL using 50 mM Tris pH 7.5, 1 mM TCEP and passed over a 5 mL hiTrap SP FF at 4.0 mL/min with a 0 to 1 M NaCl gradient over 20 column volumes. Sample was then injected onto a 124 mL S75 Gel Filtration Column at 20 mg/mL. Final Avi-eIF4E (26931 Da) was diluted to 1 mg/mL in 1× Bicine buffer to a volume of 2.5 mg and mixed with ATP/Biotin Mix (10 mM ATP, 10 mM Mg(OAc)$_2$, 50 µM d-biotin final). Biotin Ligase (25 µg BirA produced in house) was added to reaction. Reactions were performed with mixing (500 rpm) on Eppendorf ThermoMixer R at 30° C. for 60 minutes and checked for completeness using LC-MS. To the sample, 100 µl of immobilized glutathione (1:1 with buffer) was add and mixed for 15 min at 4° C. to bind C3 and Bir3 and removed by centrifugation. The sample was buffer exchanged using two consecutive PD-10 columns equilibrated with 20 mM HEPES, 100 mM KCl, 1 mM DTT, pH 7.5.

Due to low eIF4E stability, the streptavidin coated chip was prepared and run at 10° C. on the Biacore T200. The eIF4E (0.04 mg/mL, 150 µl) was bound to the sample channel of Series S Sensor Chip SA (GE Life Sciences, BR-1005-31) to surface density of 5000 to 7000 RU (Response Units). Buffer flowed over the chip at 30 µL/min, using 1×PBS, 50 mM NaCl, 0.1% Glycerol, 0.1% CHAPS, and 1% DMSO. Samples of various cap analogs were diluted to various concentrations in a range of 100 µM to less than 1 nM. Samples were injected into the Biacore chip with a two minute association time and a five minute dissociation time. Several buffer injections were done for each sample for blank subtraction.

Analysis was done for all sets using Biacore T200 evaluation software. Binding analysis for all compounds is reported as response units at 1 micromolar compound where a higher value for RU is interpreted as greater ligand binding to the surface immobilized eIF4E protein. A subset of compounds was further characterized to determine dissociation constants using either or both kinetic binding and thermodynamic (Steady State Affinity) binding analysis. Steady State Affinity fits were done with default settings (4 seconds before injection stop with 5 second window). Kinetic fits were normally done with 1:1 binding model, with constant RI=0 and all other variables set to fit globally.

Biacore binding data of cap analogs using the above described method is presented in Table 8.

TABLE 8

Biacore binding data of cap analogs.

| No. | —Y—R$^1$ | R$^4$ | Molecular Weight (Da) | Binding Level (RU) at 1 µM | K$_D$ (µM) Kinetic | K$_D$ (µM) Steady State/ Thermodynamic |
|---|---|---|---|---|---|---|
| 1 | (ethyl-biphenyl) | OH | 530.5 | 127.5 | 0.1 | 0.3 |

TABLE 8-continued
Biacore binding data of cap analogs.
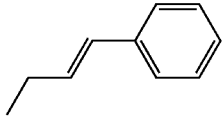
| No. | —Y—R$^1$ | R$^4$ | Molecular Weight (Da) | Binding Level (RU) at 1 μM | K$_D$ (μM) Kinetic | K$_D$ (μM) Steady State/ Thermodynamic |
|---|---|---|---|---|---|---|
| 2 | 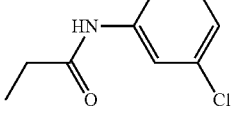 | OH | 682.78 | 14.8 | N/D | N/D |
| 3 | 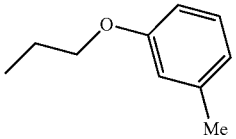 | OH | 645.82 | 5.4 | N/D | N/D |
| 4 | 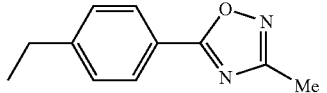 | OH | 612.42 | 18.0 | N/D | N/D |
| 5 | 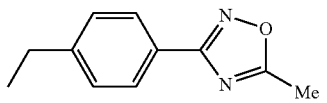 | OH | 650.42 | 3.1 | N/D | N/D |
| 6 | 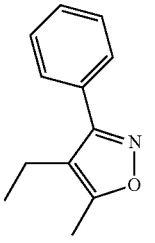 | OH | 650.42 | 1.2 | N/D | N/D |
| 7 | 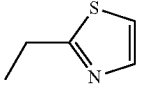 | OH | 649.42 | 4.9 | N/D | N/D |
| 8 | 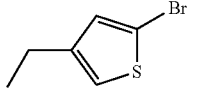 | OH | 575.42 | 12.3 | N/D | N/D |
| 9 | 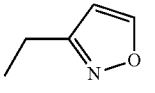 | OH | 653.32 | 42.9 | N/D | N/D |
| 10 |  | OH | 559.32 | 6.6 | N/D | N/D |

TABLE 8-continued
Biacore binding data of cap analogs.
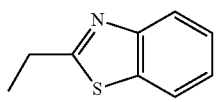
| No. | —Y—R$^1$ | R$^4$ | Molecular Weight (Da) | Binding Level (RU) at 1 µM | K$_D$ (µM) Kinetic | K$_D$ (µM) Steady State/ Thermodynamic |
|---|---|---|---|---|---|---|
| 11 | 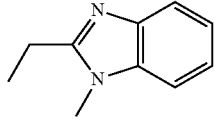 | OH | 625.42 | 11.5 | N/D | N/D |
| 12 | 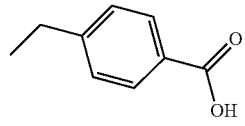 | OH | 622.42 | 1.6 | N/D | N/D |
| 13 | 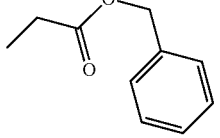 | OH | 612.42 | 3.8 | N/D | N/D |
| 14 | 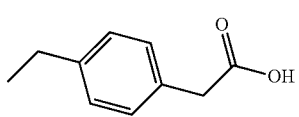 | OH | 626.42 | 1.6 | N/D | N/D |
| 15 | 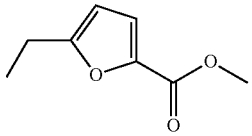 | OH | 626.42 | 17.4 | N/D | N/D |
| 16 | 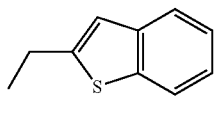 | OH | 616.42 | 15.4 | N/D | N/D |
| 17 | 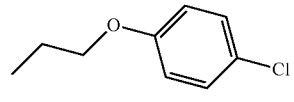 | OH | 624.42 | 16.8 | 0.03 | — |
| 18 | 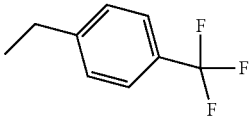 | OMe | 554.89 | 109.9 | 0.18 | 0.16 |
| 19 |  | OH | 636.42 | 7.1 | N/D | N/D |

TABLE 8-continued

Biacore binding data of cap analogs.

| No. | —Y—R¹ | R⁴ | Molecular Weight (Da) | Binding Level (RU) at 1 μM | $K_D$ (μM) Kinetic | $K_D$ (μM) Steady State/ Thermodynamic |
|---|---|---|---|---|---|---|
| 20 | 4-tert-butylbenzyl | OH | 624.52 | 4.3 | N/D | N/D |
| 21 | 2,6-dichlorobenzyl | OH | 637.22 | 2.7 | N/D | N/D |
| 22 | 4-(methoxycarbonyl)benzyl | OH | 626.42 | 72.6 | N/D | N/D |
| 23 | 4-nitrobenzyl | OH | 613.42 | 8.6 | N/D | N/D |
| 24 | 3-fluorobenzyl | OH | 586.32 | 37.4 | N/D | N/D |
| 25 | 4-cyanobenzyl | OH | 593.42 | 47.4 | N/D | N/D |
| 26 | 3-methoxybenzyl | OH | 598.42 | 6.7 | 0.05 | $4.4 \times 10^{-3}$ |
| 27 | 4-(benzyloxy)benzyl | OH | 674.52 | 17.3 | N/D | N/D |

TABLE 8-continued
Biacore binding data of cap analogs.
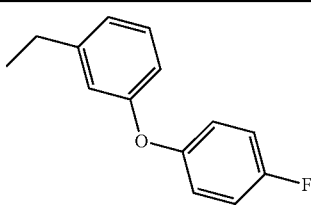
| No. | —Y—R¹ | R⁴ | Molecular Weight (Da) | Binding Level (RU) at 1 μM | $K_D$ (μM) Kinetic | $K_D$ (μM) Steady State/ Thermodynamic |
|---|---|---|---|---|---|---|
| 28 | 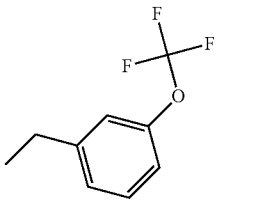 | OH | 678.42 | 56.3 | N/D | N/D |
| 29 | 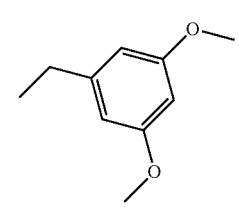 | OH | 652.42 | −2.6 | 0.03 | $3.74 \times 10^{-3}$ |
| 30 | 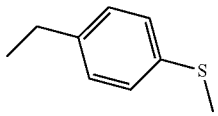 | OH | 628.42 | 10.7 | N/D | N/D |
| 31 | 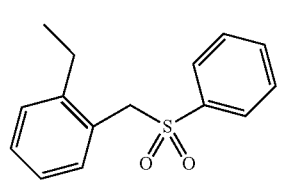 | OH | 614.52 | 10.4 | N/D | N/D |
| 32 | 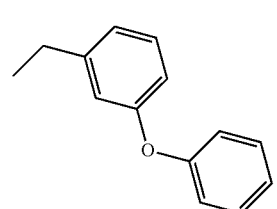 | OH | 722.52 | 1.0 | 93.6 | 0.03 |
| 33 |  | OH | 660.52 | 73.9 | 0.17 | 0.22 |

TABLE 8-continued
Biacore binding data of cap analogs.
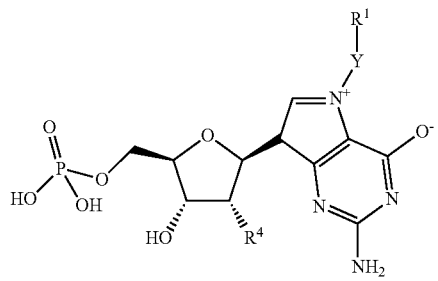
| No. | —Y—R¹ | R⁴ | Molecular Weight (Da) | Binding Level (RU) at 1 μM | $K_D$ (μM) Kinetic | $K_D$ (μM) Steady State/ Thermodynamic |
|---|---|---|---|---|---|---|
| 34 | 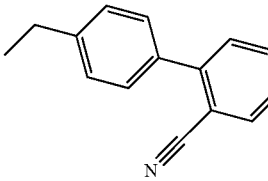 | OH | 669.52 | 8.1 | N/D | N/D |
| 35 | 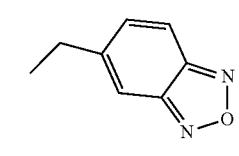 | OH | 610.42 | 13.1 | N/D | N/D |
| 36 | 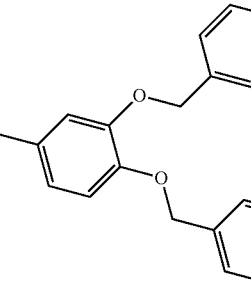 | OH | 780.62 | 2.2 | N/D | N/D |
| 37 | 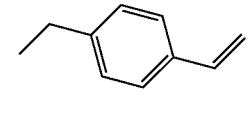 | OH | 594.42 | 31.5 | N/D | N/D |
| 38 | 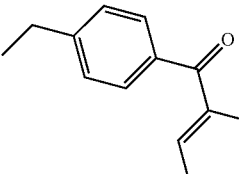 | OH | 672.52 | 29.6 | N/D | N/D |
| 39 | 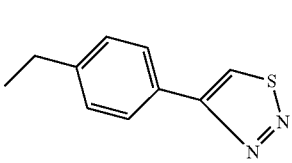 | OH | 652.52 | 38.8 | N/D | N/D |

TABLE 8-continued

Biacore binding data of cap analogs.

| No. | —Y—R¹ | R⁴ | Molecular Weight (Da) | Binding Level (RU) at 1 µM | $K_D$ (µM) Kinetic | $K_D$ (µM) Steady State/ Thermodynamic |
|---|---|---|---|---|---|---|
| 40 | (3-ethylphenyl)-C(=O)-NH-(thiophene-2-carboxylate methyl ester) | OH | 751.52 | 40.6 | 2.36 | $1.22 \times 10^{-3}$ |
| 41 | (4-ethylphenyl)-C(=O)-O-(2,6-dichlorophenyl) | OH | 757.42 | 2.0 | 8.82 | 0.02 |
| 42 | (3-ethylphenyl)-C(=O)-NH-(thiophene-3-carboxylate methyl ester) | OH | 751.52 | 82.5 | 4.9 | $1.98 \times 10^{-3}$ |
| 43 | (3-ethylphenyl)-O-CH₂-phenyl | OH | 674.52 | 36.6 | 3.17 | 0.58 |
| 44 | (4-ethylphenyl)-S(=O)₂-Me | OH | 646.42 | 1.5 | N/D | N/D |
| 45 | 3,5-dimethyl-ethylphenyl | OH | 596.42 | 9.4 | N/D | N/D |

TABLE 8-continued

Biacore binding data of cap analogs.

| No. | —Y—R[1] | R[4] | Molecular Weight (Da) | Binding Level (RU) at 1 μM | $K_D$ (μM) Kinetic | $K_D$ (μM) Steady State/ Thermodynamic |
|---|---|---|---|---|---|---|
| 46 | ethyl-1-methyl-6-yl-indazole | OH | 622.42 | −3.4 | N/D | N/D |
| 47 | ethyl-phenyl-1,2,4-triazole | OH | 635.42 | 15.7 | N/D | N/D |
| 48 | ethyl-1-methyl-4-yl-indazole | OH | 622.42 | 12.7 | N/D | N/D |
| 49 | ethyl-2′-methyl-biphenyl | OH | 544.50 | 53.3 | 0.02 | $2.11 \times 10^{-3}$ |
| 50 | ethyl-biphenyl-acetyl | OH | 572.50 | 3.8 | N/D | N/D |
| 51 | ethyl-2-phenyl-thiazole | OH | 651.52 | 8.9 | N/D | N/D |
| 52 | ethyl-2′-methoxy-biphenyl | OH | 661.69 | 7.3 | N/D | N/D |
| 53 | MeO-ethyl-biphenyl | OH | 560.50 | 149.9 | 0.19 | $2.16 \times 10^{-2}$ |

TABLE 8-continued

Biacore binding data of cap analogs.

| No. | —Y—R$^1$ | R$^4$ | Molecular Weight (Da) | Binding Level (RU) at 1 μM | K$_D$ (μM) Kinetic | K$_D$ (μM) Steady State/ Thermodynamic |
|---|---|---|---|---|---|---|
| 54 | [4-ethyl-3-fluoro-biphenyl] | OH | 548.40 | 22.2 | 2.78 | $4.75 \times 10^{-2}$ |
| 55 | [4-ethyl-2'-chloro-biphenyl] | OH | 666.09 | 135.7 | 0.04 | 0.11 |
| 56 | [ethyl-pyridinone-phenyl] | OH | 648.59 | 106.8 | N/D | N/D |
| 57 | [4-ethyl-phenyl-thiophene] | OH | 650.52 | 83.9 | 0.03 | $7.24 \times 10^{-3}$ |
| 58 | [4-ethyl-2'-fluoro-biphenyl] | OH | 662.42 | 95.9 | 1.00 | 0.41 |
| 59 | [4-ethyl-phenyl-triazole] | OH | 635.42 | 7.6 | N/D | N/D |

N/D = not determined

FRET Assay for Competitive Binding of Cap Analogs to EIF4E

Materials:

His tagged eIF4E protein was purchased from Fitzgerald Industries International (80R-125; Acton, Mass.) and tRNA was purchased from SIGMA (R5636; St. Louis, Mo.). A biotinylated 20 nucleotide RNA oligo (5'Phos/rGrGrA rCr-CrC rCrUrC rUrCrC rCrUrC rCrCrC rCrC biotin-3') was purchased from Integrated DNA Technologies (Coralville, Iowa). Europium labelled anti his antibody was purchased from Perkin Elmer (ADOI 10; Waltham, Mass.) and streptavidin conjugated alexa fluor 647 was purchased from Life Technologies (S32357; Grand Island, N.Y.).

TR-FRET Assay for eIF4E Binding:

The TR-FRET assay was performed in an assay buffer of PBS (pH 7.4), 0.02% Tween, and 0.1% BSA using four separate addition steps. Initially, 5 μl of His-eIF4E (10 nM) and tRNA (0.1 mg/ml) were added into a black walled 384 well small volume plate. Next, 1 al/well of freshly diluted compound was added using the Beckman Coulter Biomek FX liquid dispenser with a final DMSO concentration of 1%. The compound and eIF4E were allowed to bind for 15 minutes at room temperature. The third addition consisted of adding 4 μl of chemically capped 7mGDP imidazole mRNA-biotin (10 nM) into every well, with the exception of one column containing only buffer to use as a background control. The binding reaction was incubated for one hour at room temperature. Finally, 5 al of the europium-labeled anti-His antibody (10 nM) and streptavidin conjugated alexa fluor 647 (10 nM) TR-FRET detection reagents were added to each well and allowed to incubate at room temperature protected from light for 1 h. The plates were read on the Envision plate reader (Perkin-Elmer) to measure signals from both the Alexa fluor (665 nm) and the europium (615 nm). A ratio of the alexa fluor and europium fluorescence as a function of cap analog concentration was calculated for data analysis and data were fit to a standard EC50 inhibition curve in Graph Pad.

FRET assay data for $N^7$-alkylated GMP derivatives using the above described method is presented in Table 9.

TABLE 9

FRET assay data for $N^7$-alkylated GMP derivatives.

| No. | —Y—$R^1$ | $R^3$ | $R^4$ | AC50/μM |
|---|---|---|---|---|
| 1 | 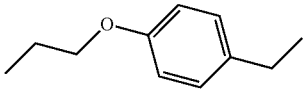 | H | OH | 50.1 |
| 2 | 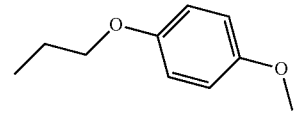 | H | OH | 8.32 |
| 3 | 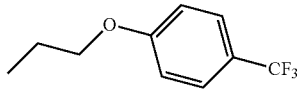 | H | OH | 65.1 |
| 4 | 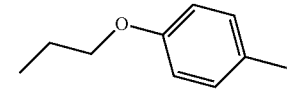 | H | OH | 17.4 |
| 5 | 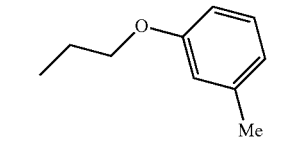 | H | OH | 87.9 |
| 6 | 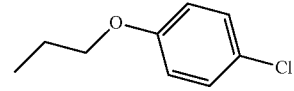 | Me | OH | 0.56 |
| 7 | 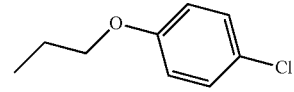 | H | OMe | 0.85 |
| 8 | 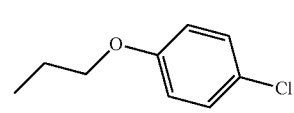 | H | OH | 0.61[e] |

TABLE 9-continued

FRET assay data for $N^7$-alkylated GMP derivatives.

| No. | —Y—$R^1$ | $R^3$ | $R^4$ | AC50/μM |
|---|---|---|---|---|
| 9 | 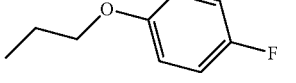 | H | OH | — |
| 10 | 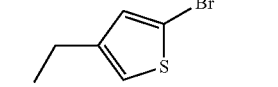 | H | OH | 12.2 |
| 11 | 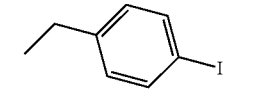 | H | OH | 14.0 |
| 12 | 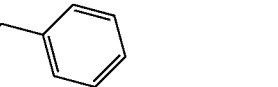 | H | OH | 17.8 |
| 13 | 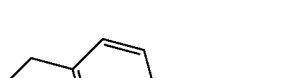 | H | OH | 10.6 |
| 14 | 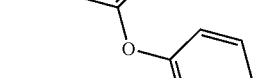 | H | OH | 5.23 |
| 15 | 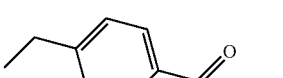 | H | OH | 59.5 |
| 16 |  | H | OH | 22.4 |

TABLE 9-continued

FRET assay data for N⁷-alkylated GMP derivatives.

| No. | —Y—R¹ | R³ | R⁴ | AC50/μM |
|---|---|---|---|---|
| 17 | 3-ethylbenzoyl-NH-thiophene-2-carboxylic acid methyl ester | H | OH | 42.9 |
| 18 | 3-ethylbenzoyl-NH-thiophene-3-carboxylic acid methyl ester | H | OH | 27.7 |
| 19 | 3-ethylphenyl benzyl ether | H | OH | 95.7 |
| 20 | 4-ethyl-1H-imidazole | H | OH | — |
| 21 | 2-ethylthiazole | H | OH | >100 |
| 22 | 3-ethylisoxazole | H | OH | >100 |
| 23 | 4-ethylnitrobenzene | H | OH | >100 |
| 24 | 4-ethyl(methylsulfonyl)benzene | H | OH | >100 |
| 25 | 3-ethyl-methoxybenzene | H | OH | >100 |
| 26 | 4-ethyl(methylthio)benzene | H | OH | >100 |
| 27 | 4-ethylstyrene | H | OH | >100 |
| 28 | 3,5-dimethyl-ethylbenzene | H | OH | >100 |
| 29 | 4-ethylbenzoyl-NH-5-methylisoxazole | H | OH | >100 |
| 30 | 1,1-diphenylethyl | H | OH | >100 |
| 31 | 3-phenyl-4-ethyl-5-methylisoxazole | H | OH | >100 |
| 32 | 4-ethylbenzoic acid | H | OH | >100 |

TABLE 9-continued

FRET assay data for N[7]-alkylated GMP derivatives.

| No. | —Y—R[1] | R[3] | R[4] | AC50/μM |
|---|---|---|---|---|
| 33 | 4-ethylphenylacetic acid | H | OH | >100 |
| 34 | methyl 5-ethylfuran-2-carboxylate | H | OH | >100 |
| 35 | 4-ethyl-(trifluoromethyl)benzene | H | OH | >100 |
| 36 | 4-ethyl-tert-butylbenzene | H | OH | >100 |
| 37 | 2,6-dichloroethylbenzene | H | OH | >100 |
| 38 | 4-ethylphenyl benzyl ether | H | OH | >100 |
| 39 | 3-ethyl-(trifluoromethoxy)benzene | H | OH | >100 |
| 40 | 3,5-dimethoxyethylbenzene | H | OH | >100 |
| 41 | 2-ethylbenzyl phenyl sulfone | H | OH | >100 |
| 42 | 2,3-bis(benzyloxy)ethylbenzene | H | OH | >100 |
| 43 | 2,6-dichlorophenyl 4-ethylbenzoate | H | OH | >100 |
| 44 | 4-ethylbiphenyl | H | OH | 1.58[a] |
| 45 | 3-methoxy-4-ethylbiphenyl | H | OH | 2.59 |
| 46 | 3-ethyl-6-phenylpyridin-2(1H)-one | H | OH | 1.61[b] |
| 47 | 2'-chloro-4-ethylbiphenyl | H | OH | 0.61[b] |

TABLE 9-continued

FRET assay data for N[7]-alkylated GMP derivatives.

| No. | —Y—R[1] | R[3] | R[4] | AC50/μM |
|---|---|---|---|---|
| 48 | 3'-fluoro-biphenyl-ethyl | H | OH | 100[d] |
| 49 | 2'-methyl-biphenyl-ethyl | H | OH | 39.6 |
| 50 | 2'-fluoro-biphenyl-ethyl | H | OH | 2.11 |
| 51 | 4-(1,2,4-triazol-1-yl)phenyl-ethyl | H | OH | 35.7 |
| 52 | 4-(thiophen-2-yl)phenyl-ethyl | H | OH | 2.75 |
| 53 | 4-(pyrazol-1-yl)phenyl-ethyl | H | OH | 24.6 |
| 54 | 4-cyclohexyl-phenyl-ethyl | H | OH | >100 |
| 55 | 4-(1,2,3-thiadiazol-4-yl)phenyl-ethyl | H | OH | 13.8 |
| 56 | 4-benzoyl-phenyl-ethyl | H | OH | >100 |
| 57 | 2-phenyl-4-ethyl-thiazole | H | OH | >100 |
| 58 | 4-(1,2,3-triazol-1-yl)phenyl-ethyl | H | OH | >100 |
| 59 | 2'-cyano-biphenyl-ethyl | H | OH | >100 |
| 60 | 4'-acetyl-biphenyl-ethyl | H | OH | >100 |
| 61 | 4-(3-methyl-1,2,4-oxadiazol-5-yl)phenyl-ethyl | H | OH | 16.7 |
| 62 | 2'-methoxy-biphenyl-ethyl | H | OH | >100 |
| 63 | 4-(5-methyl-1,2,4-oxadiazol-3-yl)phenyl-ethyl | H | OH | >100[b] |
| 64 | 2-ethyl-5-(4-fluorophenyl)oxazole | H | OH | >100 |
| 65 | biphenyl-ethyl | H | H | 29.0 |
| 66 | 5-(thiophen-2-yl)pyridin-2-ethyl | H | OH | 5.91 |
| 67 | 4-(thiophen-3-yl)phenyl-ethyl | H | OH | 2.69 |

TABLE 9-continued

FRET assay data for N⁷-alkylated GMP derivatives.

| No. | —Y—R¹ | R³ | R⁴ | AC50/μM |
|---|---|---|---|---|
| 68 | 2-ethylbenzothiazole | H | OH | 52.9 |
| 69 | 2-ethylbenzothiophene | H | OH | 63.2 |
| 70 | 5-ethylbenzofurazan | H | OH | 23.7 |
| 71 | 2-ethyl-1-methylbenzimidazole | H | OH | >100 |
| 72 | 4-ethyl-1-methylindazole | H | OH | >100 |
| 73 | 6-ethyl-1-methylindazole | H | OH | >100 |
| 74 | 5-ethyl-1-methylindazole | H | OH | >100 |
| 75 | Me | H | OH | 25.8[b] |
| 76 | (E)-cinnamyl-ethyl | H | OH | >100 |
| 77 | benzyl propanoate | H | OH | >100 |
| 78 | N-(3-chlorophenyl)propanamide | H | OH | >100 |

*values for single measurement are reported unless otherwise noted.
[a] average value over 22 measurements
[b] average value over 2 measurements
[c] average value over 33 measurements
[d] average value over 3 measurements

TABLE 10

FRET assay data for N⁷-alkylated GDP derivatives.

| No. | —Y—R¹ | R³ | R⁴ | AC50/μM* |
|---|---|---|---|---|
| 1 | Me | H | Me | — |
| 2 | 4-ethylbiphenyl | H | H | 0.07 |
| 3 | 4-(4-cyclohexylphenyl)ethyl | H | H | 4.59 |

TABLE 10-continued

FRET assay data for N[7]-alkylated GDP derivatives.

[Structure: GDP with N[7]–Y–R[1], 2'-OR[4], 3'-OR[3]]

| No. | —Y—R[1] | R[3] | R[4] | AC50/μM* |
|---|---|---|---|---|
| 4 | —CH₂—(4-nitrophenyl) | H | H | 2.37 |
| 5 | —CH₂—(1-naphthyl) | H | H | 11.2 |
| 6 | —CH₂—(2-naphthyl) | H | H | 4.95 |
| 7 | —CH₂—(4-(5-methyl-1,2,4-oxadiazol-3-yl)phenyl) | H | H | 36.2 |
| 8 | —CH₂CH=CH—(4-chlorophenyl) | H | H | 0.06 |
| 9 | —CH₂—(5-(thiophen-2-yl)pyridin-2-yl) | H | H | 0.55[a] |
| 10 | —CH₂—(5-bromo-3-thienyl) | H | H | 1.01 |
| 11 | —CH₂—(2-phenylthiazol-4-yl) | H | H | 20.7 |
| 12 | —CH₂—(benzothiazol-2-yl) | H | H | 14.6 |
| 13 | —CH₂CH₂C(O)NH—(3-chlorophenyl) | H | H | 27.4 |
| 14 | —CH₂CH₂C(O)O—CH₂—phenyl | H | H | 75.0 |
| 15 | —CH₂—(4-(thiophen-2-yl)phenyl) | H | H | 0.16 |
| 16 | —CH(CH₃)—(diphenyl) | H | OH | 47.1[a] |

*values for single measurment are reported unless otherwise noted.
[a]average value over 2 measurements

TABLE 11

FRET assay data for N[7]-alkylated inosine derivatives.

[Structure: inosine polyphosphate with N[7]–CH₂–(4-biphenyl)]

| No. | n | AC50/μM* |
|---|---|---|
| 1 | 1 | 1.21 |
| 2 | 2 | 0.49[a] |

*values for single measurement are reported unless otherwise noted.
[a]average value over 2 measurements

TABLE 12

FRET assay data for $C^8$-substituted purine derivatives.

Scaffold A: R9-substituted xanthine with N7-(4-phenylbenzyl) group and C8-$Z_2$-P(O)(OH)$_2$ substituent, N3-methyl.

Scaffold B: hypoxanthine with N7-(2-(4-chlorophenoxy)ethyl) group and C8-$Z_2$-P(O)(OH)$_2$ substituent.

| No. | Scaffold | $R^9$ | $Z^2$ | AC50/μM* |
|---|---|---|---|---|
| 1 | A | H | 1,4-phenylene | 33.6– |
| 2 | A | Me | 1,4-phenylene | >100 |
| 3 | B | — | 1,4-phenylene | 2.1 |
| 4 | B | — | 1,4-phenylene-P(O)(OH)–O– | 0.3 |
| 5 | B | — | 1,4-phenylene-O– | 0.70 |
| 6 | B | — | cyclohexylene | >100 |
| 7 | B | — | trans-cyclohexylene-O– | >100 |
| 8 | B | — | trans-cyclopropylene-CH$_2$-O– | 18.2 |

Generation of 5'-Monophosphate mRNA:

Standard T7 transcription reactions result in 5'-triphosphate mRNA, which is not compatible with an imidazole phosphate activated cap analog if a triphosphate structure is desired in the final product. In order to generate a standard triphosphate cap structure using the imidazole activated Cap analogs described herein, the RNA substrate must have either a 5'-monophosphate mRNA (when using an imidazole-diphosphate cap analog) or 5'-diphosphate mRNA (when using an imidazole-monophosphate cap analog) for chemical capping. In an attempt to generate mono or diphosphate 5'-terminal mRNA, addition of either 10 mM GMP or 10 mM GDP to the transcription reaction was tested. While 10 mM GMP yielded >95% 5'-monophosphate mRNA, 10 mM GDP inhibited the transcription reactions altogether. Therefore for generation of 5'-triphosphate Cap mRNA structures we have focused on the use of 10 mM GMP containing transcription reactions and imidazole-diphosphate activated cap analogs.

In Vitro Transcription of mRNA (Leptin and Luciferase):

To generate the DNA template for in vitro transcription, the plasmid pGEM-oT7-TEV-oK-Gluc(NcoI)-2hBG-(NotI)-120A or pGEM-oT7-TEV-hLeptin-GAopt-2hBG-120A was linearized with restriction enzyme BspQ1 (New England Biolabs, Ipswich, Mass.) according to manufacturer's protocol. The linearized DNA vector was purified by precipitation with three volumes of 100% ethanol and 1/10 volume of 3M NaOAc, pH 5.1. This was followed by a wash with 70% ethanol and DNA was resuspended in water.

In vitro transcription was carried out in 40 mM Tris-HCl, pH 8, 8 mM MgCl2, 1 mM each NTP, 10 mM DTT, 2 mM spermidine, 0.004 U/uL inorganic pyrophosphatase (New England Biolabs, Ipswich, Mass.), 1U/uL RNase inhibitor (New England Biolabs, Ipswich, Mass.), 5U/μL T7 RNA polymerase (New England Biolabs, Ipswich, Mass.), and 0.2μg/μL of linearized plasmid DNA.

If mRNA preparation was for 5' end chemical capping, 10 mM of GMP (Sigma-Aldrich, St. Louis, Mo.) was spiked in the transcription reaction. The reaction was incubated at 37° C. for 1.5 h. The DNA template was digested by adding 0.04 U/μL of the TURBO DNase (Thermo Fisher, Waltham, Mass.) and incubated at 37° C. for another 30 min. The transcript was precipitated by LiCl (final concentration 2.81 mM), followed by a 70% ethanol wash. The pellet was resuspended in nuclease-free water.

Chemical Capping of RNA:

RNAs used were either a 20 nucleotide synthetic RNA molecule that was synthesized with a 5'-monophosphate (Integrated DNA Technologies: 5'-P-rGrGrArCrCrCrUr-CrUrCrCrUrCrUrCrCrCrCrC-3') or 5'-monophosphate containing mRNA in vitro transcribed as described above (Gaussia Luciferase mRNA or human leptin mRNA). Both 3'-modified and unmodified RNA was used.

RNA solution was first denatured in water by heating at 65° C. for 10 min. The mixture was cooled on ice for 5 min before being added to the capping buffer (100 mM MES buffer, pH 6.0, 100 mM NaCl and 5 mM MnC12). The imidazole activated Cap analog was then added to the reaction to a final concentration of 5 mM. The reaction was performed at room temperature overnight in a Thermoshaker (Grant Instrument, Cambridge, UK). The reaction was quenched by adding EDTA to a final concentration of 50 mM. The capped product was desalted using Amicon Ultra Centrifugal Filter Unit (Millipore, Billerica, Mass.). The product was further purified with LiCl precipitation (final 2.81 mM LiCl) and washed with 70% ethanol. The pellet was resuspended in nuclease-free water.

In some cases chemically capped mRNA was further purified using reverse phase HPLC using a Waters XBridge Shield RP18 3.5 um 2.1×100 mm column (Table 13). Mobile Phase A was 0.1 M triethyl ammonium acetate (TEAA) in water and Mobile Phase B was 0.1 M TEAA in 75% water/25% acetonitrile. The column flow rate was 0.8 mls/minute and the column temperature was 65° C. Fractions were collected manually.

TABLE 13

HPLC Purification Gradient.

| Time (min) | % Mobile Phase B |
|---|---|
| 0.1 | 44 |
| 3.0 | 44 |
| 13 | 64 |
| 14 | 90 |
| 15 | 90 |
| 15.1 | 44 |
| 20 | 44 |

LC/MS Analysis of Capping of the 20 Nucleotide Synthetic RNA Oligomer:

Capped and uncapped oligonucleotides were resolved on a Waters Acquity UPLC BEH C18, 1.7 μm, 100 Å, 2.1×75 mm column. The aqueous mobile phase contained 0.8 μM EDTA, 7.15 mM triethylamine and 192.3 mM hexafluoroisopropanol. The organic mobile phase is methanol. The column was kept at 65° C. with flow rate of 0.35 mL/min. A typical gradient ramped from 5% to 16% organic in 2 minutes followed by a ramp from 16% to 25% in 20 minutes. Post HPLC MS analysis of oligonucleotides was performed using either the Thermo LTQ-Orbitrap XL or ABSciex 6500 Q Trap. The mass spectrometers were run in ESI-MS negative mode scanning from 735 to 1550 m/z.

TABLE 14

Efficiency of chemical capping as determined by LC/MS.

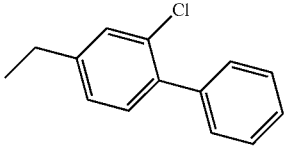

| No. | —Y—R¹ | % capped with 20 nt oligonucleotide RNA |
|---|---|---|
| 1 | 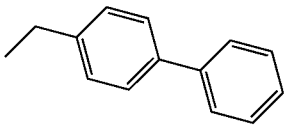 | 73 |
| 2 | 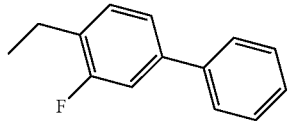 | 91 |

TABLE 14-continued

Efficiency of chemical capping as determined by LC/MS.

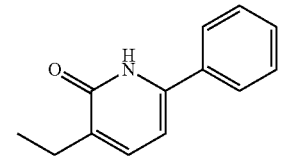

| No. | —Y—R¹ | % capped with 20 nt oligonucleotide RNA |
|---|---|---|
| 3 | 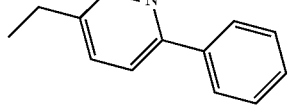 | 95 |
| 4 | 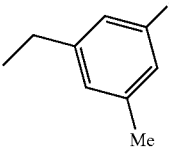 | 84 |
| 5 | 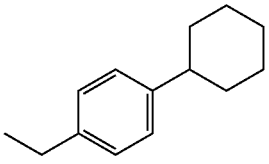 | >99 |
| 6 | Me | >99 |
| 7 | 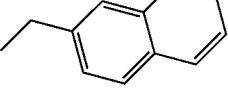 | 87 |
| 8 | 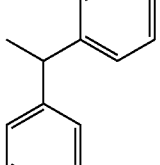 | 89 |
| 9 | | 97 |
| 10 | | 98 |

TABLE 15

Efficiency of chemical capping as determined by LC/MS.

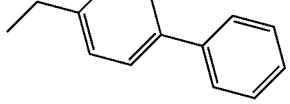

| No. | —Y—R¹ | % capped with 20 nt oligonucleotide RNA |
|---|---|---|
| 11 | (4-phenylbenzyl) | 65 |
| 12 | Bn | 84 |

TABLE 16

Efficiency of chemical capping as determined by LC/MS.

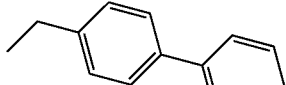

| No. | —Y—R¹ | % capped with 20 nt oligonucleotide RNA |
|---|---|---|
| 13 | (4-phenylbenzyl) | 99 |

TABLE 17

Efficiency of chemical capping as determined by LC/MS.

| No. | —Y—R¹ | X | % capped with 20 nt oligonucleotide RNA |
|---|---|---|---|
| 14 | (4-phenylbenzyl) | $CH_2$ | 87 |
| 15 | (4-phenylbenzyl) | NH | 21 |

Transfection of Luciferase mRNA and Luminescence Readout

Cell Culture:

HEK293 are seeded at a density of 30,000 cells/well in 96-well polyD lysine coated plates and incubated at 37° C., 5% $CO_2$ incubator overnight. Culture medium is EMEM (ATCC, cat #30-2003), 10% FBS (Invitrogen), no antibiotic.

mRNA Transfection:

100 ng/well of mRNA is transfected using 0.4 µl/well of DharmaFECT formulation2 (ThermoScientific T-2002-01). This is a 1:4 ratio of mRNA to transfection reagent. The mRNA and transfection reagent are mixed in OptiMEM to obtain a final volume of 10 µl/well. The mixture is incubated at room temperature for 20 minutes. The overnight culture medium is removed from cells by flipping the plate. 90 µl of fresh culture medium is added to each well. 10 µl of mRNA mixture is added to each well. The plate is incubated at 37° C., 5% $CO_2$ for 24 hours.

Media Collection:

Gaussia luciferase protein is secreted in the media. To collect media, 90 µl of media is transferred from the cells into a v-bottom 96 well plate. The plate is centrifuged at 1000 rpm for 5 minutes. 80 µl of supernatant is transferred into a new v-bottom plate and either frozen or used directly in Luciferase expression assay.

Luciferase Expression Assay:

BioLux Gaussia Luciferase Assay Kit (New England Biolabs Cat # E3300L) is used to perform the Luciferase assay. A 1:100 dilution of the BioLux gLUC substrate is made in Assay Buffer (10 µl substrate: 1000 µl Assay Buffer). 20 µl of the transfection media is added to a 96-well white clear bottom plate (Greiner bio-one 655095). The plate is read using the FlexStation 3 Microplate reader (Molecular Devices). At time 0, 50 uL of substrate mix is added to the media plate and data is collected for 60 seconds. The Relative Luminescence Unit (RLU) peaks at 30 seconds and the results are calculated using this time point. % luciferase activity is calculated by normalizing the RLU for each modified mRNA to the RLU for Enzymatically capped Cap-0 mRNA and multiplying by 100.

Luciferase activity of enzymatically capped HPLC purified mRNA (Cap-1) compared to HPLC purified chemically capped mRNAs Cap-1, Cap-2, and Cap-3 is shown in FIG. 1.

Figure 2:
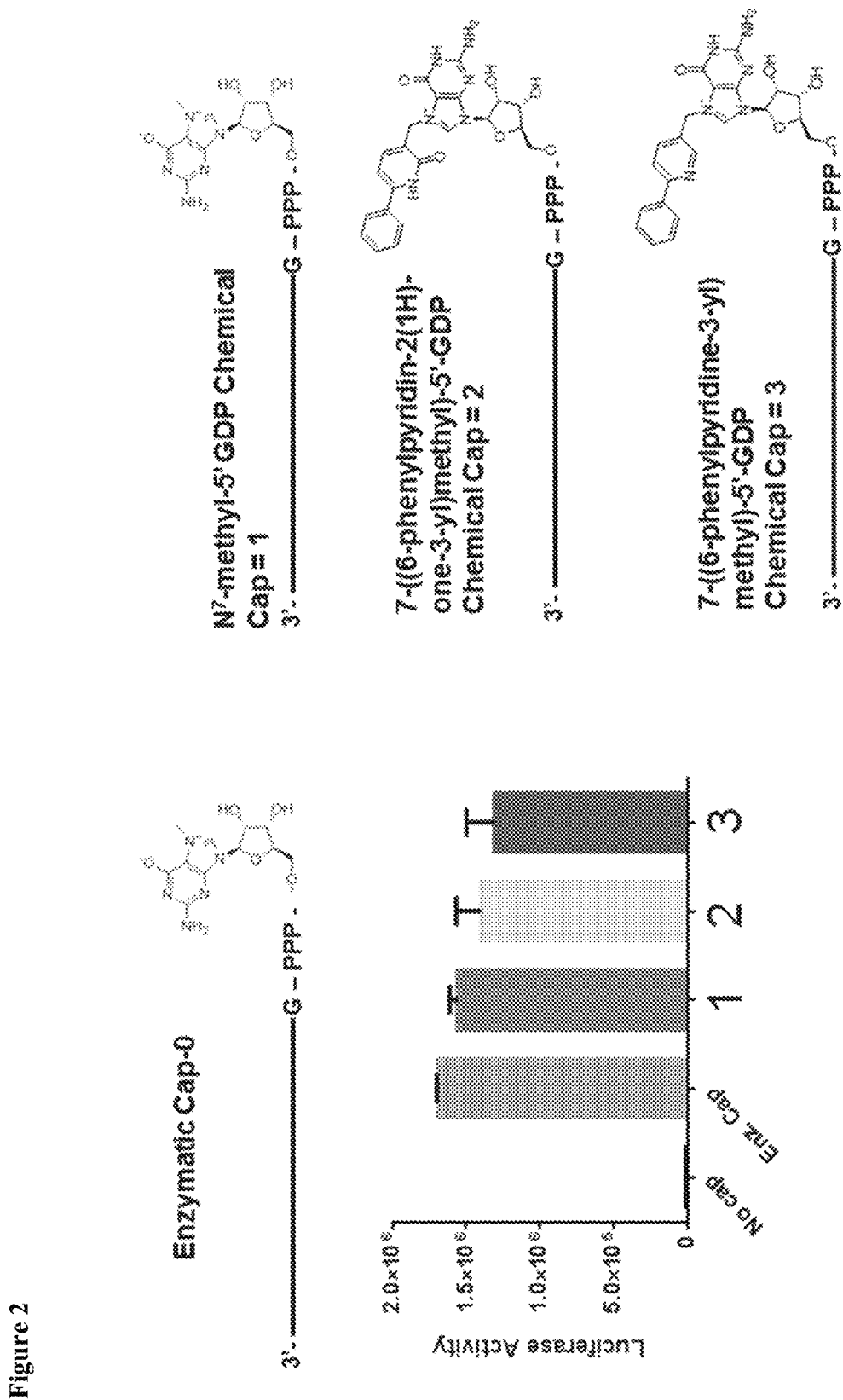
FIG. 2 is a bar graph and corresponding capped mRNAs depicting luciferase activity of enzymatically capped HPLC purified mRNA (Cap-0) compared to HPLC purified chemically capped mRNAs 1, 2, and 3.

Luciferase activity of enzymatically capped mRNA (Cap-0) compared to chemically capped mRNAs Cap-1, Cap-2, and Cap-3 is shown in FIG. 2.

Transfection of Capped Leptin mRNA and Luminescence Readout

Cell Culture:

HEK293 cells are seeded at a density of 30,000 cells/well in 96-well polyD lysine coated plates and incubated at 37° C., 5% $CO_2$ incubator overnight. Culture medium is EMEM (ATCC, cat #30-2003), 10% FBS (Invitrogen), no antibiotic.

mRNA Transfection:

100 ng/well of mRNA is transfected using 0.4 µl/well of DharmaFECT formulation2 (ThermoScientific T-2002-01). This is a 1:4 ratio of mRNA to transfection reagent. The mRNA and transfection reagent are mixed in OptiMEM to obtain a final volume of 10 µl/well. The mixture is incubated at room temperature for 20 minutes. The overnight culture medium is removed from cells by flipping the plate. 90 µl of fresh culture medium is added to each well. 10 µl of mRNA mixture is added to each well. The plate is incubated at 37° C., 5% $CO_2$ for 24 hours.

Media Collection:

The protein is secreted in the media. To collect media, 90 µl of media is transferred from the cells into a v-bottom 96 well plate. The plate is centrifuged at 1000 rpm for 5 minutes. 80 µl of supernatant is transferred into a new v-bottom plate.

Human Leptin Protein ELISA Assay:

Human leptin in mouse plasma was measured by ELISA. Antibodies purchased from the R&D systems duoset (Cat # DY398E, part #840279 for capture antibody and part #840280 for detection antibody) were reconstituted using PBS and titered, again using PBS. The capture antibody was coated at 4 µg/mL in 30 µl/well on a white Nunc® Maxisorp 384 well plate (Cat #460372). After an overnight incubation at room temperature the capture antibody was aspirated and the plate blocked for 2 hours at room temperature with 90 µL/well of KPL milk blocker (Cat #50-82-00). Once the incubation was completed the plate was aspirated and recombinant standards and samples were added to the plate at 30 µL/well for 2 hours at 37° C. while shaking at 600 rpm. Sample/standard dilutions were made using casein sample diluent (0.7% Casein, 1.7 mM Sodium Phosphate Monobasic, 8.1 mM sodium phosphate dibasic heptahydrate, 0.15 M NaCl, 0.7% Triton X-100, and 0.1% sodium azide). Washing/aspiration 3 times with 100 µl/well followed, using Teknova plate wash solution (Cat # P1192). Next, detection antibody was diluted using casein detection antibody diluent (0.4% Casein, 1.7 mM sodium phosphate monobasic, 8.1 mM sodium phosphate dibasic heptahydrate, 0.15 M NaCl, and 0.1% sodium azide) to 12.5 ng/mL and added at 30 µl/well for 2 hours room temperature. After this incubation, the plate was washed again and a solution of poly-streptavidin-HRP (Cat #21140) at a 1:1250 dilution in HRP dilution buffer (1.7 mM sodium phosphate monobasic, 8.1 mM sodium phosphate dibasic heptahydrate, 0.145 M NaCl, 0.1% chloroacetamide, 1% BSA Protease Free, and 0.05% Tween 20) was added to each well (30 µL/well) and incubated for 30 minutes room temperature. A final wash/aspiration removed the HRP solution and a chemiluminescent substrate was added at 30 µL/well (Cat #1859678 & 1859679). The plate was quickly read using a SpectramaxM5 plate reader with a 50 ms integration time. The dynamic range of the ELISA is from 5-150 pM of human leptin.

Figure 3:
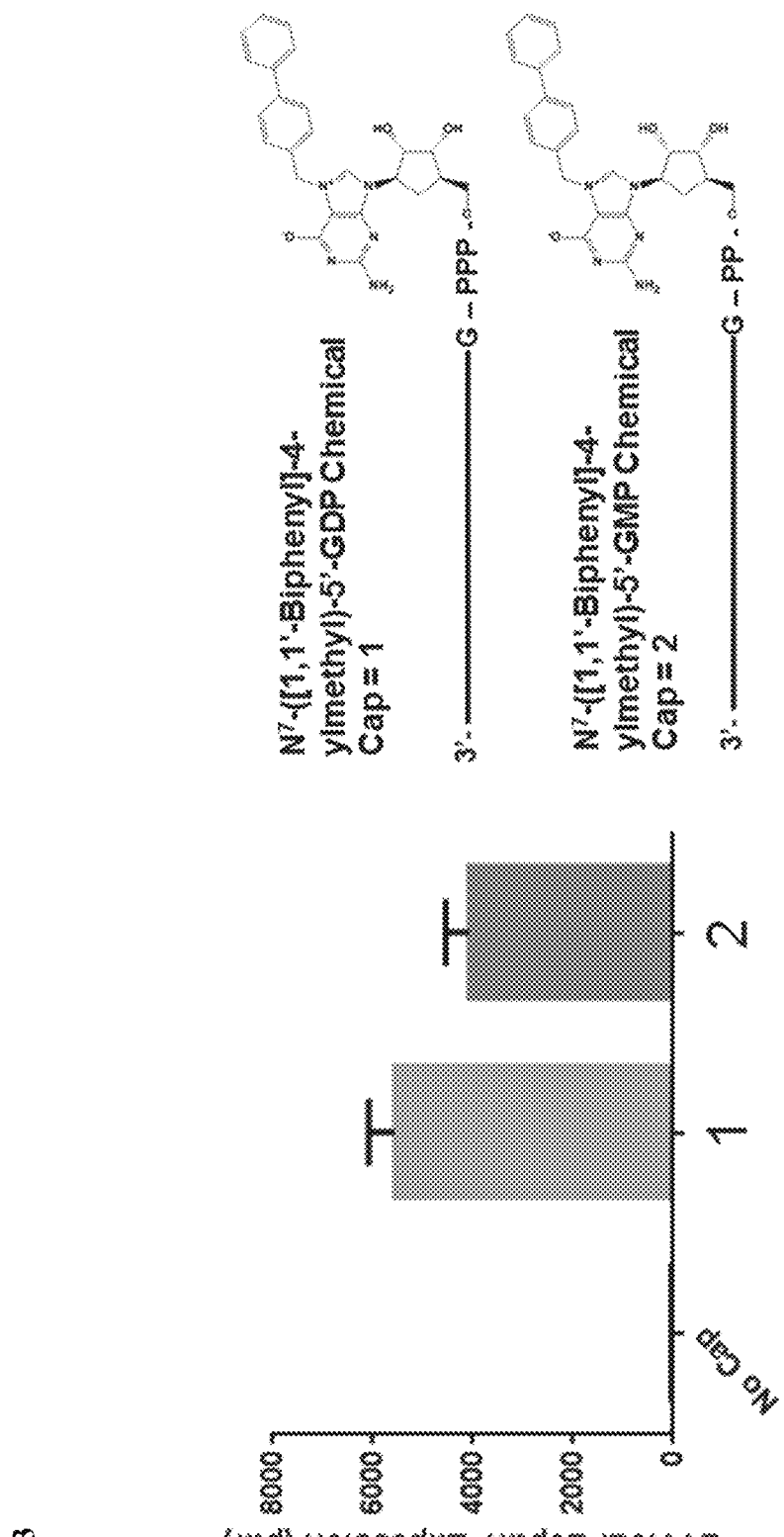
FIG. 3 is a bar graph and corresponding capped mRNAs depicting leptin expression data with chemically capped HPLC Purified mRNAs Cap-1 and Cap-2.

Leptin expression data with chemically capped HPLC Purified mRNAs Cap-1 and Cap-2 is shown in FIG. 3.

HEK293 Cell S100 Extract:

S100 extract was prepared following standard protocols for S100 preparation. HEK293 (Thermo Scientific SH30521.02) cells were grown in 80% FreeStyle 293 (Invitrogen 12338) and 20% SFM4 in 8% $CO_2$ with humidified atmosphere on an orbit shaker rotating at 100 rpm. $2.5 \times 10^9$ cells were pelleted at 1,500 rpm for 5 minutes in a clinical centrifuge. Pellet was washed in 1 L ice-cold DPBS and spun again at 1,500 rpm for 10 minutes at 4° C. in the clinical centrifuge. Supernatant was removed and cell pellet was resuspended in 250 ml of ice-cold PBS, broken up by pipetting and spun at 1,700 rpm for 6 minutes at 4° C. in the clinical centrifuge. Supernatant was removed and the pellet was resuspended in 5 volumes of Buffer A (10 mM HEPES-KOH, pH 7.9, 1.5 mM $MgCl_2$, 10 mM KCl, freshly added 0.5 mM DTT). Cells were incubated on ice for 10 minutes, spun at 2,000 rpm for 10 minutes and supernatant was removed. An additional volume of Buffer A was added and the pellet was broken up using 5 strokes of a loose pestle dounce homogenizer. Cells were lysed with 15 strokes of a tight pestle dounce homogenizer and lysis was confirmed using a microscope. Lysed material was spun at 4,500 rpm for 10 min at 4° C. in the clinical centrifuge. The supernatant was removed and used to make S100 extract. 0.11 volume of Buffer B (0.3 M HEPES-KOH, pH 7.9, 1.4 M KCl, 30 mM $MgCl_2$) was added to S100, mixed gently by inversion, and spun in ultracentrifuge at 102,000 g for 1 hour at 4° C. Supernatant was removed and placed in a chilled 15 mL conical tube. Clear supernatant from the bottom layer below the lipid layer was removed and dialysed against 1 L Buffer D (20 mM HEPES-KOH, pH 7.9, 20% glycerol, 0.1 M KCl, 0.2 mM EDTA, 0.5 mM DTT, 0.5 mM PMSF) for >5 hours at 4° C. S100 extract was stored at 80° C. in small aliquots until ready for use.

FRET RNA Degradation Assay:

The RNA degradation assay was performed following the protocol in Uhler et al J. Am. Chem. Soc. 2003, 125, 14230-14231 with some modifications. The oligos 5-/5Phos/rGrU/iFluorT/rUrCrG rCrCrA rUrU/i6-TAMN/rArArA rArArA rArArA rA-3 and 5-/5Phos/rGrU/iFluorT/rUrCrG rCrCrA rUrU/i6-TAMN/rArArA rArArA rArArA rA/3BIO-3 were purchased from IDT and used in the RNA degradation assay. The assay buffer consisted of 130 mM K-glutamate pH7.5, 1 mM MgCl2. DTT was added to a final concentration of 10 mM just prior to experiment. 100 uM or 200 uM oligo was used depending on the reaction volume 25 uL and 50 uL, respectively. S100 extract varied from 0.3%-20% v/v and Buffer D was 20% of total reaction volume for all samples. All reactions were run in 384 well plate at 37° C. At 100 sec, S100 extract was added to the oligo buffer mix. Fluorescein was excited at 490 nm and fluorescence emission was measured at 520 nm and 585 nm. Data were collected every minute for 2 hours. The FRET ratio Q (=F585/F520) was calculated and normalized to the initial value $Q_0$. The data were fit to the single-exponential decay function $y = y_0 - \text{Plateau} \cdot \exp(-K \cdot X) + \text{Plateau}$ using Prism 5.0. To extract Michaelis-Menten parameters, the dependence of the rate constant $k_{dec}$ on % S100 [X] was fit to the Michaelis-Menten equation $Y = V_{max} \cdot X/(K_m + X)$ using Prism 5.0.

TABLE 18

Stability of FRET RNA oligo in 1.2% HEK293 S-100 extract.

| No. | 5'-oligonucleotide-3'—Z₃ | 3' end compound | T₁/₂ (s) |
|---|---|---|---|
| 1 | (structure of adenosine with phosphate Z₃) | Unmodified | 424 ± 65 |
| 2 | (structure with biotin linker) | biotin | 1046 ± 176 |

TABLE 18-continued
Stability of FRET RNA oligo in 1.2% HEK293 S-100 extract.
| No. | 3' end compound | $T_{1/2}$ (s) |
|---|---|---|
| 3 | Exp10 | 3563 ± 1486 |
| 4 | Exp11 | 1906 ± 648 |
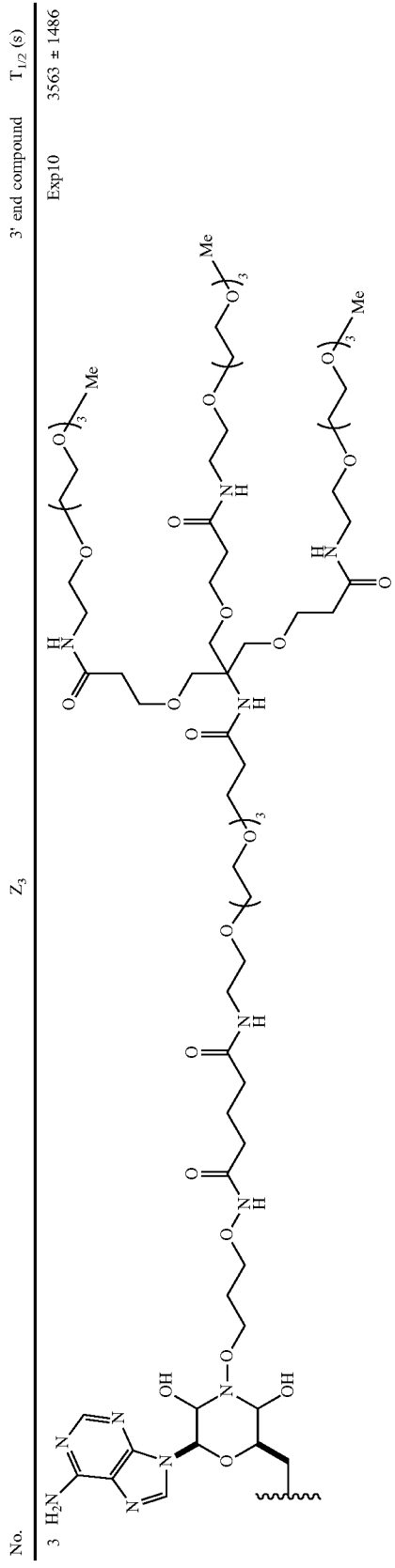

TABLE 18-continued

Stability of FRET RNA oligo in 1.2% HEK293 S-100 extract.

| No. | 5'-oligonucleotide-3' $Z_3$ | 3' end compound | $T_{1/2}$ (s) |
|---|---|---|---|
| 5 |  | Exp25 | 879 |
| 6 |  | Exp30 | 1006 |

TABLE 18-continued
Stability of FRET RNA oligo in 1.2% HEK293 S-100 extract.
| No. | Z₃ | 3' end compound | T₁/₂ (s) |
|---|---|---|---|
| 7 | 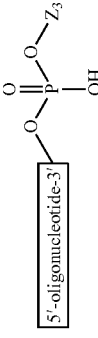 | Exp39 | 2464 |
| 8 | 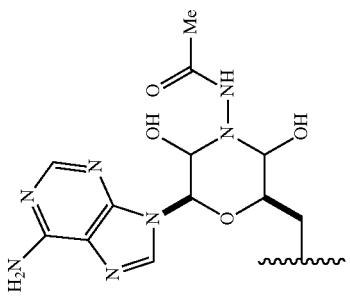 | Exp40 | 275940 |

TABLE 18-continued
Stability of FRET RNA oligo in 1.2% HEK293 S-100 extract.
| No. | $Z_3$ | 3' end compound | $T_{1/2}$ (s) |
|---|---|---|---|
| 9 | 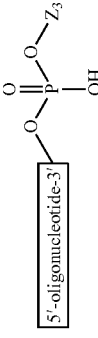 | Exp41 | 23160 |

3' End Modification of mRNA

Transfection of Luciferase 3' End Modified mRNA and Luminescence Readout:

Cell Culture:

HEK293 cells are seeded at a density of 30,000 cells/well in 96-well polyD lysine coated plates and incubated at 37 C, 5% $CO_2$ incubator overnight. Culture medium is EMEM (ATCC, cat #30-2003), 10% FBS (Invitrogen), no antibiotic.

mRNA Transfection:

30 ng/well of mRNA is transfected using 0.4 μl/well of DharmaFECT formulation2 (ThermoScientific T-2002-01). The mRNA and transfection reagent are mixed in OptiMEM to obtain a final volume of 10 μl/well. The mixture was incubated at room temperature for 20 minutes. The overnight culture medium was removed from cells by flipping the plate. 90 μl of fresh culture medium was added to each well and 10 l of mRNA mixture was added to each well. The plate is incubated at 37° C., 5% $CO_2$ for 24 hours.

Media Collection:

Gaussia luciferase protein is secreted in the media. To collect media, 24 hours after transfection, 90 μl of media was transferred from the cells into a v-bottom 96 well plate and centrifuged at 1000 rpm for 5 minutes. 80 μl of supernatant was transferred into a new v-bottom plate and either frozen or used directly in Luciferase expression assay or leptin elisa.

Luciferase Expression Assay:

BioLux Gaussia Luciferase Assay Kit (New England Biolabs Cat # E3300L) is used to perform the Luciferase assay. A 1:100 dilution of the BioLux gLUC substrate is made in Assay Buffer (10 μl substrate: 1000 μl Assay Buffer). 20 μl of the transfection media is added to a 96-well white clear bottom plate (Greiner bio-one 655095). The plate is read using the FlexStation 3 Microplate reader (Molecular Devices). At time 0, 50 uL of substrate mix is added to the media plate and data is collected for 60 seconds. The Relative Luminescence Unit (RLU) peaks at 30 seconds and the results are calculated using this time point. % luciferase activity is calculated by normalizing the RLU for each modified mRNA to the RLU for enzymatically capped Cap1 mRNA and multiplying by 100.

TABLE 19

3' modified GLuc-mRNA expression data in HEK293 cells.

| No. | $Z_3$ | 3' end compound | % Luciferase activity* |
|---|---|---|---|
| 1 | 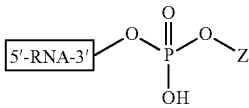 | Unmodified | 100 |
| 2 | 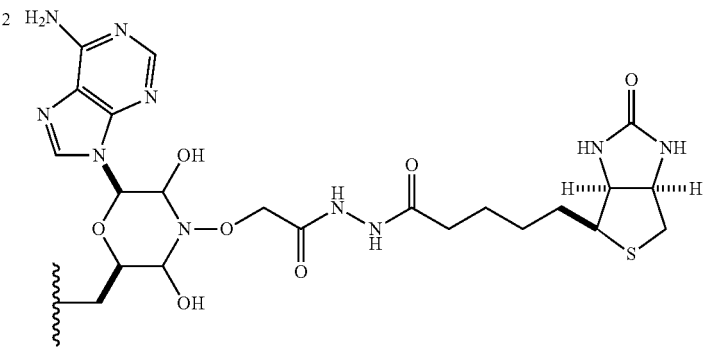 | biotin | 443.5 ± 97 |

TABLE 19-continued
3' modified GLuc-mRNA expression data in HEK293 cells.
| No. | Z₃ | 3' end compound | % Luciferase activity* |
|---|---|---|---|
| 4 | 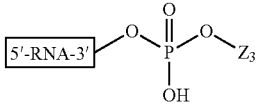 | Exp048 | 311 |
| 5 | 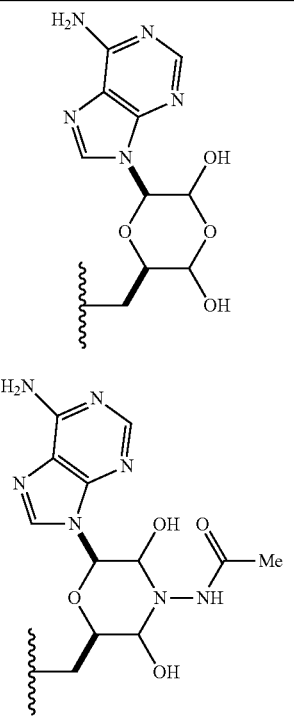 | Exp051 | 451 ± 136 |
| 6 | 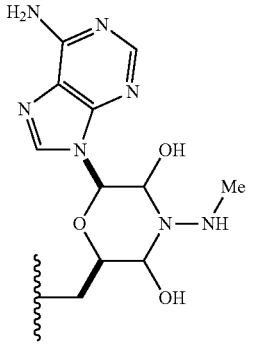 | Exp049 | 287 |
| 7 | 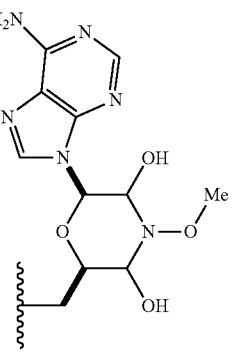 | Exp050 | 513 ± 341 |

TABLE 19-continued

3' modified GLuc-mRNA expression data in HEK293 cells.

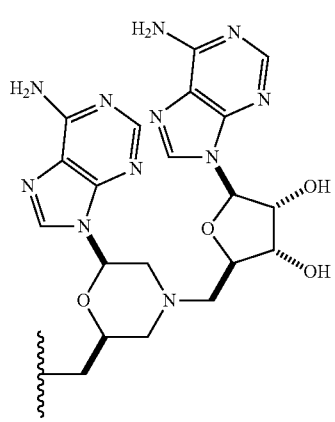

| No. | $Z_3$ | 3' end compound | % Luciferase activity* |
|---|---|---|---|
| 8 | 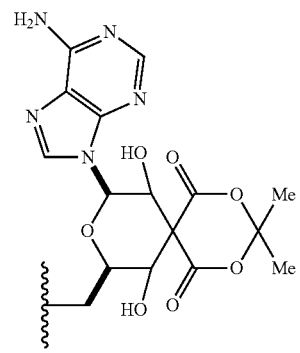 | Exp057 | 268 |
| 9 | 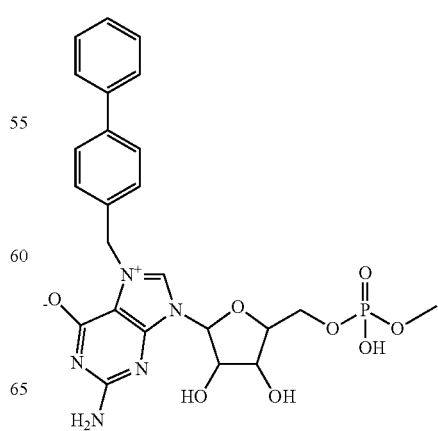 | Exp058 | 268 |

*normalized to umodified 24 hours after transfection.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

199
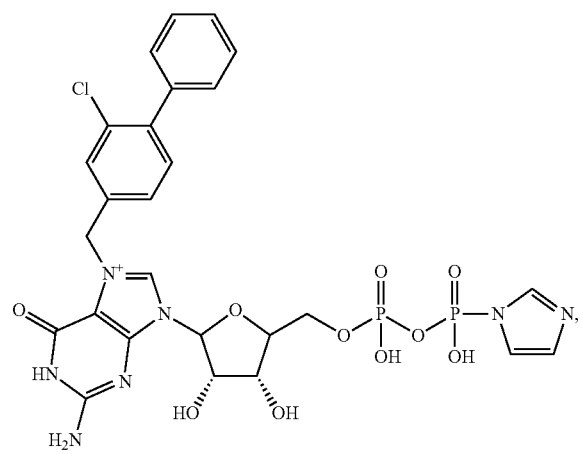
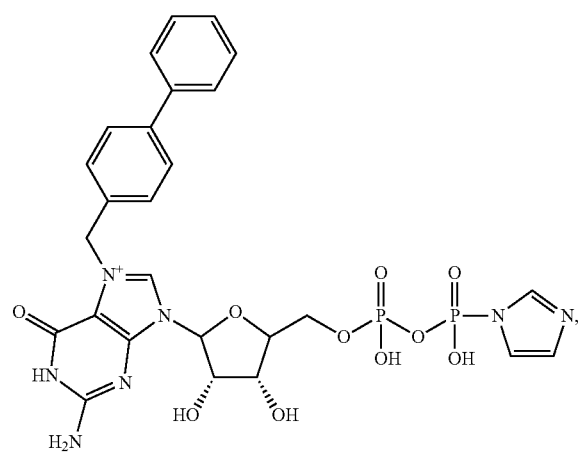
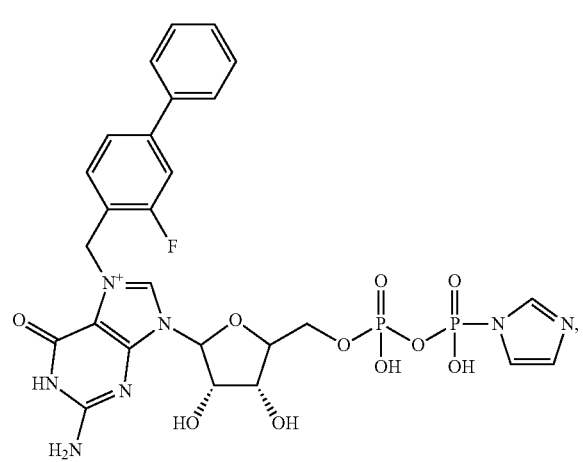
200
-continued
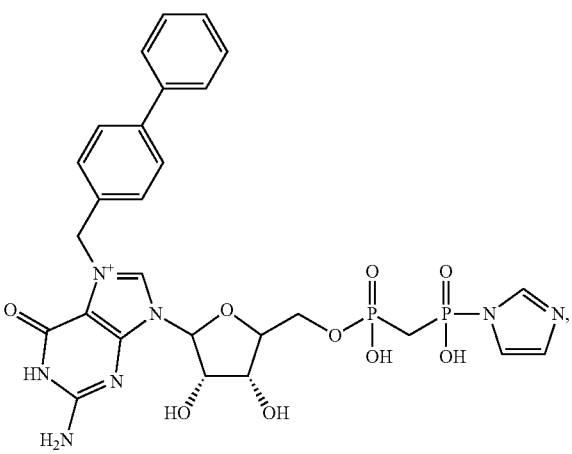 [SMILES: Nc1nc2c(c(=O)[nH]1)[n+](Cc1ccc(-c3ccccc3)cc1)cn2C1OC(COP(=O)(O)CP(=O)(O)n2ccnc2)[C@H](O)[C@@H]1O]
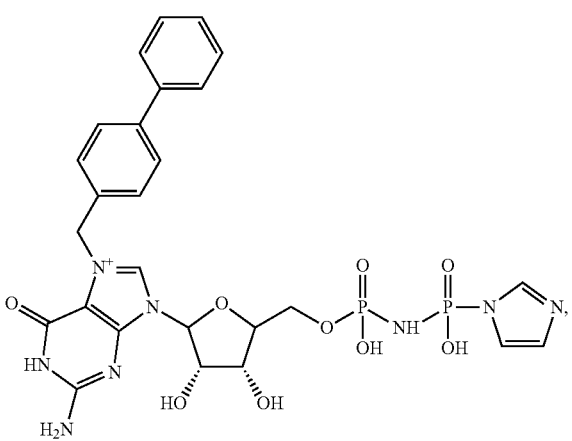
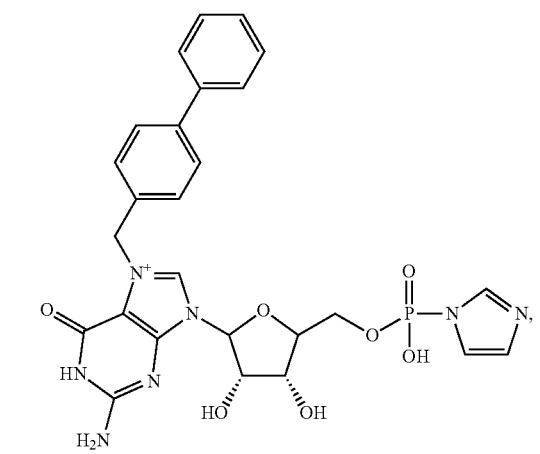

201
-continued
202
-continued
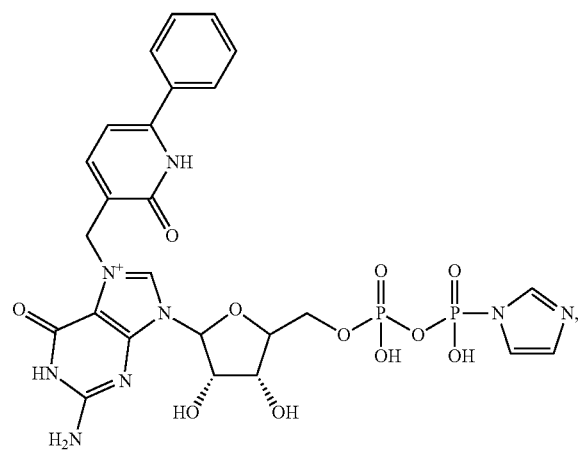
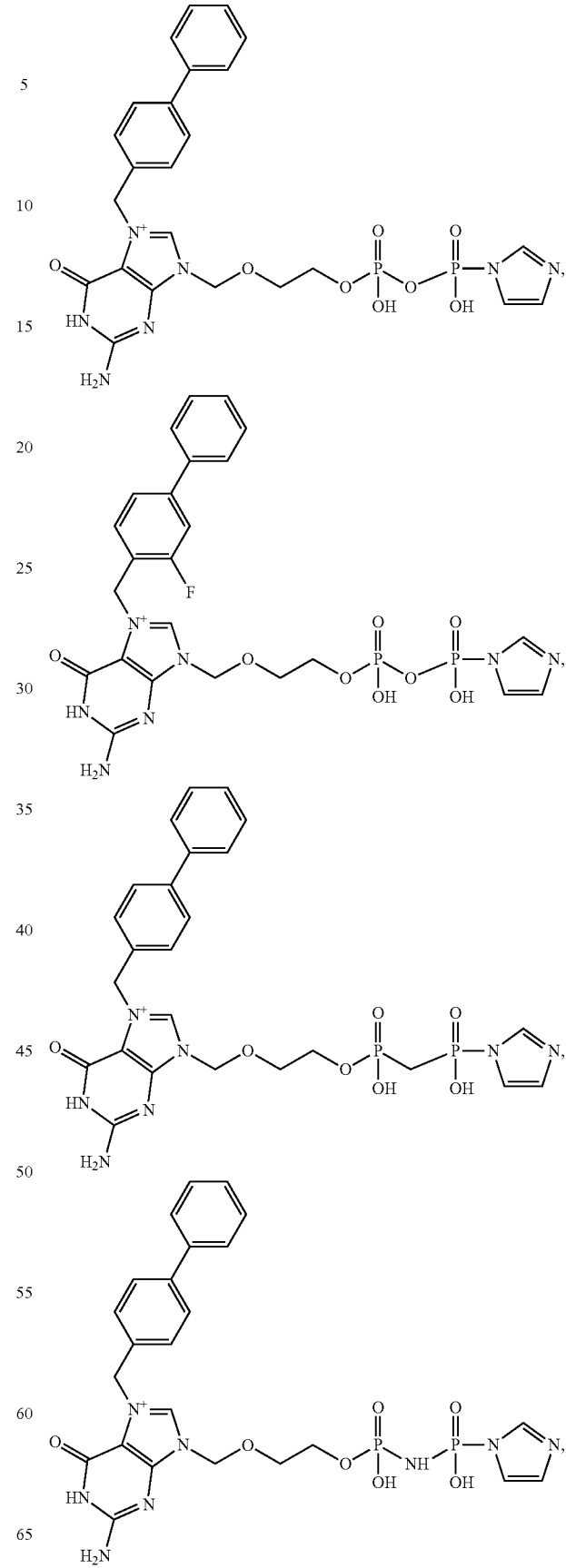

and
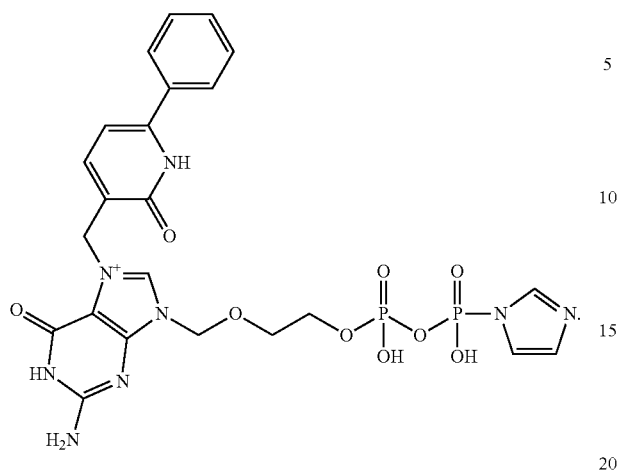

The invention claimed is:

1. A compound or a pharmaceutically acceptable salt thereof selected from the group consisting of:

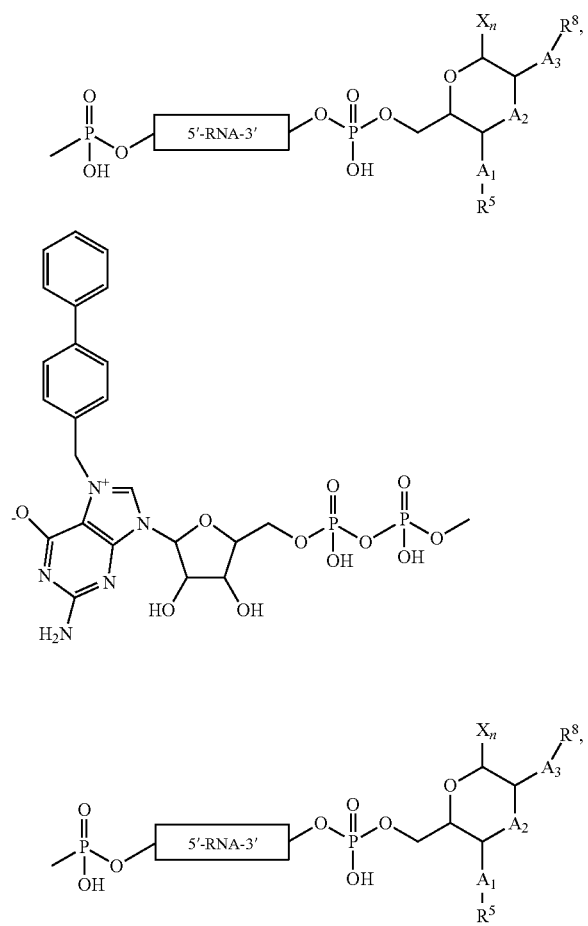
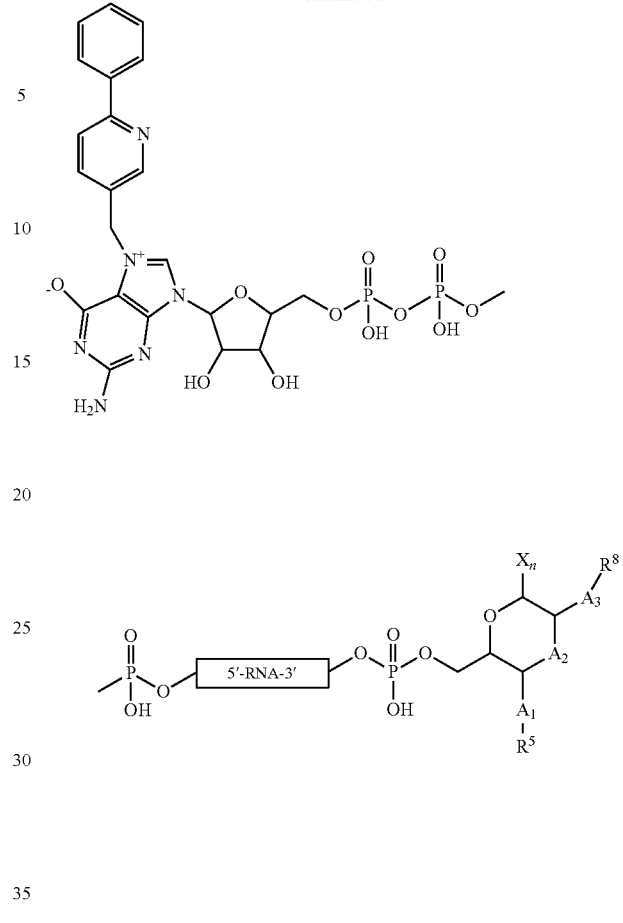
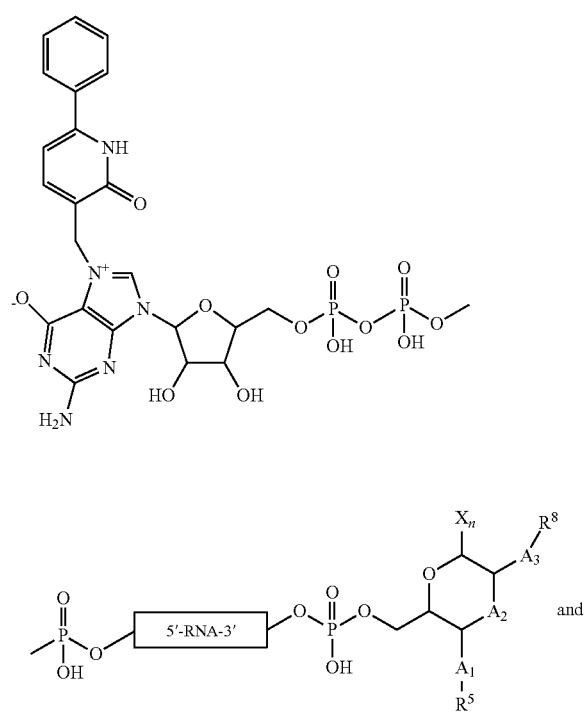

and wherein:

$A_1$ and $A_3$ are independently selected from the group consisting of absent, NH, S, and O;

$A_2$ is absent or selected from the group consisting of $>CR^6R^7$, $>NR^6$, $>NNR^6R^7$, $>NOR^6$, $>S$, and $>O$;

$R^5$, $R^6$ and $R^8$ are independently selected from the group consisting of H, substituted alkyl, polyamine, PEGs, —$(CH_2)_{n1}NR^{12}R^{13}$, —$(CH_2)_{n1}NR^{14}C(O)R^{15}$, —$(CH_2)_{n1}OR^{15}$, —$(CH_2)_{n1}C(O)OR^{15}$, —$(CH_2)_{n1}C(O)R^{15}$, —$(CH_2)_{n1}C(O)NR^{12}R^{13}$, —O—$(CH_2)_{n3}$—C(O)—$(NR_{12})_2$—C(O)$X_2$, and —O—$(CH_2)_{n3}$—C(O)—[$NR_{12}$—C(O)—$(CH_2)_{n3}$]$_{1-3}$—$X_2$; or $R^6$ and $R^8$ together form a ring that is substituted and contains 10-80 ring atoms in which 10-40 ring atoms can be heteroatoms, or $R^6$ and $R^7$ together form a 3-8 membered ring that is substituted and in which 1 or 6 ring atoms can be heteroatoms;

$R^7$, $R^{12}$, $R^{13}$, $R^{14}$, and $R^{15}$ are independently selected from the group consisting of H, substituted lower alkyl, and substituted acyl;

n1 is zero to 10;

n3 is 1 to 8;

$X_2$ is selected from the group consisting of affinity moiety and detection moiety; and $X_n$ is a nucleobase.

2. A compound or a pharmaceutically acceptable salt thereof selected from the group consisting of: